(12) United States Patent
Liu et al.

(10) Patent No.: US 7,511,032 B2
(45) Date of Patent: Mar. 31, 2009

(54) PYRROLOBENZODIAZEPINE DERIVATIVES, COMPOSITIONS COMPRISING THE SAME AND METHODS RELATED THERETO

(75) Inventors: Paul S Liu, Chevy Chase, MD (US); B. Rao Vishnuvajjala, Rockville, MD (US); Kenneth M Snader, Vero Beach, FL (US); David E Thurston, Fareham (GB); Philip W Howard, St. Albans (GB); Luke Y Hsiao, San Diego, CA (US); Gregory Turner, Independence, MO (US)

(73) Assignees: The United States of America as represented by the Secretary, Department of Health and Human Services, Washington, DC (US); Starks Associates, Inc., Buffalo, NY (US); Midwest Research Institute, Kansas City, MO (US); Spirogen, Ltd., London (GB)

( * ) Notice: Subject to any disclaimer, the term of this patent is extended or adjusted under 35 U.S.C. 154(b) by 124 days.

(21) Appl. No.: 10/576,689

(22) PCT Filed: Oct. 22, 2004

(86) PCT No.: PCT/US2004/035050

§ 371 (c)(1),
(2), (4) Date: Aug. 14, 2006

(87) PCT Pub. No.: WO2005/040170

PCT Pub. Date: May 6, 2005

(65) Prior Publication Data

US 2007/0072846 A1 Mar. 29, 2007

Related U.S. Application Data

(60) Provisional application No. 60/513,751, filed on Oct. 22, 2003.

(51) Int. Cl.
*C07D 487/04* (2006.01)
*A61K 31/551* (2006.01)
*A61P 31/00* (2006.01)

(52) U.S. Cl. .................. 514/220; 540/496
(58) Field of Classification Search .......... 540/496; 514/220
See application file for complete search history.

(56) References Cited

U.S. PATENT DOCUMENTS

| 4,464,467 | A | 8/1984 | Hatori et al. |
| 4,508,647 | A | 4/1985 | Hatori et al. |
| 2003/0120069 | A1 | 6/2003 | Thurston et al. |

FOREIGN PATENT DOCUMENTS

| EP | 1 193 270 B1 | 4/2002 |
| JP | 58180487 | 10/1983 |
| WO | WO 93/18045 | 9/1993 |
| WO | WO 00/12508 | 3/2000 |

OTHER PUBLICATIONS

Alley et al., *Proc. Amer. Assoc. Cancer Res.*, 43, #315 (2002).
Arima et al., *J. Antibiotics*, 25(8), 437-444 (1972).
Bose et al., *Tetrahedron*, 48(4), 751-758 (1992).
Gregson et al., *Chem. Commun.*, 9, 797-798 (1999).
Gregson et al., *J. Med. Chem.*, 44(5), 737-748 (2001).
Gregson et al., *J. Med. Chem.*, 47(5), 1161-1174 (2004).
Hara et al., *J. Antibiotics*, 41(5), 702-704 (1988).
Hartley et al., *Proc. Amer. Assoc. Cancer Res.*, 43, #2432 (2002).
Hochlowski et al., *J. Antibiotics*, 40(2), 145-148 (1987).
Hurley et al., *Acc. Chem. Res.*, 19, 230-237 (1986).
Itoh et al., *J. Antibiotics*, 41(9), 1281-1284 (1988).
Kohn, *Antibiotics*, 3, 3-11 (1975).
Konishi et al., *J. Antibiotics*, 37(3), 200-206 (1984).
Kuminoto et al., *J. Antibiotics*, 33(6), 665-667 (1980).
Langley et al., *J. Org. Chem.*, 52(1), 91-97 (1987).
Leber et al., *J. Am. Chem. Soc.*, 110(9), 2992-2993 (1988).
Leimgruber et al., *J. Am. Chem. Soc.*, 87(24), 5793-5795 (1965).
Mountzouris et al., *J. Med. Chem.*, 37(19), 3132-3140 (1994).
Sagnou et al., *Bioorg. Med. Chem. Lett.*, 10, 2083-2086 (2000).
Shimizu et al., *J. Antibiotics*, 35(8), 972-978 (1982).
Smellie et al., *Br. J. Cancer.*, 70, 48-53 (1994).
Takeuchi et al., *J. Antibiotics*, 29(1), 93-96 (1976).
Thurston et al., *Chem. Brit.*, 26, 767-772 (1990).
Thurston et al., *Chem. Rev.*, 94(2), 433-465 (1994).
Thurston et al., *J. Org. Chem.*, 61(23), 8141-8147 (1996).
Tsunakawa et al., *J. Antibiotics*, 41, 1366-1373 (1988).
Turner et al., 37th Midwest Regional Meeting of the American Chemical Society, Abstract, Oct. 23-25 (2002).
Walton et al., *Cancer Chemother. Pharmacol.*, 38, 431-438 (1996).

*Primary Examiner*—Bruck Kifle
(74) *Attorney, Agent, or Firm*—Leydig, Voit & Mayer, Ltd.

(57) ABSTRACT

Disclosed are compounds of Formula (I) wherein X, Y, $R_1$-$R_7$, $T^1$, $T^2$, Z, and p are as described herein; a pharmaceutical composition comprising a compound of Formula (I) and a carrier; a method of inhibiting growth of a cell, which method comprises administering in an amount effective to inhibit growth a compound of Formula (I); a method of treating cancer in a mammal, which method comprises administering in an amount effective to treat cancer a compound of Formula (I); a method of treating a viral, parasitic, or bacterial infection of a cell, which method comprises administering in an amount effective to treat a viral, parasitic, or bacterial infection a compound of Formula (I); and a method of preparing a compound of Formula (I) as described herein.

(I)

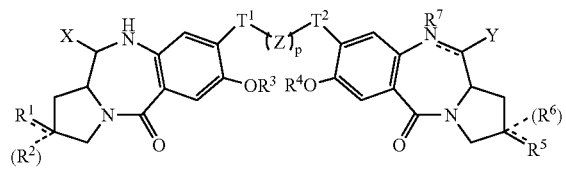

39 Claims, 13 Drawing Sheets

PYRROLOBENZODIAZEPINE DERIVATIVES, COMPOSITIONS COMPRISING THE SAME AND METHODS RELATED THERETO

CROSS-REFERENCE TO RELATED APPLICATION

This application claims the benefit of U.S. Provisional Patent Application No. 60/513,751, filed Oct. 22, 2003.

FIELD OF THE INVENTION

The invention pertains to derivatives of pyrrolobenzodiazepine, a pharmaceutical composition comprising such a derivative, a method of inhibiting growth of a cell, a method of treating cancer, and a method of treating a viral, parasitic, or bacterial infection of a cell using such derivatives, and a method of preparing the derivatives.

BACKGROUND OF THE INVENTION

Pyrrolobenzodiazepines (PBDs) have been shown to be able to recognize and bind to specific sequences of DNA. The most preferred sequence is PuGPu (Purine-Guanine-Purine). The first PBD antitumour antibiotic, anthramycin, was discovered in 1965 (Leimgruber et al., 1965 *J. Am. Chem. Soc.*, 87, 5793-5795; and Leimgruber et al., 1965 *J. Am. Chem. Soc.*, 87, 5791-5793). Since then, a number of naturally occurring PBDs have been reported, and over 10 synthetic routes have been developed to a variety of analogues (Thurston et al., 1994 *Chem. Rev.* 1994, 433-465). Family members include abbeymycin (Hochlowski et al., 1987 *J. Antibiotics*, 40, 145-148), chicamycin (Konishi et al., 1984 *J. Antibiotics*, 37, 200-206), DC-81 (Japanese Patent 58-180 487; Thurston et al., 1990, *Chem. Brit.*, 26, 767-772; and Bose et al., 1992 *Tetrahedron*, 48, 751-758), mazethramycin (Kuminoto et al., 1980 *J. Antibiotics*, 33, 665-667), neothramycins A and B (Takeuchi et al., 1976 *J. Antibiotics*, 29, 93-96), porothramycin (Tsunakawa et al., 1988 *J. Antibiotics*, 41, 1366-1373), prothracarcin (Shimizu et al, 1982 *J. Antibiotics*, 29, 2492-2503; and Langley and Thurston, 1987 *J. Org. Chem.*, 52, 91-97), sibanomicin (DC-102; Hara et al., 1988 *J. Antibiotics*, 41, 702-704; and Itoh et al., 1988 *J. Antibiotics*, 41, 1281-1284), sibiromycin (Leber et al., 1988 *J. Am. Chem. Soc.*, 110, 2992-2993) and tomamycin (Arima et al., 1972 *J. Antibiotics*, 25, 437-444).

PBDs are of the general structure:

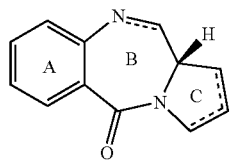

The PBDs differ in the number, type and position of substituents, in both their aromatic A rings and pyrrolo C rings, and in the degree of saturation of the C ring. In the B-ring there is either an imine (N=C), a carbinolamine (NH—CH(OH)) or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, 1975 In *Antibiotics III*. Springer-Verlag, New York, pp. 3-11; and Hurley and Needham-VanDevanter, 1986 *Acc. Chem. Res.*, 19, 230-237). Their ability to form an adduct in the minor groove enables them to interfere with DNA processing, hence their use as antitumor agents.

Despite the existence of such PBDs, there still exists a need in the art for derivatives or modifications of PBDs having attractive biological activity, e.g., ones that are able to bind to DNA, such that cellular transcription and gene expression are inhibited. Such compounds could then be used in methods of treating diseases in which it is useful to inhibit gene expression, e.g., cancer and other hyperproliferative diseases, as well, as diseases caused by viral, parasitic, or bacterial infections.

The invention provides such compounds. This and other objects and advantages of the invention, as well as additional inventive features, will be apparent from the description of the invention provided herein.

BRIEF SUMMARY OF THE INVENTION

The invention provides a compound of Formula I:

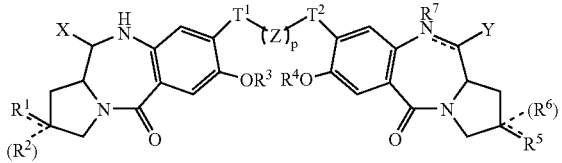

(Formula I)

wherein X, Y, $R_1$-$R_7$, $T^1$, $T^2$, Z, and p are as described herein.

The invention also provides a pharmaceutical composition comprising a compound of Formula I as described herein and a pharmaceutically-acceptable carrier, as well as a method of inhibiting the growth of a cell, which method comprises administering to the cell in an amount effective to inhibit the growth of the cell a compound of the invention, and a method of treating a viral, parasitic, or bacterial infection of a cell, which method comprises administering to the cell in an amount effective to treat a viral, parasitic, or bacterial infection a compound of the invention. Methods of preparing the compounds of the invention also are provided herein, which methods generally comprise combining a compound of formula I with water or a nucleophilic organic reactant.

DETAILED DESCRIPTION OF THE INVENTION

Figure 1A:
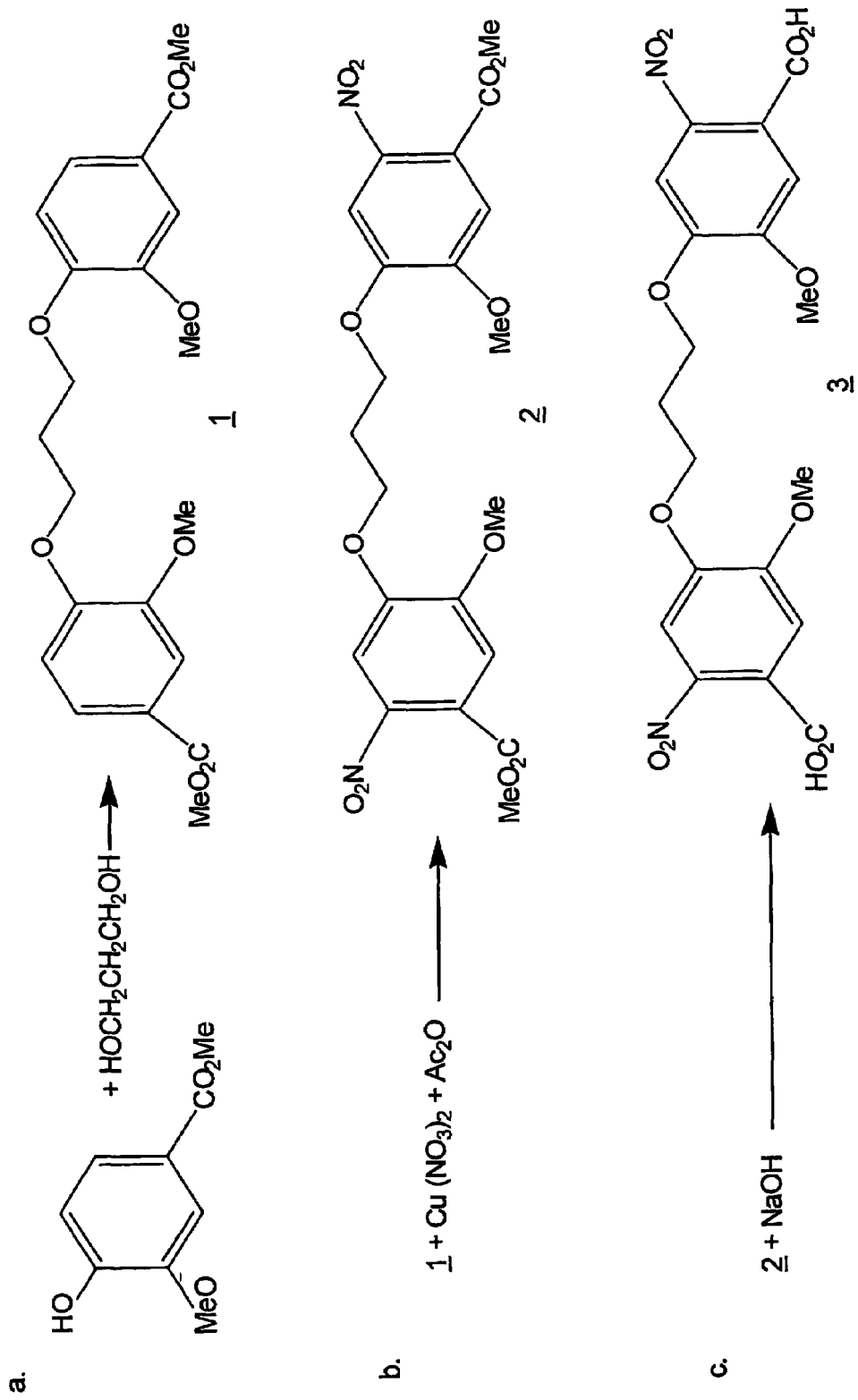
FIG. 1A depicts a reaction scheme illustrating steps (a)-(c) for preparing a compound in accordance with an embodiment of the invention.
Figure 1B:
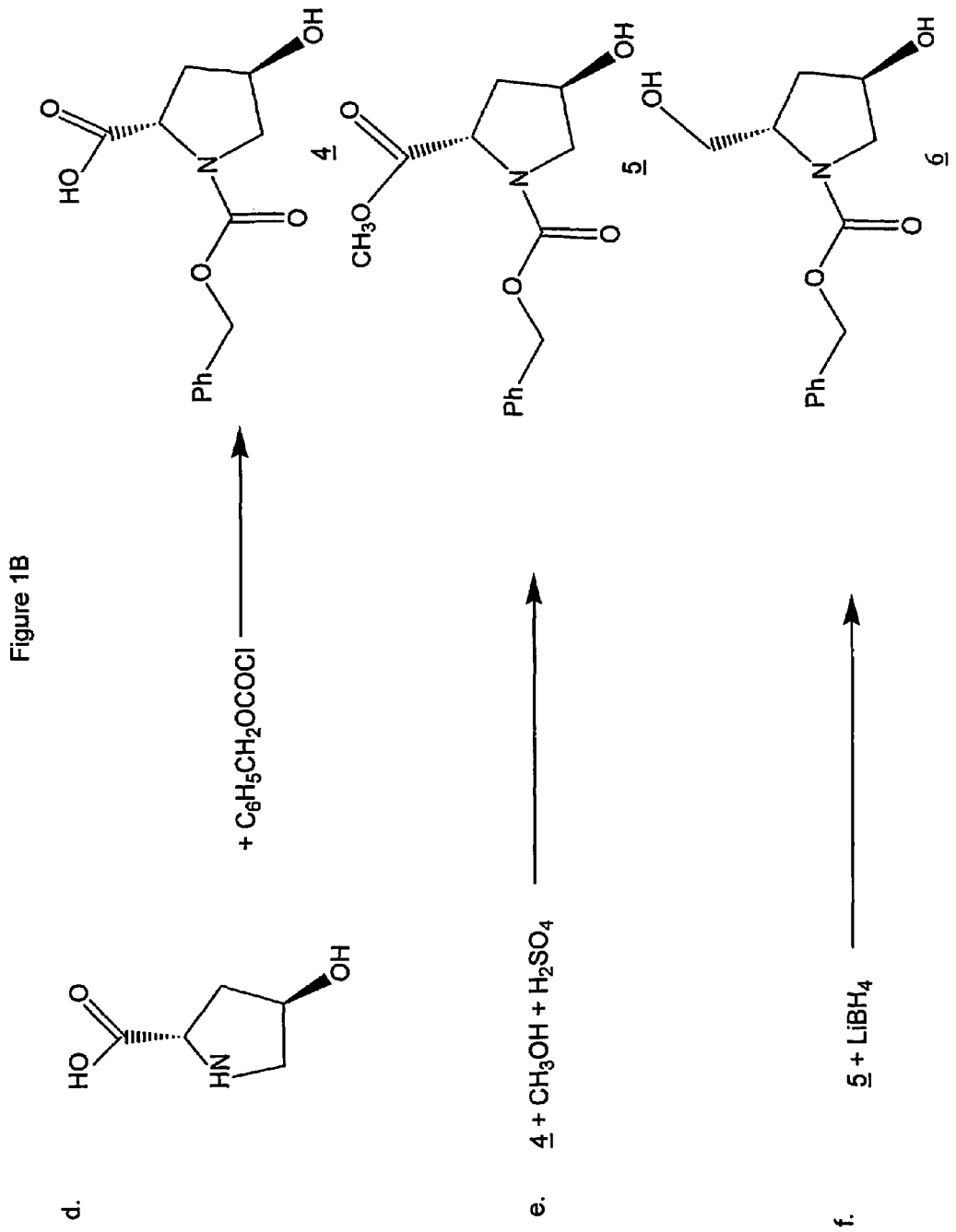
FIG. 1B depicts a reaction scheme illustrating steps (d)-(f) for preparing a compound in accordance with an embodiment of the invention.
Figure 1C:
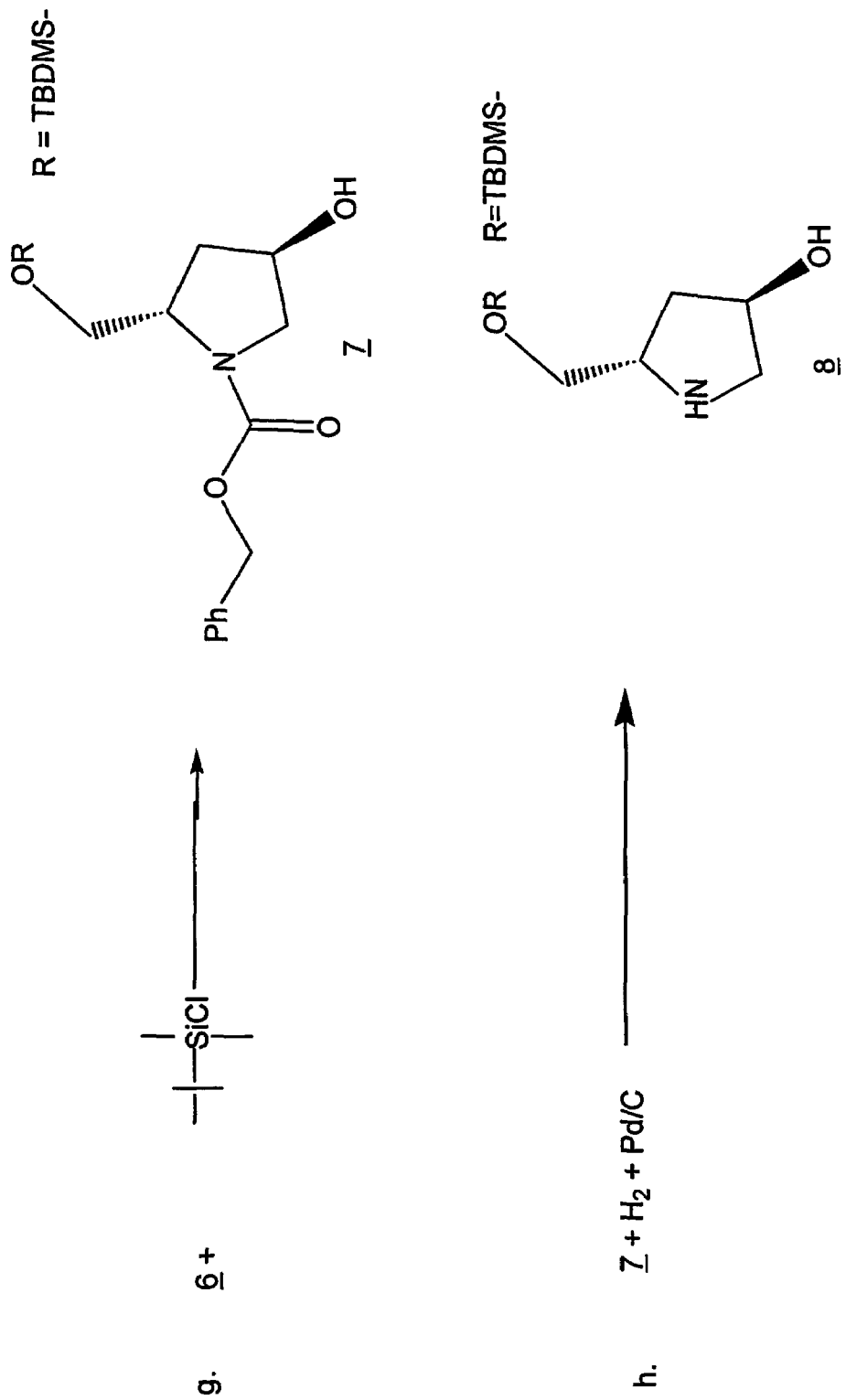
FIG. 1C depicts a reaction scheme illustrating steps (g)-(h) for preparing a compound in accordance with an embodiment of the invention.
Figure 1D:
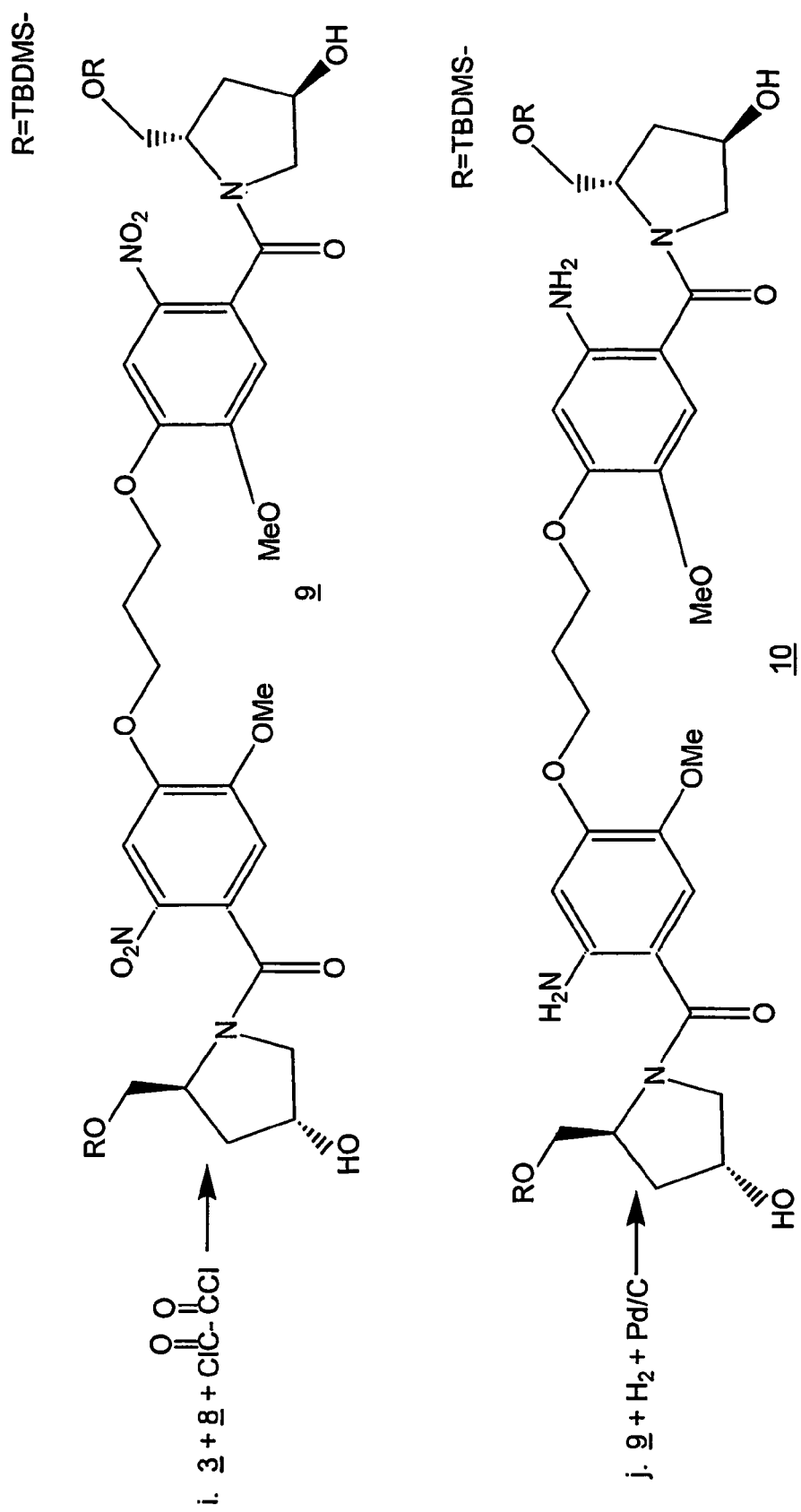
FIG. 1D depicts a reaction scheme illustrating steps (i)-(j) for preparing a compound in accordance with an embodiment of the invention.
Figure 1E:
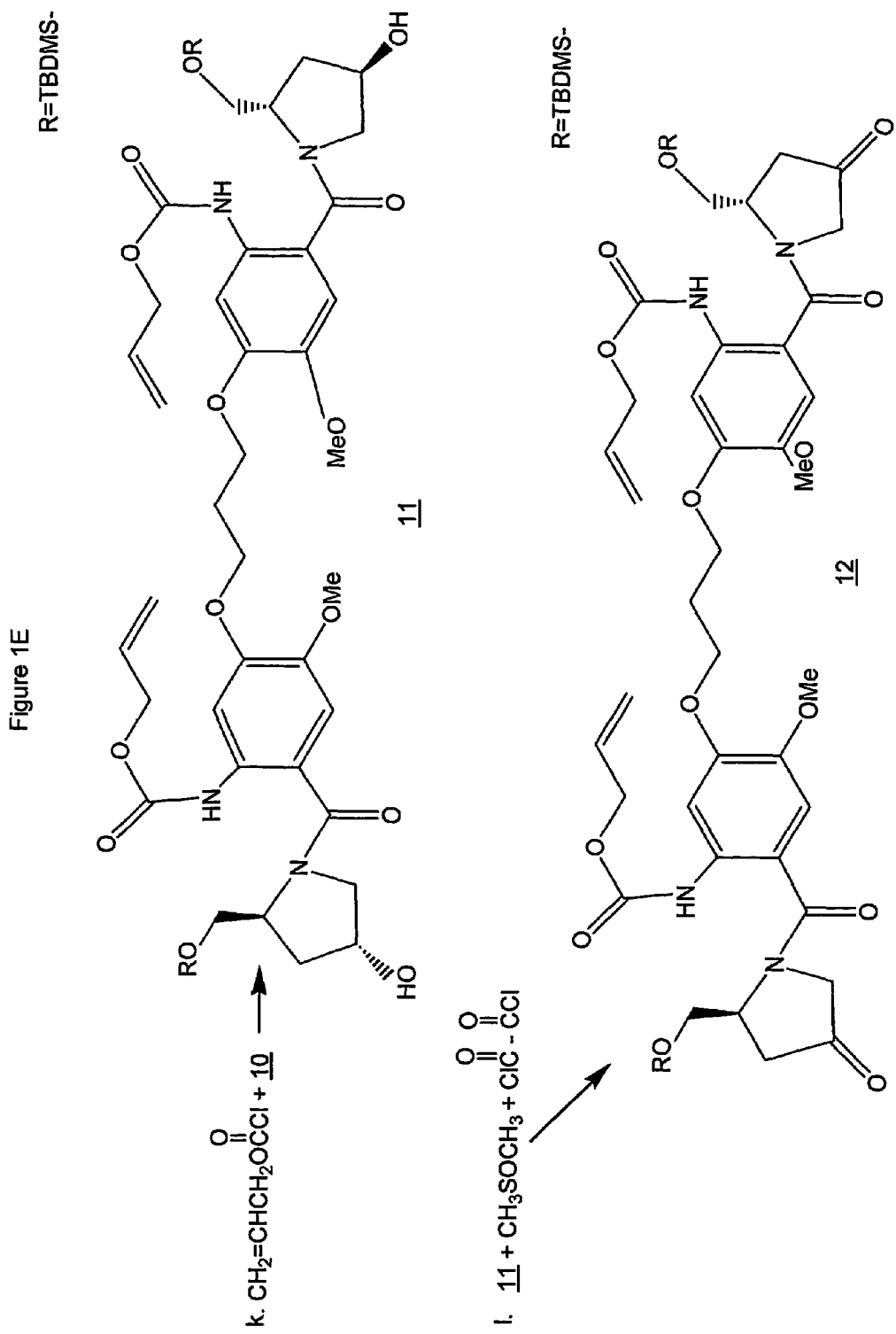
FIG. 1E depicts a reaction scheme illustrating steps (k)-(l) for preparing a compound in accordance with an embodiment of the invention.
Figure 1F:
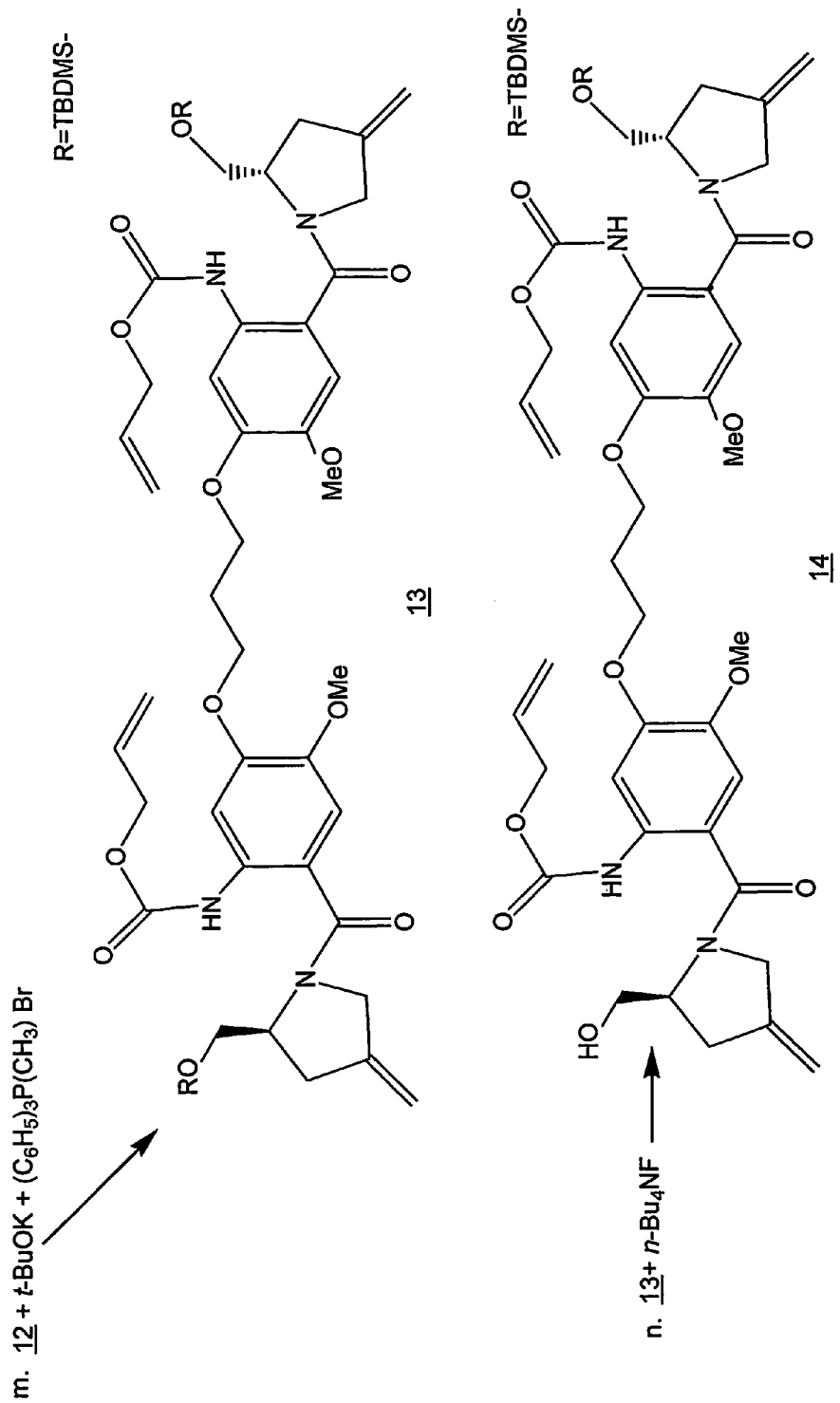
FIG. 1F depicts a reaction scheme illustrating steps (m)-(n) for preparing a compound in accordance with an embodiment of the invention.
Figure 1G:
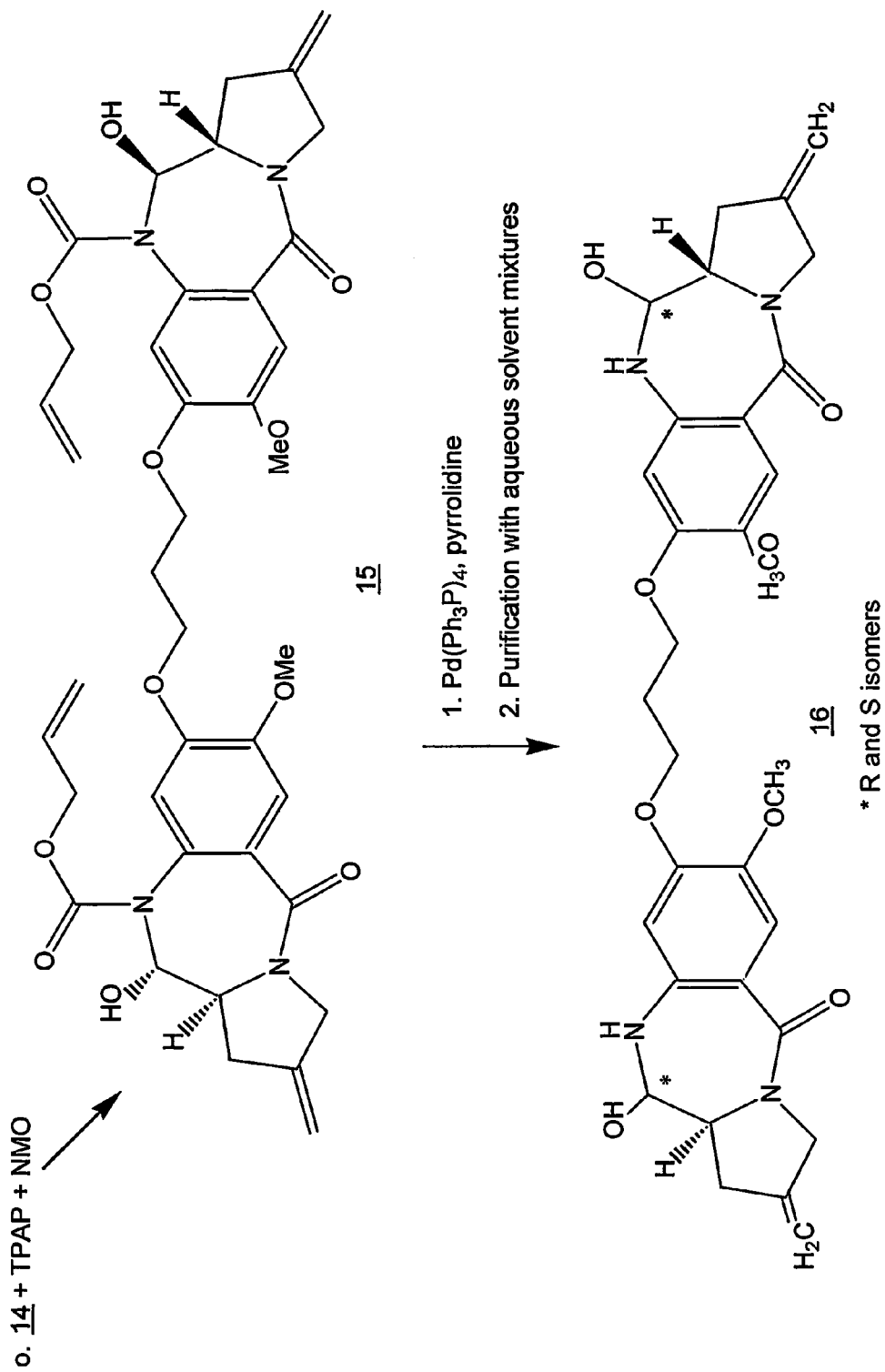
FIG. 1G depicts a reaction scheme illustrating step (o) for preparing a compound in accordance with an embodiment of the invention.

The invention provides a compound of Formula I:

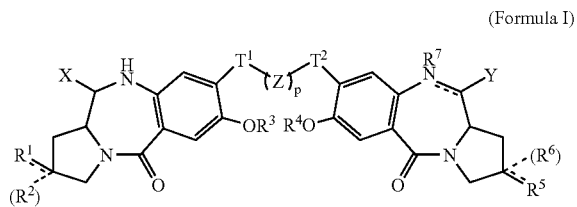

(Formula I)

wherein X is a substituent selected from the group consisting of an OH, an ether, a silyl ether, a trialkyl silyl ether, an ester, a carbonate, a carbamate, a thiocarbamate, a cyclic carbamate, a cyclic thiocarbamate, an acetate, SH, a sulfide, a sulphoxide, a sulphone, a sulphite, a bisulphite, a sulphonamide, an amine, an amide, an azido, a cyano, a halo, a triphenylphosphonium, a silyl, a trialkyl silyl, an amino acid-derived group, and a phosphorus-containing group;

wherein the bond between the carbon to which Y is attached and the N of $NR^7$ to which the carbon is attached is a single bond or a double bond, wherein, when the bond is a double bond, $R^7$ is absent and Y is H, and, when the bond is a single bond, $R^7$ is H and Y is a substituent selected from the group defined for X, wherein Y is optionally the same as X;

wherein each of $T^1$ and $T^2$ is independently O, S, or $NR^8$;

wherein Z is a divalent radical of an alkane, an alkene, or an alkyne, any of which optionally contains a heteroatom or carbonyl and any of which is substituted or unsubstituted;

wherein p is an integer that is greater than or equal to 2;

wherein each of $R^3$, $R^4$, and $R^8$ is independently a hydrogen; a $C_1$-$C_{24}$ alkyl, $C_2$-$C_{24}$ alkenyl, or $C_2$-$C_{24}$ alkynyl optionally substituted with a group selected from the group consisting of an aryl, a heterocycle, and an amine; or an aryl optionally substituted with an alkyl, an aryl, an alkoxy, a halo, an amine, a hydroxy, or a trifluoromethyl;

wherein the bond between $R^1$ and the carbon to which $R^1$ is attached is a single bond or a double bond, wherein, when the bond is a double bond, $R^2$ is absent and $R^1$ is a divalent radical derived from an alkane, an aromatic hydrocarbon, or a heterocycle, and when the bond is a single bond, $R^1$ and $R^2$ are independently selected from the group consisting of H, $C_1$-$C_8$ alkyl, aryl, and a heterocycle; and wherein the bond between $R^5$ and the carbon to which $R^5$ is attached is a single bond or a double bond, wherein, when the bond is a double bond, $R^6$ is absent and $R^5$ is a divalent radical derived from an alkane, an aromatic hydrocarbon, or a heterocycle, and when the bond is a single bond, $R^5$ and $R^6$ are independently selected from the group consisting of H, $C_1$-$C_8$ alkyl, aryl, and a heterocycle; or a salt thereof; wherein the compound is a solid.

The compounds of the present invention can be synthesized, and, in embodiments, isolated or purified to any degree. For purposes of the invention, the term "isolated" as used herein is defined as having been removed from a natural environment. The term "purified" as used herein refers to having been increased in purity, wherein "purity" is a relative term, and not to be construed as absolute purity. The term "isolated" and "purified" do not necessarily imply 100% or complete isolation or purity. Rather, there are varying degrees of isolation or purity of which one of ordinary skill in the art recognizes as having a potential benefit or prophylactic or therapeutic effect. In this regard, the compounds of the invention can be of any level of isolation or purity. Preferably, the compounds of Formula I are substantially isolated or substantially pure, such that the compounds are substantially free of any impurities or any materials or agents that, for example, interfere with the activity of the compounds or make the compounds toxic. Desirably, the compounds of the invention have a purity of about 75% or more, more preferably about 80% or more (e.g., about 90% or more), or even about 95% or more (e.g., about 98% or more, or about 99% or more).

The term "alkyl" (alkane) refers to a straight-chain or branched-chain alkyl containing, e.g., from 1 to about 24 carbon atoms, from 1 to about 16 carbon atoms, or from 1 to about 8 carbon atoms. Examples of saturated alkyls include methyl, ethyl, propyl, isopropyl, n-butyl, sec-butyl, t-butyl, octyl, and the like. The alkyl groups can be optionally substituted, for example, with at least one substituent selected from the group consisting of a halogen, a nitro, an amino, a hydroxyl, an alkoxy, an aryloxy, an aralkoxy, an ester, an amide, a sulfhydryl, an alkyl sulfide, an aryl sulfide, an alkyl sulfoxide, an aryl sufoxide, an alkyl sulfonyl, an aryl sulfonyl, a keto, a thioketo, an alkyl, a cyano, and the like. The alkyl also can be a cycloalkyl, (e.g., cyclohexyl or cyclopentyl).

The term "alkenyl" (alkene) means a straight-chain or branched-chain alkenyl having one or more double bonds. An alkenyl can contain, e.g., from 2 to about 24 carbon atoms, from 2 to about 16 carbon atoms, from 2 to about 8 carbon atoms. Examples of alkenyls include vinyl, allyl, 1,4-butadienyl, isopropenyl, and the like. The term "alkynyl" (alkyne) means a straight-chain or branched-chain alkynyl having one or more triple bonds. An alkynyl can contain, e.g., from 2 to about 8 carbon atoms, or from 2 to about 6 carbon atoms. Examples of alkynyls include ethynyl, propynyl(propargyl), butynyl, and the like. The alkenyl and alkenyl groups can be optionally substituted, for example, with at least one substituent selected from the group consisting of a halogen, a nitro, an amino, a hydroxyl, an alkoxy, an aryloxy, an aralkoxy, an ester, an amide, a sulfhydryl, an alkyl sulfide, an aryl sulfide, an alkyl sulfoxide, an aryl sufoxide, an alkyl sulfonyl, an aryl sulfonyl, a keto, a thioketo, an alkyl, a cyano and the like.

The term "alkoxy" includes alkoxy groups containing, for example, from 2 to about 24 carbon atoms, from 2 to about 16 carbon atoms, or from 2 to about 8 carbon atoms. Examples of alkoxy substituents include, but are not limited to, methoxy, ethoxy, isopropoxy, butanoxy, and the like.

The term "alkylamino" includes monoalkylamino and dialkylamino. The term "monoalkylamino" means an amino, which is substituted with an alkyl as defined herein. Examples of monoalkylamino substituents include, but are not limited to, methylamino, ethylamino, isopropylamino, t-butylamino, and the like. The term "dialkylamino" means an amino, which is substituted with two alkyls as defined herein, which alkyls can be the same or different. Examples of dialkylamino substituents include dimethylamino, diethylamino, ethylisopropylamino, diisopropylamino, dibutylamino, and the like.

The term "halogen" or "halo" includes halogens such as, e.g., fluoro (F), chloro (Cl), bromo (Br), or iodo (I).

The term "aryl" means an aromatic ring, as commonly understood in the art, and includes monocyclic and polycyclic aromatics. The aryl substituent preferably comprises 6-14 carbon atoms in the carbocyclic skeleton thereof. Examples of aryl substituents include, but are not limited to, phenyl, naphthyl, biphenyl, anthracenyl and the like, which can be unsubstituted or optionally substituted with one or more substituents selected from the group consisting of a halogen, a saturated alkyl, an unsaturated alkyl, a hydroxyl, an alkoxy, an aryloxy, an aralkoxy, an ester, an amide, a sulfhydryl, an alkyl sulfide, an aryl sulfide, an alkyl sulfoxide, an aryl sulfoxide, an alkylsulfonyl, an arylsulfonyl, a keto, a thioketo, a cyano, a nitro, an amino, an alkylamino, a dialkylamino, and the like.

X of Formula I can be a nitrogen-containing group, such as an amine, an amide, a cyano, or a sulphonamide. Amines include $NH_2$, NHR, and NRR', wherein each of R and R' is independently selected from a group consisting of an alkyl as described herein; a cycloalkyl, a $C_2$-$C_{24}$ alkenyl; a cyclohexylalkyl(cyclohexanalkyl); a $C_3$-$C_{26}$ alkoxyacetyl; a group of structure:

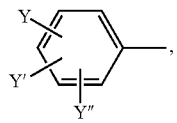

wherein each of Y and Y' is independently hydrogen, $C_1$-$C_{24}$ alkyl, aryl alkyl, $C_2$-$C_{24}$ alkenyl, $C_2$-$C_{24}$ alkynyl, $C_1$-$C_{24}$ alkoxy, or halogen, or Y and Y' together form 3,4-methylenedioxy, and Y" is hydrogen, $C_1$-$C_{24}$ alkyl, $C_1$-$C_{24}$ alkoxy or halogen; a naphthalenalkyl optionally substituted by methyl of halogen; aryl alkenyl, e.g., phenyl($C_2$-$C_{24}$ alkenyl), wherein the phenyl is optionally substituted with methyl or halogen; cinnamyl; heterocyclylalkyl, e.g., pyridinealkyl, optionally substituted with methyl or halogen; dihydropyridine alkyl optionally substituted with $C_1$-$C_{24}$ alkyl; thiophenealkyl optionally substituted with methyl or halogen; an aryl as discussed herein; an allyl; or furanalkyl optionally substituted with methyl or halogen.

Amines also include cyclic amines, such as piperidine or piperazine, or cyclic amines such that the compound of Formula I would, for example, contain a cyclic amine comprising N10 and C11 of Formula I. Amides include any group of the structure: —NHCOR, wherein R is defined as above for amines.

X of Formula I can be a sulfur-containing substituent, such as a sulphonamide, a sulfide, a sulphoxide, a sulphone, a sulphite, a bisulphate, a thiocarbamate, and a cyclic thiocarbamate. Sulphonamides include any group of structure: —NHSOOR, wherein R is defined as above for amines. Sulfides include any group of structure: —SR, wherein R is defined as above for amines, but R also can be cysteine or glutathione. Sulphoxides are any group of structure —SOR, wherein R is defined as above for amines. Sulphones include any group of structure —SOOR, wherein R is defined as above for amines. Sulphites have the structure —$SO_3$. Bisulphites have the structure: —$OSO_3$. Thiocarbamates include any group of structure —OCSNHR, wherein R is defined as above for amines. Cyclic thiocarbamates of Formula I can be formed, such that N10 and C11 are a part of the cyclic thiocarbamate.

X of Formula I can be any oxygen-containing substituent, such as an ether, a silyl ether, a trialkyl ether, an ester, a carbonate, a carbamate, a cyclic carbamate, or an acetate. Ethers include any group of structure: —OR, wherein R is defined as above for amines, but R can also be an arene, $CH_2X'R$, or $CH_2CH_2X'R$, wherein X' is N, S, or O. Silyl ethers have the formula —$OSiH_3$, whereas silyl trialkyl ethers have the formula —OSiRR'R", wherein each of R, R', and R" is independently any of the substituents defined for R of the amines. Esters (e.g., acetates) include any group of structure: —OCOR, wherein R is defined as above for amines. Carbonates include any group of structure —OCOOR, wherein R is defined as above for amines. Carbamates include any group of structure: —OCONHR, wherein R is as defined for amines. Cyclic carbamates of Formula I can be formed, such that N10 and C11 are part of the cyclic carbamate.

X of Formula I can be a halo, e.g., Cl, F, Br, I, and As, or each can be a triphenylphosphonium (—$P^+Ph_3$). Each of X and Y can independently be a silyl (—$SiH_3$) or a trialkylsilyl (—SiRR'R"), wherein each of R, R', and R" is independently an R as defined for amines.

X of Formula I can be an amino acid-derived group. The term "amino acid-derived group" as used herein refers to any substituent that is derived from an amino acid. Amino acid-derived groups include any group of structure:

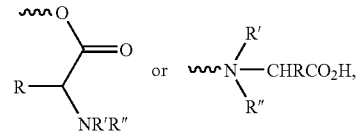

wherein each of R, R', and R" is independently selected from the group consisting of H; a $C_1$-$C_8$ alkyl optionally substituted by an amine or a carboxylate; an aryl; an arylalkyl; and a heterocycle. Preferably, each of R, R', and R" are, independently, H, $CH_3$, benzyl, $(CH_2)_4NH_2$, or $CH_2COOH$.

X of Formula I can be a phosphorus-containing group. The phosphorus-containing group can be a phosphoric group, a phosphorus group, a phosphonic acid group, or a phosphonous acid group. The phosphorus-containing group can have one of the following structures:

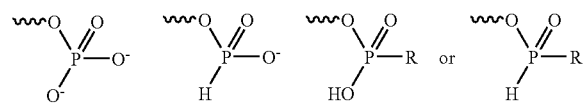

wherein R is $C_1$-$C_8$ alkyl optionally substituted by an aryl, a heterocycle, an alkoxy, a halo, an amine, or carboxylate; an aryl; or a heterocycle.

Exemplary substituent groups from which X of Formula I can be selected include:

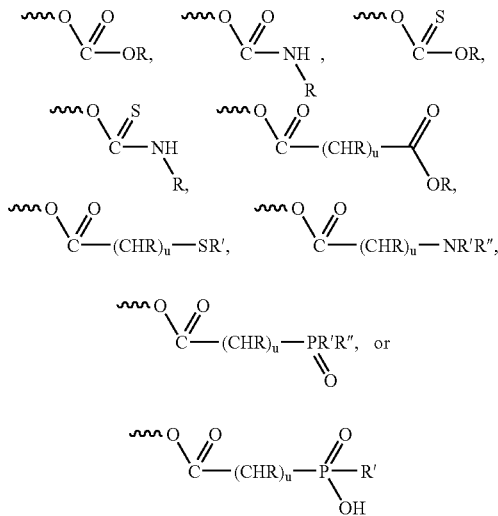

wherein each of R, R', and R" is independently selected from the group consisting of H; $C_1$-$C_8$ alkyl optionally substituted by an aryl, a heterocycle, an alkoxy, a halo, an amine, or carboxylate; an aryl; and a heterocycle, and wherein u is any integer, for example, from 1 to about 16, e.g. from 1 to about 12, from 1 to about 10, or from 1 to about 5.

X also can be an amide having the structure:

wherein each of R and R' is independently H; $C_1$-$C_8$ alkyl optionally substituted by an aryl, a heterocycle, an alkoxy, a halo, an amine, or carboxylate; an aryl; arylalkyl or a heterocycle.

X of Formula I can be a monohydroxylic group (e.g., an alcohol), or a polyhydroxylic group (e.g., a diol or polyol), such as a group derived from a sorbitol, a polyethylene glycol (PEG), a polymer, or a sugar. Exemplary such substituents have one of the following structures:

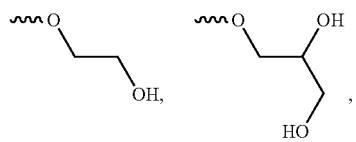

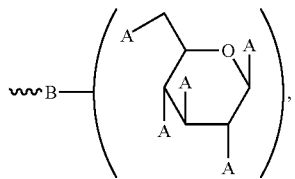

wherein B is O, B is attached to the cyclopentyloxy ring at any carbon of the ring, at the carbon to which B is attached, A is H, and, at the other carbons in the cyclopentyloxy ring (at the carbons where B is not attached to the ring), A is —OH; or

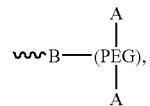

wherein B is O, B is attached to any carbon of PEG, at the carbon to which B is attached, A is H, and, at the other carbons of PEG (at the carbons where B is not attached to PEG), A is —OH.

Y of Formula I can be any of the substituents described herein as suitable for X, and can be the same as or different from X. Preferably, Y is the same as X.

Preferred compounds of the invention include those in which each of X and Y of Formula I is OH, or X is OH and Y is H. Other preferred compounds include those in which each of X and Y is OR, or X is OR and Y is H, wherein in R is preferably an alkyl, such as a $C_1$-$C_8$ alkyl (e.g., methyl, propyl, isopropyl, butyl, or t-butyl).

Each of $T^1$ and $T^2$ of Formula I is independently O, S, or $NR^8$. Preferably, each of $T^1$ and $T^2$ is O, p is 3-5 (more preferably p is 3), and Z is —$CH_2$—. When either or both of $T^1$ and $T^2$ are $NR^8$, $R^8$ is preferably H. Also preferred is that each of $R^3$ and $R^4$ is a $C_1$-$C_8$ alkyl, more preferably $CH_3$. Desirably, the bond between $R^1$ and the carbon to which $R^1$ is attached is a double bond and $R^1$ is a divalent radical derived from an alkane, an aromatic hydrocarbon, or a heterocycle. More preferably, $R^1$ is a divalent radical derived from an alkane, such as a $C_1$-$C_8$ alkane (e.g., $CH_2$). It is similarly preferred that the bond between $R^5$ and the carbon to which $R^5$ is attached is a double bond and $R^5$ is a divalent radical derived from an alkane, an aromatic hydrocarbon, or a heterocycle. More preferably, $R^5$ is a divalent radical derived from an alkane, such as a $C_1$-$C_8$ alkane (e.g., $CH_2$).

Preferred compounds of Formula I include:

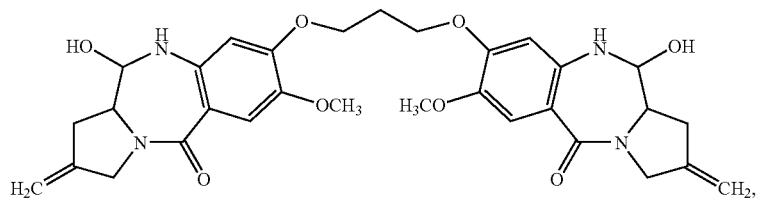

-continued

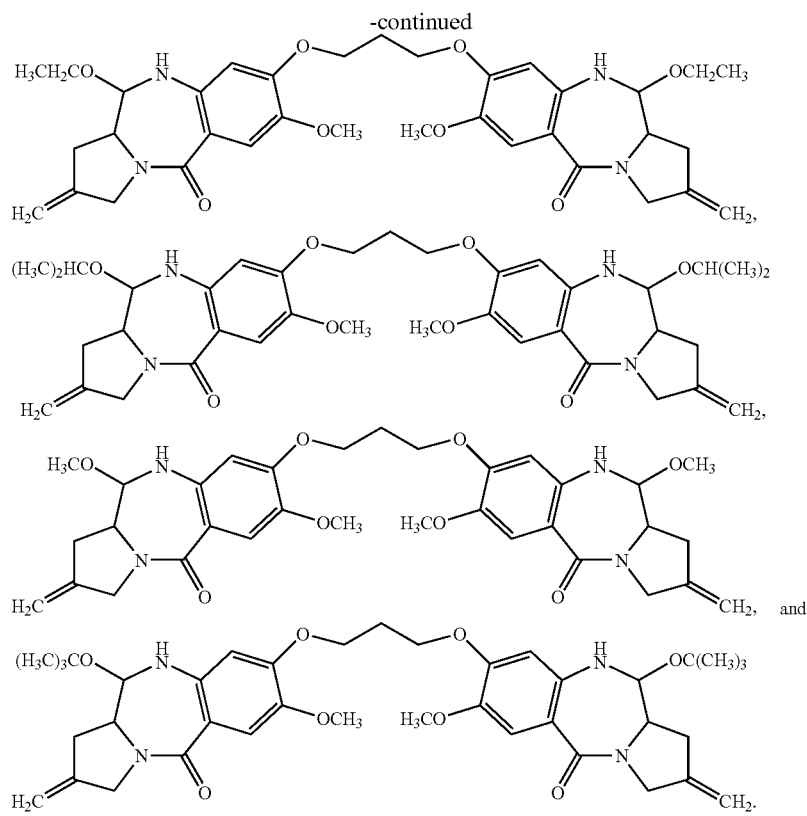

Other preferred compounds of Formula I include

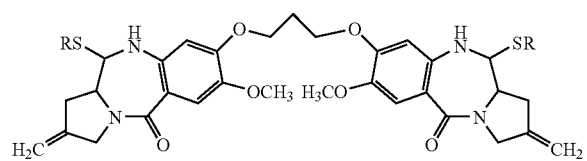

wherein R is an alkyl; a $C_2$-$C_{24}$ alkenyl; $C_2$-$C_{24}$ alkynyl; a cyclohexylalkyl; a $C_3$-$C_{26}$ alkoxyacetyl; a naphthalenalkyl optionally substituted with methyl or halogen; a phenyl($C_2$-$C_{24}$ alkenyl), wherein the phenyl is optionally substituted with methyl or halogen; a cinnamyl; a pyridinealkyl optionally substituted with methyl or halogen; a dihydropyridine alkyl optionally substituted with $C_1$-$C_{24}$ alkyl; a thiophenealkyl optionally substituted with methyl or halogen; an aryl; an allyl; a furanalkyl optionally substituted with methyl or halogen; cysteine; glutathione; or a group of structure

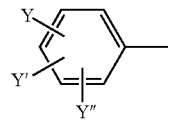

wherein each of Y and Y' is independently hydrogen, $C_1$-$C_{24}$ alkyl, $C_1$-$C_{24}$ alkoxy, or halogen, or Y and Y' together form 3,4-methylenedioxy, and Y" is hydrogen, $C_1$-$C_{24}$ alkyl, $C_1$-$C_{24}$ alkoxy or halogen. Preferably, R is a group of structure

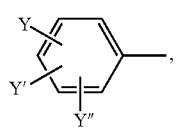

wherein each of Y and Y' is independently hydrogen, $C_1$-$C_8$ alkyl, $C_1$-$C_8$ alkoxy, or halogen, or Y and Y' together form 3,4-methylenedioxy, and Y" is hydrogen, $C_1$-$C_8$ alkyl, $C_1$-$C_8$ alkoxy or halogen. More preferably, Y and Y' are hydrogen, and Y" is hydrogen, a $C_1$-$C_8$ alkyl, especially methyl, ethyl, propyl, isopropyl, butyl, or t-butyl, or a $C_1$-$C_8$ alkoxy, especially methoxy, propoxy, or butoxy.

Still other preferred compounds of Formula I include

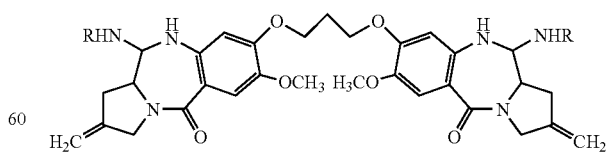

wherein R is an alkyl; a $C_2$-$C_{24}$ alkenyl; a cyclohexylalkyl; a $C_3$-$C_{26}$ alkoxyacetyl; a naphthalenalkyl optionally substituted with methyl or halogen; phenyl($C_2$-$C_{24}$ alkenyl), wherein the phenyl is optionally substituted with methyl or halogen; cinnamyl; pyridinealkyl optionally substituted with methyl or halogen; dihydropyridine alkyl optionally substituted with $C_1$-$C_{24}$ alkyl; thiophenealkyl optionally substituted with methyl or halogen; an aryl; an allyl; furanalkyl optionally substituted with methyl or halogen; or a group of structure

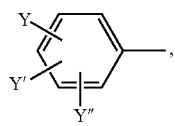

wherein each of Y and Y' is independently hydrogen, $C_1$-$C_{24}$ alkyl, $C_1$-$C_{24}$ alkoxy, or halogen, or Y and Y' together form 3,4-methylenedioxy, and Y" is hydrogen, $C_1$-$C_{24}$ alkyl, $C_1$-$C_{24}$ alkoxy or halogen. Preferably, R is a group of structure

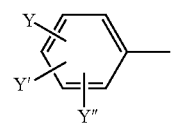

wherein each of Y and Y' is independently hydrogen, $C_1$-$C_8$ alkyl, $C_1$-$C_8$ alkoxy, or halogen, or Y and Y' together form 3,4-methylenedioxy, and Y" is hydrogen, $C_1$-$C_8$ alkyl, $C_1$-$C_8$ alkoxy or halogen. More preferably, Y and Y' are hydrogen, and Y" is hydrogen, a $C_1$-$C_8$ alkyl, especially methyl, ethyl, propyl, isopropyl, butyl, or t-butyl, or a $C_1$-$C_8$ alkoxy, especially methoxy, propoxy, or butoxy.

The compounds of Formula I of the present inventive methods can be in the form of a salt, which is preferably a pharmaceutically acceptable salt. Suitable pharmaceutically acceptable acid addition salts include those derived from non-toxic organic or inorganic acid addition salt of the base compounds. Illustrative inorganic acids which form suitable salts include hydrochloric, hydrobromic, sulfuric, phosphoric acids, metaphosphoric, and nitric acids and acid metal salts, such as sodium monohydrogen orthophosphate and postassium hydrogen sulfate. Illustrative organic acids which form suitable salts include the mono, di, and tricarboxylic acids. Illustrative of such acids are, for instance, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, and 2-phenoxybenzoic acids. Other organic acids which form suitable salts are the sulfonic acids (e.g., methane sulfonic acid), gluconic, arylsulphonic acids (e.g., p-toluenesulphonic acid), and 2-hydroxyethane sulfonic acid. These salts and base compounds can exist in either a hydrated or a substantially anhydrous form. The acid salts can be prepared by standard techniques, such as by dissolving the free base in aqueous or aqueous-alcohol solution or other suitable solvent containing the appropriate acid and isolating, e.g., by evaporating the solution, or by reacting the free base in an organic solvent in which case the salt can separate directly or can be obtained by concentration of the solution. Preferably, the acid addition salts of the compounds of this invention are crystalline materials, which are soluble in water and various hydrophilic organic solvents and which in comparison to their free base forms, demonstrate higher melting points and an increased stability.

According to the foregoing aspect of the invention, the compound of Formula I is a solid. However, according to the related aspects of the invention described below, the compound of Formula I can be a liquid or a solid. Nevertheless, according to any aspect of the invention, the compound of Formula I is preferably a solid, e.g., a crystalline solid. By "solid," it is meant that the compound is a solid at room temperature (e.g., about 20-25° C.). The compound of Formula I can be of any stereochemistry. Preferably, the compound of Formula I has the S stereochemistry at the C11a position, C11'a position, or at both positions.

In a first related aspect, the invention provides a compound of Formula I:

(Formula I)

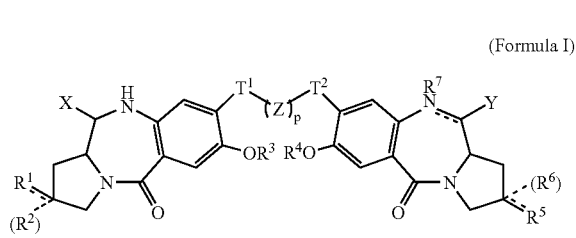

wherein X is a substituent selected from the group consisting of an OH, an ether, a silyl ether, a trialkyl silyl ether, an ester, a carbonate, a carbamate, a thiocarbamate, a cyclic carbamate, a cyclic thiocarbamate, an acetate, SH, a sulfide, a sulphoxide, a sulphone, a sulphite, a bisulphite, a sulphonamide, an amine, an amide, an azido, a cyano, a halo, a triphenylphosphonium, a silyl, a trialkyl silyl, an amino acid-derived group, and a phosphorus-containing group;

wherein the bond between the carbon to which Y is attached and the N of $NR^7$ to which the carbon is attached is a single bond or a double bond, wherein, when the bond is a double bond, $R^7$ is absent and Y is H, and, when the bond is a single bond, $R^7$ is H and Y is a substituent selected from the group defined for X, wherein Y is optionally the same as X;

wherein each of $T^1$ and $T^2$ is independently O, S, or $NR^8$;

wherein Z is a divalent radical of an alkane, an alkene, or an alkyne, any of which optionally contains a heteroatom or carbonyl and any of which is substituted or unsubstituted;

wherein p is an integer that is greater than or equal to 2;

wherein each of $R^3$, $R^4$, $R^8$ is independently a hydrogen; a $C_1$-$C_{24}$ alkyl, $C_2$-$C_{24}$ alkenyl, or $C_2$-$C_{24}$ alkyl optionally substituted with a group selected from the group consisting of an aryl, a heterocycle, and an amine; or an aryl optionally substituted with an alkyl, an aryl, an alkoxy, a halo, an amine, a hydroxy, or a trifluoromethyl;

wherein the bond between $R^1$ and the carbon to which $R^1$ is attached is a single bond or a double bond, wherein, when the bond is a double bond, $R^2$ is absent and $R^1$ is a divalent radical derived from an alkane, an aromatic hydrocarbon, or a heterocycle, and when the bond is a single bond, $R^1$ and $R^2$ are independently selected from the group consisting of H, $C_1$-$C_8$ alkyl, aryl, and a heterocycle; and wherein the bond between $R^5$ and the carbon to which $R^5$ is attached is a single bond or a double bond, wherein, when the bond is a double bond, $R^6$ is absent and $R^5$ is a divalent radical derived from an alkane, an aromatic hydrocarbon, or a heterocycle, and when the bond is a single bond, $R^5$ and $R^6$ are independently selected from the group consisting of H, $C_1$-$C_8$ alkyl, aryl, and a heterocycle; or a salt thereof;

provided that, when each of $R^1$ and $R^5$ is $CH_2$ attached by a double-bond, $R^2$ and $R^6$ are absent, $R^3$ and $R^4$ are $CH_3$, $R^7$ is H, $T^1$ and $T^2$ are both O, Z is $CH_2$, and p is 3, then X and Y are not both methoxy, both ethoxy, or both hydroxyl; and when each of $R^1$, $R^2$, $R^5$, and $R^6$ are H, then X and Y are not both sulfide or both ether.

In another related aspect, the invention provides a compound of Formula I:

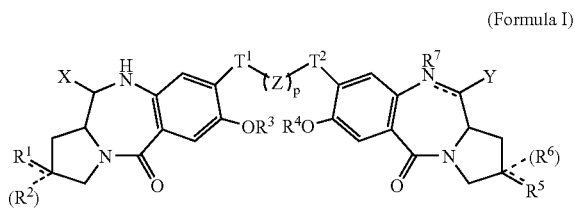

(Formula I)

wherein X is a substituent selected from the group consisting of a silyl ether, a trialkyl silyl ether, an ester, a carbonate, a carbamate, a thiocarbamate, a cyclic carbamate, a cyclic thiocarbamate, an acetate, SH, a sulfide, a sulphoxide, a sulphone, a sulphite, a bisulphite, a sulphonamide, an amine, an amide, an azido, a cyano, a halo, a triphenylphosphonium, a silyl, a trialkyl silyl, an amino acid-derived group, and a phosphorus-containing group;

wherein the bond between the carbon to which Y is attached and the N of $NR^7$ to which the carbon is attached is a single bond or a double bond, wherein, when the bond is a double bond, $R^7$ is absent and Y is H, and, when the bond is a single bond, $R^7$ is H and Y is a substituent selected from the group defined for X, wherein Y is optionally the same as X;

wherein each of $T^1$ and $T^2$ is independently O, S, or $NR^8$;

wherein Z is a divalent radical of an alkane, an alkene, or an alkyne, any of which optionally contains a heteroatom or carbonyl and any of which is substituted or unsubstituted;

wherein p is an integer that is greater than or equal to 2;

wherein each of $R^3$, $R^4$, and $R^8$ is independently a hydrogen; a $C_1$-$C_{24}$ alkyl, $C_2$-$C_{24}$ alkenyl, or $C_2$-$C_{24}$ alkynyl, optionally substituted with a group selected from the group consisting of an aryl, a heterocycle, and an amine; or an aryl optionally substituted with an alkyl, an aryl, an alkoxy, a halo, an amine, a hydroxy, or a trifluoromethyl;

wherein the bond between $R^1$ and the carbon to which $R^1$ is attached is a single bond or a double bond, wherein, when the bond is a double bond, $R^2$ is absent and $R^1$ is a divalent radical derived from an alkane, an aromatic hydrocarbon, or a heterocycle, and when the bond is a single bond, $R^1$ and $R^2$ are independently selected from the group consisting of a $C_1$-$C_8$ alkyl, an aryl, and a heterocycle; and wherein the bond between $R^5$ and the carbon to which $R^5$ is attached is a single bond or a double bond, wherein, when the bond is a double bond, $R^6$ is absent and $R^5$ is a divalent radical derived from an alkane, an aromatic hydrocarbon, or a heterocycle, and when the bond is a single bond, $R^5$ and $R^6$ are independently selected from the group consisting of $C_1$-$C_8$ alkyl, aryl, and a heterocycle; or a salt thereof.

The compounds described above can be prepared by any suitable method. In embodiments, the compounds of Formula I described herein can be synthesized by the methods described in the Examples or other similar methods. In this regard, the invention also provides a method of preparing a compound of Formula I:

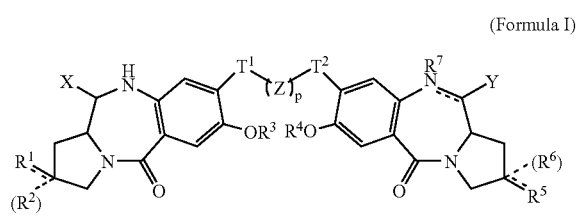

(Formula I)

wherein X is OH, wherein the bond between the carbon to which Y is attached and the N of $NR^7$ to which the carbon is attached is a single bond or a double bond, wherein, when the bond is a double bond, $R^7$ is absent and Y is H, and, when the bond is a single bond, $R^7$ is H and Y is OH;

wherein each of $T^1$ and $T^2$ is independently O, S, or $NR^8$;

wherein Z is a divalent radical of an alkane, an alkene, or an alkyne, any of which optionally contains a heteroatom or carbonyl and any of which is substituted or unsubstituted;

wherein p is an integer that is greater than or equal to 2;

wherein each of $R^3$, $R^4$, and $R^8$ is independently a hydrogen; a $C_1$-$C_{24}$ alkyl, $C_2$-$C_{24}$ alkenyl, or $C_2$-$C_{24}$ alkynyl, optionally substituted with a group selected from the group consisting of an aryl, a heterocycle, and an amine; or an aryl optionally substituted with an alkyl, an aryl, an alkoxy, a halo, an amine, a hydroxy, or a trifluoromethyl;

wherein the bond between $R^1$ and the carbon to which $R^1$ is attached is a single bond or a double bond, wherein, when the bond is a double bond, $R^2$ is absent and $R^1$ is a divalent radical derived from an alkane, an aromatic hydrocarbon, or a heterocycle, and when the bond is a single bond, $R^1$ and $R^2$ are independently selected from the group consisting of H, $C_1$-$C_8$ alkyl, aryl, and a heterocycle; and wherein the bond between $R^5$ and the carbon to which $R^5$ is attached is a single bond or a double bond, wherein, when the bond is a double bond, $R^6$ is absent and $R^5$ is a divalent radical derived from an alkane, an aromatic hydrocarbon, or a heterocycle, and when the bond is a single bond, $R^5$ and $R^6$ are independently selected from the group consisting of H, $C_1$-$C_8$ alkyl, aryl, and a heterocycle;

or a salt thereof; and wherein the compound is a solid;

which method comprises: (a) providing a compound of Formula II:

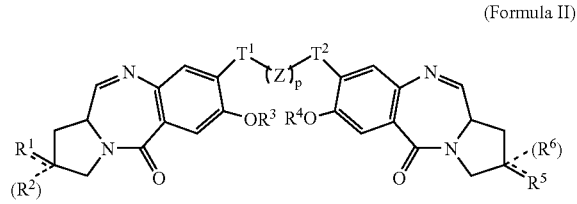

(Formula II)

wherein the definitions of $R^1$, $R^2$, $R^3$, $R^4$, $R^5$, $R^6$, $T^1$, $T^2$, Z, and p are the same as those for Formula I; and (b) contacting the compound of Formula II with water, whereby a solid compound of Formula I is formed.

Preferably, the method comprises contacting the compound of Formula II with water in a solvent system, wherein the solvent system comprises an organic solvent, such as a water-miscible aprotic solvent, and water. The solvent system can comprise any suitable amount of water. Preferably, the solvent system comprises at least 10% (v/v) water. More preferably, the solvent system comprises at least 30% (v/v) water. Most preferably, the solvent system comprises at least 40% (v/v) water.

The organic solvent can be any water-miscible organic solvent, preferably a water-miscible aprotic organic solvent, such as acetonitrile, THF, DMA, DMSO, and the like. Preferably, the organic solvent is acetonitrile.

Methods of obtaining a compound of Formula II suitable for use in the method of the invention are known in the art (see, for instance, Gregson et al., *J. Med. Chem.* 44: 737-748 (2001); see also Example 1 herein). The compound of Formula II can be contacted with water by any suitable method. For example, the compound of Formula II can be mixed with water or a water-containing solvent system, or the compound of Formula II can be sprayed with water or water vapor.

In a related aspect, the invention provides a method of preparing a compound of Formula I:

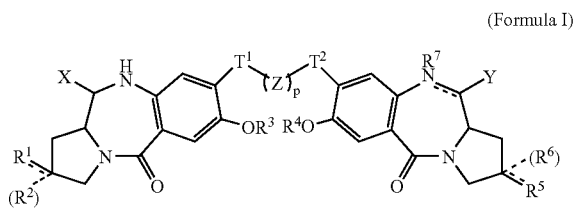

(Formula I)

wherein X is a substituent selected from the group consisting of an ether, a silyl ether, a trialkyl silyl ether, an ester, a carbonate, a carbamate, a thiocarbamate, a cyclic carbamate, a cyclic thiocarbamate, an acetate, SH, a sulfide, a sulphoxide, a sulphone, a sulphite, a bisulphite, a sulphonamide, an amine, an amide, an azido, a cyano, a halo, a triphenylphosphonium, a silyl, a trialkyl silyl, an amino acid-derived group, and a phosphorus-containing group;

wherein the bond between the carbon to which Y is attached and the N of $NR^7$ to which the carbon is attached is a single bond or a double bond, wherein, when the bond is a double bond, $R^7$ is absent and Y is H, and, when the bond is a single bond, $R^7$ is H and Y is a substituent selected from the group defined for X, wherein Y is optionally the same as X;

wherein each of $T^1$ and $T^2$ is independently O, S, or $NR^8$;

wherein Z is a divalent radical of an alkane, an alkene, or an alkyne, any of which optionally contains a heteroatom or carbonyl and any of which is substituted or unsubstituted;

wherein p is an integer that is greater than or equal to 2;

wherein each of $R^3$, $R^4$, and $R^8$ is independently a hydrogen; a $C_1$-$C_{24}$ alkyl, $C_2$-$C_{24}$ alkenyl, or $C_2$-$C_{24}$ alkynyl optionally substituted with a group selected from the group consisting of an aryl, a heterocycle, and an amine; or an aryl optionally substituted with an alkyl, an aryl, an alkoxy, a halo, an amine, a hydroxy, or a trifluoromethyl;

wherein the bond between $R^1$ and the carbon to which $R^1$ is attached is a single bond or a double bond, wherein, when the bond is a double bond, $R^2$ is absent and $R^1$ is a divalent radical derived from an alkane, an aromatic hydrocarbon, or a heterocycle, and when the bond is a single bond, $R^1$ and $R^2$ are independently selected from the group consisting of H, $C_1$-$C_8$ alkyl, aryl, and a heterocycle; and wherein the bond between $R^5$ and the carbon to which $R^5$ is attached is a single bond or a double bond, wherein, when the bond is a double bond, $R^6$ is absent and $R^5$ is a divalent radical derived from an alkane, an aromatic hydrocarbon, or a heterocycle, and when the bond is a single bond, $R^5$ and $R^6$ are independently selected from the group consisting of H, $C_1$-$C_8$ alkyl, aryl, and a heterocycle;

or a salt thereof; and wherein the compound is a solid.

which method comprises: (a) providing a compound of Formula II:

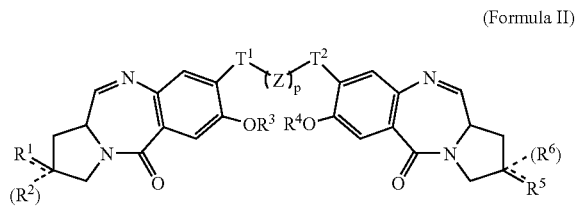

(Formula II)

wherein the definitions of $R^1$, $R^2$, $R^3$, $R^4$, $R^5$, $R^6$, $T^1$, $T^2$, Z, and p are the same as those for Formula I; and (b) combining the compound of Formula II with a nucleophilic organic reactant, e.g., wherein the nucleophilic part of the nucleophilic organic reactant provides X, whereby a solid compound of Formula I is formed.

In another aspect, the invention provides a method of preparing a compound of Formula I:

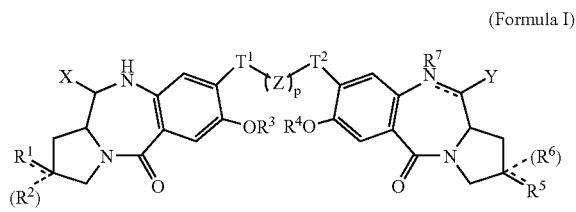

(Formula I)

wherein X is a substituent selected from the group consisting of an OH, an ether, a silyl ether, a trialkyl silyl ether, an ester, a carbonate, a carbamate, a thiocarbamate, a cyclic carbamate, a cyclic thiocarbamate, an acetate, SH, a sulfide, a sulphoxide, a sulphone, a sulphite, a bisulphite, a sulphonamide, an amine, an amide, an azido, a cyano, a halo, a triphenylphosphonium, a silyl, a trialkyl silyl, an amino acid-derived group, and a phosphorus-containing group;

wherein the bond between the carbon to which Y is attached and the N of $NR^7$ to which the carbon is attached is a single bond or a double bond, wherein, when the bond is a double bond, $R^7$ is absent and Y is H, and, when the bond is a single bond, $R^7$ is H and Y is a substituent selected from the group defined for X, wherein Y is optionally the same as X;

wherein each of $T^1$ and $T^2$ is independently O, S, or $NR^8$;

wherein Z is a divalent radical of an alkane, an alkene, or an alkyne, any of which optionally contains a heteroatom or carbonyl and any of which is substituted or unsubstituted;

wherein p is an integer that is greater than or equal to 2;

wherein each of $R^3$, $R^4$, and $R^8$ is independently a hydrogen; a $C_1$-$C_{24}$ alkyl, $C_2$-$C_{24}$ alkenyl, or $C_2$-$C_{24}$ alkynyl, optionally substituted with a group selected from the group consisting of an aryl, a heterocycle, and an amine; or an aryl optionally substituted with an alkyl, an aryl, an alkoxy, a halo, an amine, a hydroxy, or a trifluoromethyl;

wherein the bond between $R^1$ and the carbon to which $R^1$ is attached is a single bond or a double bond, wherein, when the bond is a double bond, $R^2$ is absent and $R^1$ is a divalent radical derived from an alkane, an aromatic hydrocarbon, or a heterocycle, and when the bond is a single bond, $R^1$ and $R^2$ are independently selected from the group consisting of H, $C_1$-$C_8$ alkyl, aryl, and a heterocycle; and wherein the bond between $R^5$ and the carbon to which $R^5$ is attached is a single bond or a double bond, wherein, when the bond is a double bond, $R^6$ is absent and $R^5$ is a divalent radical derived from an alkane, an aromatic hydrocarbon, or a heterocycle, and when the bond is a single bond, $R^5$ and $R^6$ are independently selected from the group consisting of H, $C_1$-$C_8$ alkyl, aryl, and a heterocycle;

or a salt thereof; and provided that, when each of $R^1$ and $R^5$ is $CH_2$ attached by a double-bond, $R^2$ and $R^6$ are absent, $R^3$ and $R^4$ are $CH_3$, $R^7$ is H, $T^1$ and $T^2$ are both O, Z is $CH_2$, and p is 3, then X and Y are not both methoxy, both ethoxy, or both hydroxyl; and when each of $R^1$, $R^2$, $R^5$, and $R^6$ are H, then X and Y are not both sulfide or both ether;

which method comprises: (a) providing a compound of Formula II:

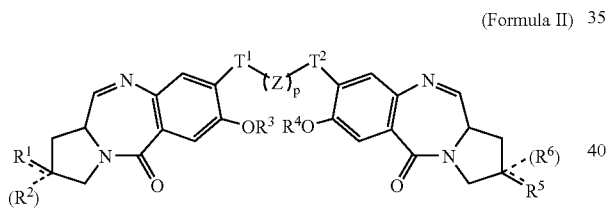

(Formula II)

wherein the definitions of $R^1$, $R^2$, $R^3$, $R^4$, $R^5$, $R^6$, $T^1$, $T^2$, Z, and p are the same as those for Formula I; and (b) combining the compound of Formula II with a nucleophilic organic reactant, e.g., wherein the nucleophilic part of the nucleophilic organic reactant provides X, whereby the solid compound of Formula I is formed.

The invention further provides a) method of preparing a compound of Formula I:

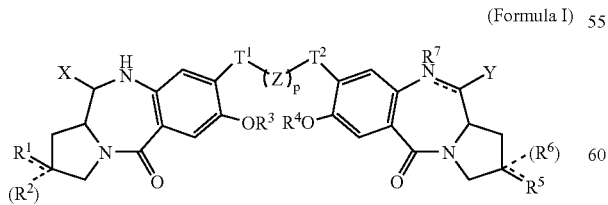

(Formula I)

wherein X is a substituent selected from the group consisting of a silyl ether, a trialkyl silyl ether, an ester, a carbonate, a carbamate, a thiocarbamate, a cyclic carbamate, a cyclic thiocarbamate, an acetate, SH, a sulfide, a sulphoxide, a sulphone, a sulphite, a bisulphite, a sulphonamide, an amine, an amide, an azido, a cyano, a halo, a triphenylphosphonium, a silyl, a trialkyl silyl, an amino acid-derived group, and a phosphorus-containing group;

wherein the bond between the carbon to which Y is attached and the N of $NR^7$ to which the carbon is attached is a single bond or a double bond, wherein, when the bond is a double bond, $R^7$ is absent and Y is H, and, when the bond is a single bond, $R^7$ is H and Y is a substituent selected from the group defined for X, wherein Y is optionally the same as X;

wherein each of $T^1$ and $T^2$ is independently O, S, or $NR^8$;

wherein Z is a divalent radical of an alkane, an alkene, or an alkyne, any of which optionally contains a heteroatom or carbonyl and any of which is substituted or unsubstituted, wherein p is an integer that is greater than or equal to 2;

wherein each of $R^3$, $R^4$, and $R^8$ is independently a hydrogen; a $C_1$-$C_{24}$ alkyl, $C_2$-$C_{24}$ alkenyl, or $C_2$-$C_{24}$ alkynyl, optionally substituted with a group selected from the group consisting of an aryl, a heterocycle, H, and an amine; or an aryl optionally substituted with an alkyl, an aryl, an alkoxy, a halo, an amine, a hydroxy, or a trifluoromethyl;

wherein the bond between $R^1$ and the carbon to which $R^1$ is attached is a single bond or a double bond, wherein, when the bond is a double bond, $R^2$ is absent and $R^1$ is a divalent radical derived from an alkane, an aromatic hydrocarbon, or a heterocycle, and when the bond is a single bond, $R^1$ and $R^2$ are independently selected from the group consisting of $C_1$-$C_8$ alkyl, aryl, and a heterocycle; and wherein the bond between $R^5$ and the carbon to which $R^5$ is attached is a single bond or a double bond, wherein, when the bond is a double bond, $R^6$ is absent and $R^5$ is a divalent radical derived from an alkane, an aromatic hydrocarbon, or a heterocycle, and when the bond is a single bond, $R^5$ and $R^6$ are independently selected from the group consisting of $C_1$-$C_8$ alkyl, aryl, and a heterocycle;

or a salt thereof; and which method comprises: (a) providing a compound of Formula II:

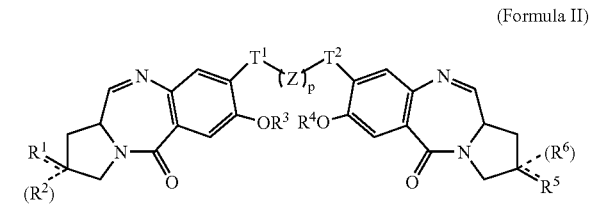

(Formula II)

wherein the definitions of $R^1$, $R^2$, $R^3$, $R^4$, $R^5$, $R^6$, $T^1$, $T^2$, Z, and p are the same as those for Formula I; and (b) combining the compound of Formula II with a nucleophilic reactant, e.g., wherein the nucleophilic part of the nucleophilic organic reactant provides X, and whereby the solid compound of Formula I is formed.

Suitable nucleophilic reactants for use in conjunction with the invention include any reactant comprising a nucleophilic part capable of nucleophilic addition to the N10-C11 position of the compound of Formula I to provide the desired substituent at position X. Of course, the choice of any particular nucleophilic organic reactant will depend upon the desired substituent. Preferred nucleophilic reactants include alcohols (e.g., methanol, ethanol, n-propanol, isopropanol, t-butanol, etc.), thiols, such as aryl thiols (e.g., thiophenol and alkylthiophenol), and amines, such as alkyl amines (e.g., t-butylamine). The compound of Formula I can be combined with the nucleophilic organic reactant by any suitable method, such as by mixing.

Preferred methods for preparing a compound of Formula I provide the compound as a solid. Accordingly, any of the methods provided herein may further comprise a step by which the compound of Formula I is precipitated from the solvent or reactant (e.g., water, water/solvent mixture, or nucleophilic organic reactant).

The methods for preparing a compound of Formula I also can comprise isolating the compound of Formula I from any excess solvent or reactant that may be present. Isolation of the solid compound of Formula I can be performed using any suitable method. When the compound of Formula I is a solid, it is preferred that the compound is isolated by evaporating the excess solvent or reactant, such as by applying a vacuum.

The compounds of Formula I are useful in a number of methods. For example, the compounds can be used to regulate gene expression, e.g., regulate transcription. In particular, the compounds can be used to inhibit gene expression. Without being bound to any particular theory, the compounds of Formula I are believed to have the ability to bind irreversibly to DNA or related nucleic acid molecules in a sequence-specific manner. In this regard, the compounds of Formula I can be used to stabilize or cross-link DNA or a related nucleic acid molecule. Also, the compounds can be used to inhibit endonuclease activity or to detect the presence or absence of an oligonucleotide comprising the nucleotide sequence, which is recognized by the compounds of Formula I. In this respect, the compounds of Formula I can be used in methods of detecting oligonucleotides, which are representative of a disease or condition (e.g., a predisposition to a disease, or a viral, parasitic or bacterial infection; etc.), for the purpose of diagnosing the disease or condition.

More importantly, the compounds of Formula I can be used to inhibit growth of a cell, to treat cancer or an infection due to a virus, parasite, or bacteria. In this regard, the invention provides a method of inhibiting growth of a cell. The method comprises administering to the cell in an amount effective to inhibit growth of a cell a compound of Formula I as described herein. A method of treating cancer in a mammal is further provided. The method comprises administering to the mammal in an amount effective to treat cancer a compound of Formula I as described herein. The invention also provides a method of treating a viral, parasitic, or bacterial infection of a cell. The method comprises administering to the cell in an amount effective to treat a viral, parasitic, or bacterial infection a compound of Formula I as described herein.

As used herein, the term "inhibit," and words stemming therefrom, do not necessarily imply 100% or complete inhibition. Rather, there are varying degrees of inhibition of which one of ordinary skill in the art recognizes as having a potential benefit or therapeutic effect. In this regard, a compound of Formula I can inhibit growth of a cell to any extent. Preferably, the compound of Formula I achieves at least 10% inhibition of cell growth as compared to the cell growth that takes place in the absence of any compound of Formula I. It is more preferred that the compound of Formula I achieves at least a 50% inhibition of cell growth as compared to growth that takes place in the absence of any compound of Formula I. Most preferred is that the compound of Formula I achieves at least a 90% inhibition of cell growth as compared to the cell growth that occurs in the absence of any compounds of Formula I. By "growth," as used herein, is meant the proliferation of cells. Cell growth is hallmarked by DNA synthesis, for example.

As used herein, the term "treat," and words stemming therefrom, do not necessarily imply 100% or complete treatment. Rather, there are varying degrees of treatment of which one of ordinary skill in the art recognizes as having a potential benefit or therapeutic effect. In this regard, a compound of Formula I can treat cancer or a viral, parasitic, or bacterial infection to any extent. Preferably, the compound of Formula I reduces the amount of virus, parasite, or bacteria in the cell by at least 10%. More preferably, the compound of Formula I reduces the amount of virus, parasite, or bacteria in the cell by at least 50%, and, more preferably, the amount is reduced upon the administration of the compound by at least 90%. The compound of Formula I can treat the cancer, for example, by reducing the tumor growth rate or size or by reducing the rate of metastasis of the cancer cells from the tumor. In this regard, the compound preferably reduces the tumor growth rate or size by at least 10%. More preferably, the compound reduces the tumor growth rate or size by at least 50%. Most preferably, the compound of Formula I reduces the tumor growth rate or size by at least 90%.

The infection to be treated by the compound of Formula I can be an infection of any virus, parasite, bacteria, or any other pathogen. The virus can be, for instance, a herpes virus, an adenovirus, a lentivirus, a Epstein-Barr virus, a human immunodeficiency virus, a West Nile virus, a Severe Acute Respiratory Syndrome virus, a smallpox virus, a polio virus, a hepatitis virus, a varicella virus, or a cytomegaolvirus. The parasite can be, for example, a leshmania, a trypanosome, a hookwork, or an amoeba (e.g., acanthamoeba). The bacteria can be, for instance, a staphylococcus, a salmonella, a mycobacteria, a streptococcus, anthrax, a clostridium, a botulinum, or an *Escherichia coli*.

With respect to the invention, the compounds of Formula I can be a part of a composition, such as a pharmaceutical composition. In this regard, the invention provides a pharmaceutical composition comprising a compound of Formula I as described herein and a pharmaceutically acceptable carrier. The pharmaceutical composition can comprise more than one active ingredient, such as more than compound of Formula I, or can comprise a compound of Formula I in combination with another pharmaceutically active agent or drug, i.e., one that is not a compound of Formula I.

The composition can comprise a carrier, which can be any suitable carrier. Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. It will be appreciated by one of skill in the art that, in addition to the following described pharmaceutical composition, the inhibitors of the present inventive methods can be formulated as inclusion complexes, such as cyclodextrin inclusion complexes, or liposomes.

The pharmaceutically acceptable carriers described herein; for example, vehicles, adjuvants, excipients, and diluents, are well-known to those skilled in the art and are readily available to the public. It is preferred that the pharmaceutically acceptable carrier be one which is chemically inert to the active compound(s) and one which has no detrimental side effects or toxicity under the conditions of use.

The choice of carrier will be determined in part by the particular compound of Formula I, as well as by the particular method used to administer the compound. Accordingly, there are a variety of suitable formulations of the pharmaceutical composition. The following formulations for oral, aerosol, parenteral, subcutaneous, intravenous, intramuscular, interperitoneal, rectal, and vaginal administration are exemplary and are in no way limiting. One skilled in the art will appreciate that these routes of administering a compound of the invention or a pharmaceutical composition comprising a compound of Formula I are known, and, although more than one route can be used to administer a particular compound, a particular route can provide a more immediate and more effective response than another route.

Injectable formulations are among those formulations that are preferred in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Topical formulations are well-known to those of skill in the art. Such formulations are particularly suitable in the context of the invention for application to the skin.

Formulations suitable for oral administration can consist of (a) liquid solutions, such as an effective amount of the inhibitor dissolved in diluents, such as water, saline, or dextrose solutions; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds of Formula I, alone, in combination with another compound of Formula I, or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The claimed compounds can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, dimethylacetamide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

The parenteral formulations will typically contain from about 0.1% to about 5% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the present inventive compounds, or compositions comprising a compound of Formula I, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

One of ordinary skill in the art will readily appreciate that the compounds of Formula I can be modified in any number of ways, such that the therapeutic efficacy of the inhibitor is increased through the modification. For instance, the compound could be conjugated either directly or indirectly through a linker to a targeting moiety. The practice of conjugating compounds to targeting moieties is known in the art. See, for instance, Wadwa et al., *J. Drug Targeting* 3: 111 (1995), and U.S. Pat. No. 5,087,616. The term "targeting moiety" as used herein, refers to any molecule or agent that specifically recognizes and binds to a cell-surface receptor, such that the targeting moiety directs the delivery of the compound to a population of cells on which surface the receptor is expressed. Targeting moieties include, but are not limited to, antibodies, or fragments thereof, peptides, hormones, growth factors, cytokines, and any other naturally- or non-naturally-existing ligands, which bind to cell surface receptors. The term "linker" as used herein, refers to any agent or molecule that bridges the compound to the targeting moiety. One of ordinary skill in the art recognizes that sites on the compound, which are not necessary for the function of the compound, are ideal sites for attaching a linker and/or a targeting moiety, provided that the linker and/or targeting moiety, once attached to the compound, do(es) not interfere with the function of the compound, i.e., the ability to inhibit growth of a cell, treat cancer in a mammal, or treat a viral, parasitic or bacterial infection of a cell.

Alternatively, the compounds of Formula I can be modified into a depot form, such that the manner in which the compound is released into the body to which it is administered is controlled with respect to time and location within the body (see, for example, U.S. Pat. No. 4,450,150). Depot forms of compounds can be, for example, an implantable composition comprising the compound and a porous material, such as a polymer, wherein the compound is encapsulated by or diffused throughout the porous material. The depot is then implanted into the desired location within the body and the compound is released from the implant at a predetermined rate by diffusing through the porous material.

The compound of Formula I can be administered to the cell in vitro. As used herein, the term "in vitro" means that the cell to which the compound is being administered is not in a living organism. The compound of Formula I alternatively can be administered to the cell in vivo. As used herein, the term "in vivo" means that the cell is a part of a living organism or is the living organism. The compound of Formula I can be administered to a host, e.g., a mammal, ex vivo, wherein the compound is administered to cells in vitro and the cells are subsequently administered to the host.

For purposes of all of the present inventive methods, the amount or dose of the compound administered should be sufficient to effect a therapeutic response in the animal over a reasonable time frame. Particularly, the dose of the compound of Formula I should be sufficient to inhibit growth of a cell or to treat cancer or an infection of a cell within about 1-2 hours, if not 3-4 hours, from the time of administration. The dose will be determined by the efficacy of the particular compound and the condition of the animal (e.g., human), as well as the body weight of the animal (e.g., human) to be treated. Many assays for determining an administered dose are known in the art, some of which are described herein as Example 3.

The size of the dose also will be determined by the existence, nature and extent of any adverse side effects that might accompany the administration of a particular compound. Ultimately, the attending physician will decide the dosage of the compound of Formula I with which to treat each individual patient, taking into consideration a variety of factors, such as age, body weight, general health, diet, sex, inhibitor to be administered, route of administration, and the severity of the condition being treated.

With respect to the present inventive methods, the cell can be a cell from any tissue of any living system. The cell can be a cell of a cultured cell line or a cell obtained from a host, e.g., a mammal. Preferably, the cell is located within the host.

For purposes herein, the host can be any host, including all prokaryotic species and eukaryotic species. In the case that the host is prokaryotic, the cell is the prokaryotic cell and not in the prokaryote. Prokaryotic cells include any cell that lacks a membrane-bound nucleus, such as bacterial cells. Eukaryotic cells include cells of yeast, fungi, plants, algae, birds, reptiles, and mammals. Preferably, the host is a mammal. For purposes of the invention, mammals include, but are not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs), or of the order Perssodactyla, including Equines (horses). It is most preferred that the mammals are of the order Primates, Ceboids, or Simoids (monkeys) or of the order Anthropoids (humans and apes). An especially preferred mammal is the human.

In a preferred embodiment of the present inventive method of inhibiting growth of a cell, a host of which the cell is comprised is afflicted with a disease or a condition, either of which is caused by hyperproliferation, and the method effectively treats the disease or condition. The disease or condition can be, for example, a benign tumor, e.g., a cyst, fibroid, a polyp, and the like. The disease can be one that is resistant to treatment with conventional therapy, such as therapy with cisplatin (e.g., certain cancers). The disease, which afflicts the host, can be a cancer, such as leukemia, lymphoma, glioma, breast cancer, bone cancer, pancreatic cancer, small cell lung cancer, lung cancer, brain cancer, skin cancer, melanoma, naso-pharyngeal cancer, stomach cancer, colon cancer, prostate cancer, etc. Preferably, the cancer is ovarian cancer, colon cancer, melanoma, glioma, or breast cancer.

In a preferred embodiment of the present inventive method of treating a viral, parasitic, or bacterial infection of a cell, the cell is in a host and the host is afflicted with a disease or condition caused by the viral, parasitic, or bacterial infection. The disease or condition can be, for instance, acquired immunodeficiency syndrome, severe acute respiratory syndrom, botulism, African sleeping sickness, a food borne illness, chicken pox, small pox, or a sexually transmitted disease (e.g., HIV, gonorrhea, *Chlamydia*, herpes simplex; etc.).

The following examples further illustrate the invention but, of course, should not be construed as in any way limiting its scope.

EXAMPLE 1

This example illustrates a method of preparing of 5H-Pyrrolo[2,1-c][1,4]benzodiazepin-5-one, 8,8'-[1,3-propanediyl-bis(oxy)]bis[11-hydroxy-1,2,3,10,11,11a-tetrahydro-7-methoxy-2-methylidene-], (11aS,11'aS), in accordance with the present invention. The method is illustrated by the 16 step sequence of FIGS. 1A-1G. Each step of the procedure is described in the following paragraphs.

1',3'-Bis[2-methoxy-4-(methoxycarbonyl)phenoxy]propane (1). Diethyl azodicarboxylate (53 g, 0.30 mol) was added, dropwise over 20 min, to a cold (0-5° C.), stirred solution of methyl 4-hydroxy-3-methoxybenzoate (50 g, 0.27 mol), triphenylphosphine (108 g, 0.411 mol), and THF (1 L). This solution was stirred (0-5° C.) for an additional 1 h, then a solution of 1,3-propanediol (11 g, 0.14 mol) in THF (15 mL) was added dropwise during 30 min. After stirring at room temperature for 48 h, the precipitated solid was collected, then dried to give 43 g (78%) of intermediate (1). Additional reactions were carried out to give a total of 191 g of product suitable for further transformation.

1',3'-Bis[2-methoxy-4-(methoxycarbonyl)-5-nitrophenoxy]-propane (2). Copper(II) nitrate trihydrate (32.1 g, 0.133 mol) was added portionwise to a stirred, cold (0-5° C.) suspension of intermediate (1) (43 g, 0.11 mol) in acetic anhydride (1 L). The reaction mixture was stirred for 1 h at 0-5° C., and 16 h at room temperature, and then poured into ice water (6.5 L). This mixture was stirred for several hours to decompose the acetic anhydride. The solid that precipitated was collected, washed with $H_2O$ (400 mL), and then dried at 50-60° C. to give 51.3 g (98%) of intermediate (2). A total of 269 g of product suitable for further transformation was prepared.

1',3'-Bis[4-carboxy-2-methoxy-5-nitrophenoxy]propane (3). A suspension of intermediate (2) (51.3 g, 0.103 mol) in THF (1 L) and dilute aqueous NaOH (41.6 g, NaOH in 1 L $H_2O$) was stirred at 50° C. for 24 h. The reaction mixture was concentrated in vacuo to remove THF, then acidified to a pH of 1 with concentrated hydrochloric acid (110 mL). The precipitated solid was collected, washed with $H_2O$ (400 mL), and then dried in vacuo at 50° C. to give 48.5 g (100%) of intermediate (3). Additional reactions were carried out to give a total of 226 g of product suitable for further transformation.

(2S,4R)-N-(Benzyloxycarbonyl)-2-carboxy-4-hydroxypyrrolidine (4). A solution of benzyl chloroformate (50 mL, 0.35 mol) in $Et_2O$ (160 mL) was added dropwise, during 10 min, to a rapidly stirred mixture of trans-4-hydroxy-L-proline (39.8 g, 0.308 mol), $NaHCO_3$ (63.7 g, 0.758 mol) and $H_2O$ (660 mL). The reaction mixture was stirred at room temperature for 20 h. The layers were separated, and the aqueous layer was washed with $Et_2O$ (4×200 mL), cooled, and then acidified to pH 1-2 with concentrated hydrochloric acid The resulting emulsion was extracted with EtOAc (5×200 mL). Combined EtOAc extracts were washed in succession with $H_2O$ (3×500 mL) and brine (3×500 mL), dried over $MgSO_4$, and then concentrated in vacuo to give intermediate (4) as a colorless foam (62.7 g, 78%). Additional reactions were carried out to give a total of 284 g of product suitable for further transformation.

(2S,4R)-N-Benzyloxycarbonyl)-2-methoxycarbonyl-4-hydroxypyrrolidine (5). A stirred solution of carboxylic acid intermediate (4) (62.7 g, 0.236 mol), anhydrous MeOH (350 mL) and concentrated sulfuric acid (2 mL) was heated at reflux for 3 h. At this time, TLC analysis (silica gel plate developed in $CH_2Cl_2$/MeOH, 10:1) indicated complete reaction The reaction mixture was cooled to room temperature, treated with $Et_3N$ (52 mL), and then concentrated in vacuo to a residue, which was dissolved in EtOAc (1 L). The EtOAc extract was washed with brine (3 L and 1 L), dried over $MgSO_4$, and then concentrated in vacuo to give intermediate (5) as a colorless oil (58.8 g, 89%). Additional reactions were carried out to give a total of 268 g of product suitable for further transformation.

(2S,4R)-N-(Benzyloxycarbonyl)-2-hydroxymethyl-4-hydroxypyrrolidine (6) To a stirred, cold (0° C.) solution of intermediate (5) (58.4 g, 0.208 mol) in THF (400 mL) was added $LiBH_4$ (3.5 g, 0.16 mol) portion-wise. The reaction mixture was stirred for 30 min at (0-5° C.) then for 4 h at room temperature. At this time, TLC (silica gel plates developed in EtOAc) showed just a trace of starting material. The thick reaction mixture was diluted in succession with $H_2O$ (250 mL) and 2 M HCl (277 mL), and then concentrated in vacuo to remove THF. The resulting aqueous concentrate was extracted with EtOAc (4×175 mL). Combined EtOAc extracts were washed with brine (2×200 mL), dried over $MgSO_4$, and then concentrated in vacuo to give intermediate (5) as an oil (51.9 g, 99%). Additional reactions were carried out to give a total of 227 g of product suitable for further transformation In later preparations the more convenient commercial solution of $LiBH_4$ in THF was used.

(2S,4R)-N-(Benzyloxycarbonyl)-2-t-butyldimethyl-silyloxymethyl-4-hydroxypyrrolidine (7). A solution of intermediate diol (6) (175 g, 0.696 mol), $Et_3N$ (98 mL, 0.72 mol), 1,8-diazabicyclo[5.4.0]undec-7-ene (20.6 mL, 0.138 mol), t-butyldimethylsilyl chloride (81.0 g, 0.537 mol) and $CH_2Cl_2$ (1.46 L) for 23 h at room temperature. Two additional portions of t-butyldimethylsilyl chloride (8.1 g, 0.054 mol each) were added at 2.5 h intervals, then stirring was continued for an additional 20 h. The reaction mixture was washed in succession with saturated aqueous $NH_4Cl$ (2×350 mL) and brine (350 mL), dried over $MgSO_4$, and then concentrated in vacuo to give 262 g of a mixture of intermediate (7), and starting diol (6). Separation was achieved by silica gel column chromatography (2×2.5 kg eluted with EtOAc/hexanes (2:3) to give 107 g (45%) of product (7), along with 60 g (34% recovery) of diol. A total of 286 g of product was prepared suitable for further transformation.

(2S,4R)-2-t-Butyldimethylsilyloxymethyl-4-hydroxypyrrolidine (8). A suspension of intermediate (7) (28.4 g, 77.7 mmol) 10% Pd/C (2.8 g) and EtOH (150 mL) was hydrogenated at 50 psi for 16 h. The catalyst was filtered off, washed with EtOH (25 mL), and then discarded. The combined filtrate and washing were spin-evaporated to give 17.5 g (97%) of intermediate (8) as an oil. Additional reactions were carried out to give a total of 102 g of product suitable for further transformation.

1,1'-[[Propane-1,3-yl)dioxy]bis[(2-nitro-5-methoxy-1,4-phenylene)carbonyl]]bis[(2S,4R)-2-t-butyldimethylsilyloxy-methyl-4-hydroxypyrrolidine] (9). Oxalyl chloride (8.1 mL, 93 mmol) was added, during 10 min, to a cold (0-5° C.), stirred solution of acid (3) (15.0 g, 32.0 mmol), DMF (5 drops) and $CH_2Cl_2$ (200 mL). This solution was stirred at room temperature for 3 h, and then concentrated in vacuo to a residue. This crude acid chloride was co-distilled with THF (100 mL), and then dissolved in THF (200 mL). The resulting acid chloride solution of (3) was added dropwise to a stirred, cold (0-5° C.) solution of intermediate (8) (47.5 g, 75.6 mmol), $Et_3N$ (13.7 g, 135 mmol) in THF (200 mL). The reaction mixture was stirred for 16 h at room temperature. Solids ($Et_3N.HCl$) were filtered off, washed with THF (50 mL), and then discarded. Combined THF solution was concentrated in vacuo to a yellow solid. This material was purified by silica gel chromato-graphy [(800 g column, $CH_2Cl_2$/MeOH (20:1) elution] to give 17.8 g, 67% of intermediate (9), as a foam. Additional reactions were carried out to give a total of 97.2 g of product suitable for further transformation.

1,1'-[[(Propane-1,3-diyl)dioxy]bis[(2-amino-5-methoxy-1,4-phenylene)carbonyl]]bis[(2S,4R)-2-t-butyldimethylsilyloxy-methyl-4-hydroxypyrrolidine] (10). A suspension of dinitro intermediate (9) (18.0 g, 20.0 mmol) in EtOH (200 mL) was hydrogenated at 50 psi during a 48 h period (1.8 g of 10% Pd/C initially, then 500 mg after 24 h). The catalyst was filtered off, washed with EtOH (30 mL), and then discarded. The combined EtOH solution was concentrated in vacuo to give 13.6 g (81%) of diamine (10) as a tan foam. Additional reactions were carried out to give a total of 86.5 g of product suitable for further transformation.

1,1'-[[Propane-1,3-diyl)dioxy]bis[(2-amino-N-allyloxycarbonyl-5-methoxy-1,4-phenylene)carbonyl]]bis[(2S,4R)-2-t-butyldimethylsilyloxymethyl-4-hydroxypyrrolidine] (11). To a cold (0-5° C.), stirred solution of intermediate (10) (15.6 g, 17.6 mmol), pyridine (6.5 g, 82 mmol) and $CH_2Cl_2$ (400 mL) was added a solution of allyl chloroformate (4.75 g, 39.4 mmol) in $CH_2Cl_2$ (100 mL) during 30 min. The reaction mixture was stirred at room temperature for 16 h, washed in succession with saturated aqueous $CuSO_4$ (2×300 mL) and $H_2O$ (2×300 mL), dried over $Na_2SO_4$, and then concentrated in vacuo to give 17.2 g (97%) of intermediate (11). Additional reactions were carried out to give a total of 93.7 g of product suitable for further transformation.

1,1'-[[(Propane-1,3-diyl)dioxy]bis[(2-amino-N-allyloxycarbonyl-5-methoxy-1,4-phenylene)carbonyl]]bis[(2S)-2-t-butyldimethylsilyloxymethyl-4-oxopyrrolidine] (12). A solution of anhydrous DMSO (7.5 g, 105 mmol) in $CH_2Cl_2$ (150 mL) was added dropwise to a cold (−65 to 65° C.), stirred solution of oxalyl chloride (5.2 g, 59 mmol) in $CH_2Cl_2$ (40 mL). Stirring was continued for 30 min (−55° C.), then a solution of alcohol (11) (17.2 g, 17.2 mmol) in $CH_2Cl_2$ (225 mL) was added during 30 min (−55° C.). After stirring for an additional 30 min at −55° C., $Et_3N$ (33 mL, 236 mmol) in $CH_2Cl_2$ (110 mL) was added over 15 min. The reaction mixture was stored for ~1.6 h at ~5° C., washed in succession with aqueous 1M HCl (2×375 mL) and brine (1×300 mL), dried over $Na_2SO_4$ and then concentrated in vacuo to a residue. This residue was purified by silica gel chromato-graphy (1 kg column, eluted with EtOAc/hexanes, 1:1) to give 12.2 g (71%) of intermediate (12) as a foam. Additional reactions were carried out to give a total of 59.0 g of product suitable for further transformation.

1,1'-[[(Propane-1,3-diyl)dioxy]bis[(2-amino-N-allyloxycarbonyl-5-methoxy-1,4-phenylene)carbonyl]]bis[(2S)-2-t-butyldimethylsilyloxymethyl-4-methylidene-2,3-dihydropyrrole] (13). A solution of potassium t-butoxide (1.0 M in THF, 64 mL, 64 mmol) was added, dropwise, to a cold (0-5° C.), stirred suspension of methyl triphenylphosphonium bromide (22.7 g, 63.5 mmol) in THF (160 mL) under Ar. The suspension was stirred for an additional 2 h at 0-5° C., then a solution of intermediate (12) (12.2 g, 12.2 mmol) in THF (160 mL) was added dropwise. The reaction mixture was stirred at room temperature for 16 h, and then concentrated in vacuo to a residue. This residue was partitioned between EtOAc (400 mL) and $H_2O$ (400 mL). The EtOAc layer was dried over $Na_2SO_4$, and then concentrated in vacuo to a residue, which was extracted with 70 mL of EtOAc/hexanes (1:1). This extract was applied to a silica gel column (400 g) and eluted with EtOAc/hexanes (1:1) to give 8.3 g (68%) of intermediate (13) as a foam. Additional reactions were carried out to give a total of 50.6 g of product suitable for further transformation.

1,1'-[[(Propane-1,3-diyl)dioxy]bis[(2-amino-N-allyloxycarbonyl-5-methoxy-1,4-phenylene)carbonyl]]bis[(2S)-2-hydroxymethyl-4-methylidene-2,3-dihydropyrrole] (14). A 1.0 M solution of tetrabutylammonium fluoride in THF (20 mL, 20 mmol) was added dropwise (15 min) to a cold (0-5° C.), stirred solution of the silyl ether (13) (15.2 g; 15.2 mmol) in THF (140 mL). After the addition was completed, the reaction mixture was stirred at room temperature for 16 h, then concentrated in vacuo to a brown residue. This residue was dissolved in EtOAc (350 mL). The EtOAc solution was washed in succession with 20% aqueous $NH_4Cl$ (2×200 mL) and brine (2×200 mL), dried over $Na_2SO_4$, and then concentrated in vacuo to a syrup (13.2 g). This crude product was purified by silica gel chromatography [500 g column, MeOH/$CH_2Cl_2$ (5:95 to 7.5:92.5) elution] to give 4.8 g (75%) of intermediate (14). Additional reactions were carried out to give a total of 29.5 g of product suitable for further transformation.

8,8'-[[(Propane-1,3-diyl)dioxy]bis(11S,11aS)-10-(allyloxycarbony)-11-hydroxy-7-methoxy-2-methylidene-1,2,3,10,11,11a-hexahydro-5H-pyrrolo[2,1-c][1,4]-benzodiazepin-5-one (15). Tetrapropylammonium perruthenate(VII) (0.22 g, 0.63 nmol) was added to a mixture of alcohol (14) (4.8 g, 6.3 mmol), N-methylmorpholine N-oxide (4.4 g, 37 mmol), powdered 4A molecular sieves (12.4 g) and $CH_2Cl_2$ (280 mL). The reaction mixture was stirred for 1 day at room temperature under argon. Thin layer chromatography (silica gel plates developed with MeOH/acetone/$CH_2Cl_2$, 1:1:18) indicated disappearance of starting material and formation of a new, major spot Insolubles were collected, washed with $CH_2Cl_2$ (200 mL), and then discarded The combined $CH_2Cl_2$ solutions were concentrated in vacuo to a black foam. This foam was purified by silica gel chromatography (260 g column eluted with MeOH/$CH_2Cl_2$, 98:2 to 96:4) to give 1.6 g (33%) of purified intermediate 15. Additional reactions were carried out to give a total of 7.2 g of product suitable for the final step.

5H-Pyrrolo[2,1-c][1,4]benzodiazepin-5-one, 8,8'-[1,3-propanediylbis(oxy)]bis[11-hydroxy-1,2,3,10,11,11a-hexahydro-7-methoxy-2-methylidene-(11aS,11'aS), (hydrate adduct of NSC-694501) (16). Tetrakis(triphenylphosphine)palladium (3.82 g, 3.3 mmol) was added to a cold (5° C.) solution of the N-allyl compound (15) (30.0 g, 39 mmol), triphenylphosphine (1.77 g, 6.7 mmol), pyrrolidine (7.2 g, 101 mmol), acetonitrile (570 mL) and $CH_2Cl_2$ (1350 mL) under argon. The reaction mixture was stirred at room temperature for 16 h. TLC analysis (silica gel $CH_2Cl_2$/MeOH 9:1) indicated the reaction was complete. The reaction mixture was concentrated in vacuo to a foam (32.0 g). This material was purified by silica gel chromatography (3 kg column, eluted with $CH_2Cl_2$/MeOH, 98:2 (8 L), and then with 97:3 (28 L)). Fractions containing product were combined and concentrated to give 19.8 g of a foam. This material was further purified by $C_{18}$ reversed-phase silica gel pad (a 200 g column eluted with $CH_3CN—H_2O$ (1:1) and collected in 50 mL fractions). Crystallization occurred in fractions 3-7 after overnight storage at room temperature. The crystalline solid from these fractions was collected and then dried in vacuo at room temperature to give 9.3 g (43%) of purified compound (16). Attempted high temperature (≧60° C.) drying of a previous sample resulted in partial decomposition. The melting point of compound (16) was determined to be 126-131° C. (dec) (uncorrected). The characterization analysis is set forth in Table 1.

TABLE 1

| | C | H | N |
|---|---|---|---|
| Calc'd for $C_{31}H_{36}N_4O_8$•1.5 $H_2O$•0.25$CH_3CN$ | 60.06 | 6.36 | 9.44 |
| Found | 59.99 | 6.23 | 9.32 |
| Spectral Data | | | |

| | | | |
|---|---|---|---|
| FT-IR (1% KBr) | Wavenumber (cm$^{-1}$) | Relative Intensity | Assignment |
| | 3600-3100 | Medium, broad | O—H, N—H stretch |
| | 1624, 1599, 1506 | Strong | C=O, C=N stretch |
| | 1464, 1431 | Strong | C=C stretch (aromatic ring) |
| | 1262 | Medium | C—O stretch |
| $^1$H Nuclear Magnetic Resonance ($CD_3CN/D_2O$) | δ 7.3-6.25 (m, H9 and H6, R/S isomers), 5.1 and 4.65 (dx2, H11, R/S isomers), 5.1 and 5.0 (sx2, =$CH_2$, R/S isomers), 4.2-4.0 (m, H3 and —$OCH_2CH_2CH_2O$—), 3.7 (sx2, 7-$OCH_3$), 3.8 and 3.5 (m, H11a, R/S isomers), 2.5-3.0 (mx2, H1, R/S isomers), 2.30-2.15 (m, —$OCH_2CH_2CH_2O$—) | | |
| $^1$H-NMR ($CD_3CN$)* | δ 7.65 (d, H11), 7.35 and 6.8 (sx2, H6 and H9), 5.1 (sx2, =$CH_2$), 4.1-4.3 (m, H3 and —$OCH_2CH_2CH_2O$—), 3.8 (s, 7-$OCH_3$), 3.7 (m, H11a), 3.0 (m, H1), 2.2 (m, —$OCH_2CH_2CH_2O$—) | | |

TABLE 1-continued

| | C | H | N |
|---|---|---|---|
| MS (ESI, Electrospray Ionization): HPLC | 597.3 (M + H$_2$O + Na$^+$), 579.3 (M + Na$^+$), 557.2 (M + H$^+$), where M is defined as the dehydrated imino form of NSC 694501 (Compound 16). 99.6% purity is observed Mobile Phase: A - Acetonitrile (23%) in 20 mM KH$_2$PO$_4$, pH 4.6; B - Acetonitrile Flow Rate: 1 mL/min Column: Discovery RP amide Detector: 320 nm | | |

*Note: Anhydrous acetonitrile-d3 dehydrates Compound 16 to the imino form.

EXAMPLE 2

Figure 2:
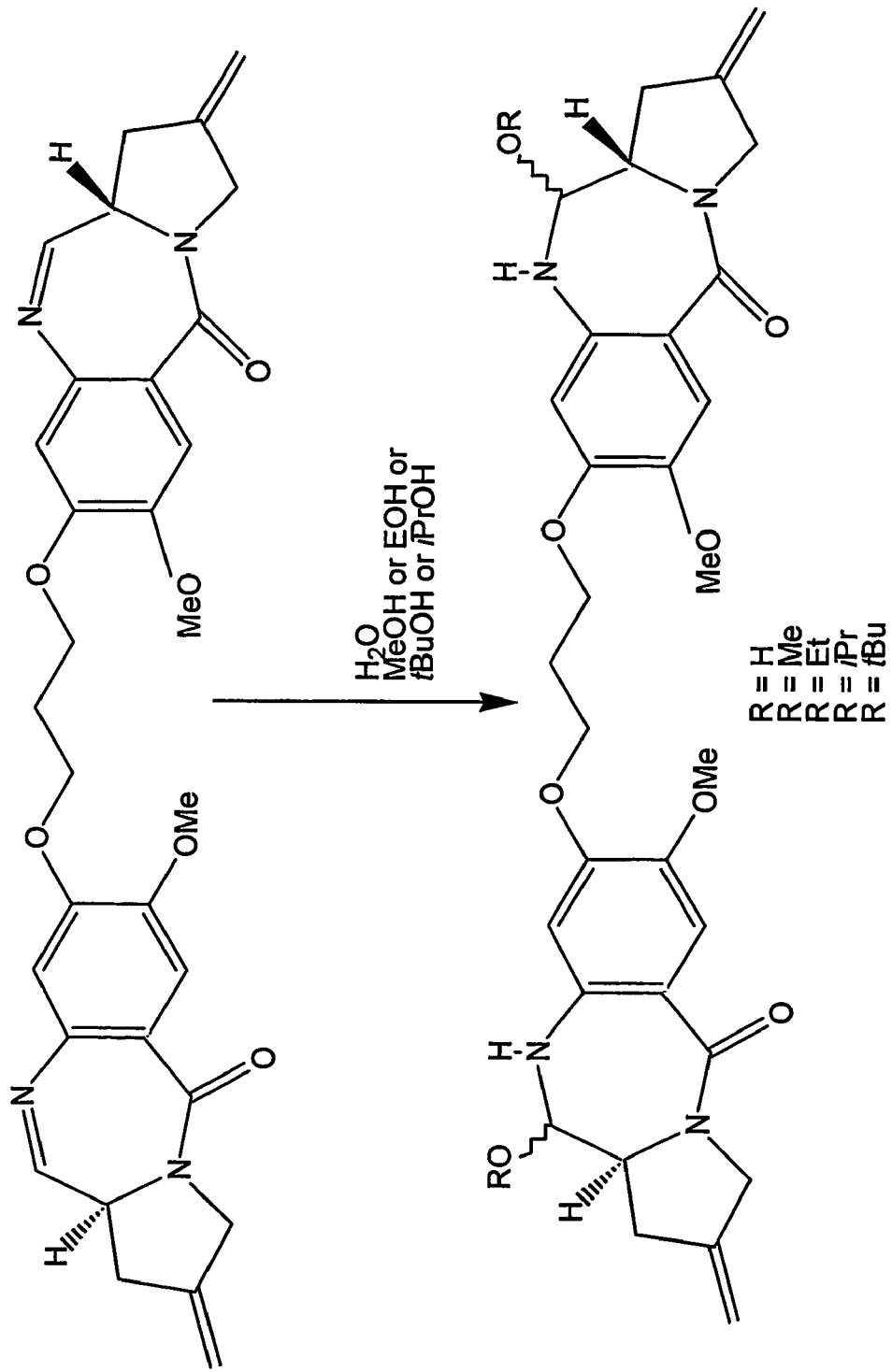
FIG. 2 is a reaction scheme illustrating the production of compounds in accordance with an embodiment of the invention.

This example illustrates a method of preparing 5H-Pyrrolo[2,1-c][1,4]benzodiazepin-5-one, 8,8'-[1,3-propanediylbis(oxy)]bis[11-methoxy-1,2,3,10,11,11a-hexahydro-7-methoxy-2-methylidene-(11aS,11'aS) (methanol adduct of NSC-694501) (FIG. 2) in accordance with an embodiment of the invention.

Figure 3:
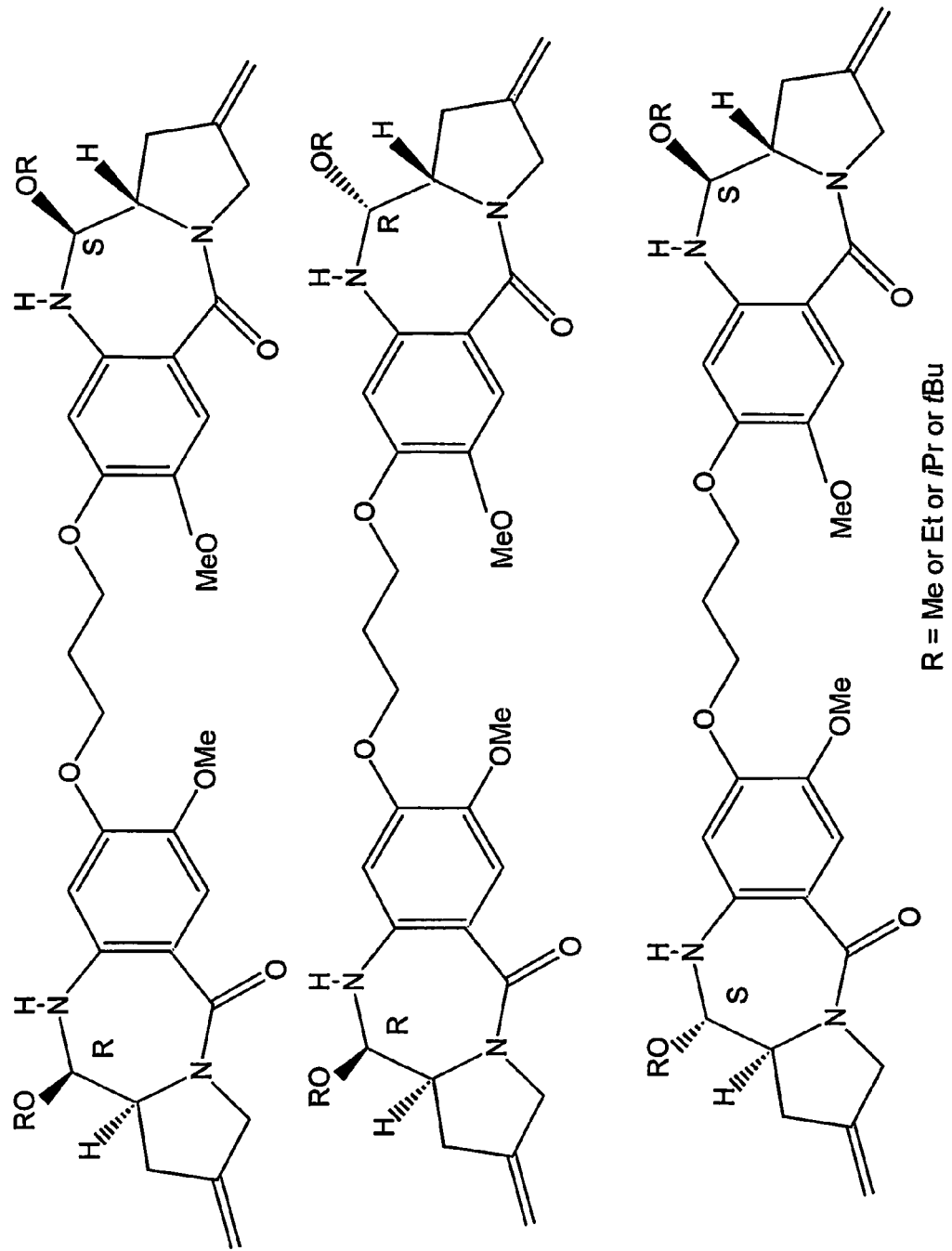
FIG. 3 illustrates certain diastereoisomers of compounds in accordance with an embodiment of the invention.

5H-Pyrrolo[2,1-c][1,4]benzodiazepin-5-one, 8,8'-[1,3-propanediylbis(oxy)]bis[1,2,3,11a-tetrahydro-7-methoxy-2-methylene-(11aS,11'aS) (NSC 694501) (~5-7.5 mg, ~10-13 μmol) (Gregson et al., *J. Med. Chem.* 44: 737-748 (2001)) was treated with anhydrous methanol (3 mL) and the reaction mixture was allowed to stir under nitrogen for 24 h to form the methanol adduct. Excess solvent was removed by evaporation in vacuo and the resulting solid compound was weighed and analysed by $^1$H NMR/COSY techniques in d$_6$-DMSO: $^1$H NMR (400 MHz, d$_6$-DMSO) δ 7.24 (br s, NH), 7.07 (s, H6-R), 6.65 (s, H6S), 6.42 (s, H9-R), 6.13 (s, H9-S), 5.13 and 5.10 (s×2,=CH$^2$—S), 4.99 and 4.97 (s×2, =CH$_2$—R), 4.54 (d, J=6.2 Hz, H11-R), 4.27 (d, J=9.7 Hz, H11-S), 4.25-4.05 (m, —OCH$_2$CH$_2$CH$_2$O— and H3), 3.98 (d, J=15.9 Hz, H3), 3.92-3.79 (m, H11a-R), 3.82 (d, J=15.6 Hz, H3), 3.73 (s, 7-OCH$_3$—S), 3.68 (s, 7-OCH$_3$—R), 3.65-3.55 (m, H11a-S), 3.37 (s, 11-OCH$_3$—S), 3.23 (s, 11-OCH$_3$—R), 3.10-2.85 (m, H1), 2.82 (d, J=14.1 Hz, H1-R), 2.46 (d, partially obscured by DMSO peak, H1-S), 2.30-2.15 (m, —OCH$_2$CH$_2$CH$_2$O—). FIG. 3 shows the formula of certain diastereomers obtained herein and in Examples 3-5.

EXAMPLE 3

This example illustrates a method of preparing 5H-Pyrrolo[2,1-c][1,4]benzodiazepin-5-one, 8,8'-[1,3-propanediylbis(oxy)]bis[11-ethoxy-1,2,3,10,11,11a-hexahydro-7-methoxy-2-methylidene-(11aS,11'aS) (ethanol adduct of NSC-694501) (FIG. 2) in accordance with an embodiment of the invention.

The same procedure described in Example 2 was followed, except that anhydrous ethanol was used instead of methanol. After the ethanol adduct had formed, excess solvent was removed by evaporation in vacuo and the resulting solid compound was weighed and analysed by $^1$H NMR/COSY techniques in d$_6$-DMSO: $^1$H NMR (400 MHz, d$_6$-DMSO) δ 7.22 (s, NH—S), 7.21 (d, J=5.7 Hz, NH—R), 7.07 (s, H6-R), 6.62 (s, H6-S), 6.49(s, H9-R), 6.03 (s, H9-S), 5.13 and 5.10 (s×2, =CH$_2$—S), 4.99 and 4.96 (s×2, =CH$_2$—R), 4.65(d, J=6.1 Hz, H11-R), 4.35 (d, J=9.0 Hz, H11-S), 4.25-4.05 (m, —OCH$_2$CH$_2$CH$_2$O—and H3), 3.98 (d, J=16.0 Hz, H3), 3.92-3.79 (m, H11a-R and H3), 3.73 (s, 7-OCH$_3$—S), 3.67 (s, 7-OCH$_3$—R), 3.60-3.43 (m, H11a-S and —OCH$_2$CH$_3$), 3.10-2.85 (m, H1), 2.68 (d, J=15.2 Hz, H1-R), 2.46 (d, partially obscured by DMSO peak, H1-S), 2.30-2.15 (m, —OCH$_2$CH$_2$CH$_2$O—), 1.10-1.00 (m, —OCH$_2$CH$_3$).

EXAMPLE 4

This example illustrates a method of preparing 5H-Pyrrolo[2,1-c][1,4]benzodiazepin-5-one, 8,8'-[1,3-propanediylbis(oxy)]bis[11-i-propyloxy-1,2,3,10,11,11a-hexahydro-7-methoxy-2-methylidene-(11aS,11'aS) (isopropanol adduct of NSC-694501) (FIG. 2) in accordance with an embodiment of the invention.

The same procedure described in Example 2 was followed, except that anhydrous isopropanol was used instead of methanol. After the isopropanol adduct had formed, excess solvent was removed by evaporation in vacuo and the resulting solid compound was weighed and analysed by $^1$H NMR/COSY techniques in d$_6$-DMSO: $^1$H NMR (500 MHz, d$_6$-DMSO) δ 7.22 (s, NH—S), 7.16 (d, J=6.1 Hz, NH—R), 7.05 (s, H6-R), 6.60 (s, H6-S), 6.37 (s, H9-R), 5.90 (s, H9-S), 5.13 and 5.10 (s×2; =CH$_2$—S), 4.98 and 4.95 (s×2, =CH$_2$—R), 4.73 (d, J=6.2 Hz, H11-R), 4.43 (d, J=9.0 Hz, H11-S), 4.30-4.05 (m, —OCH$_2$CH$_2$CH$_2$O— and H3), 3.98 (d, J=15.8 Hz, H3), 3.90-3.75 (m, H11a-R, H3 and —CH(CH$_3$)$_2$), 3.73 (s, 7-OCH$_3$—S), 3.67 (s, 7-OCH$_3$—R), 3.53-3.35 (m, H11a-S), 3.00-2.95 (m, H1—R), 2.94-2.85 (m, H1-S), 2.63 (d, J=16.5 Hz, H1—R), 2.43 (d, J=15.5 Hz, H1-S), 2.30-2.15(m, —OCH$_2$CH$_2$CH$_2$O—),1.20-0.99 (m, —CH(CH$_3$)$_2$). The persistence of imine signals was observed in this spectrum.

EXAMPLE 5

This example illustrates a method of preparing 5H-Pyrrolo[2,1-c][1,4]benzodiazepin-5-one, 8,8'-[1,3-propanediylbis(oxy)]bis[11-t-butoxy-1,2,3,10,11,11a-hexahydro-7-methoxy-2-methylidene-(11aS,11'aS) (t-butanol adduct of NSC-694501) (FIG. 2) in accordance with an embodiment of the invention.

The same procedure described in Example 2 was followed, except that anhydrous t-butanol was used instead of methanol. After the t-butanol adduct had formed, excess solvent was removed by evaporation in vacuo and the resulting solid compound was weighed and analysed by $^1$H NMR/COSY techniques in d$_6$-DMSO: $^1$H NMR (400 MHz, d$_6$-DMSO) δ 7.23 (s, NH—S), 7.22-7.17 (m, NH—R), 7.07 (s, H6-R), 6.62 (s, H6-S), 6.38 (s, H9-R), 6.03 (s, H9-S), 5.13 and 5.10 (s×2, =CH$_2$—S), 4.99 and 4.96 (s×2, =CH$_2$—R), 4.65 (d, J=6.1 Hz, H11-R), 4.40-4.35 (m, H11-S), 4.30-4.05 (m, —OCH$_2$CH$_2$CH$_2$O— and H3), 3.94 (d, J=15.2 Hz, H3), 3.90-3.77 (m, H11a-R, H3 and 7-OCH$_3$—S), 3.68 (s, 7-OCH$_{3—R}$), 3.65-3.52 (m, H11a-S), 3.05-2.85 (m, H1), 2.68 (d, J=15.2 Hz, H1-R), 2.47 (d, obscured by DMSO peak, H1-S), 2.30-2.15 (m, —OCH$_2$CH$_2$CH$_2$O—), 1.20-1.00 (m, —C(CH$_3$)$_3$). The persistence of imine signals was observed in this spectrum.

EXAMPLE 6

Figure 4:
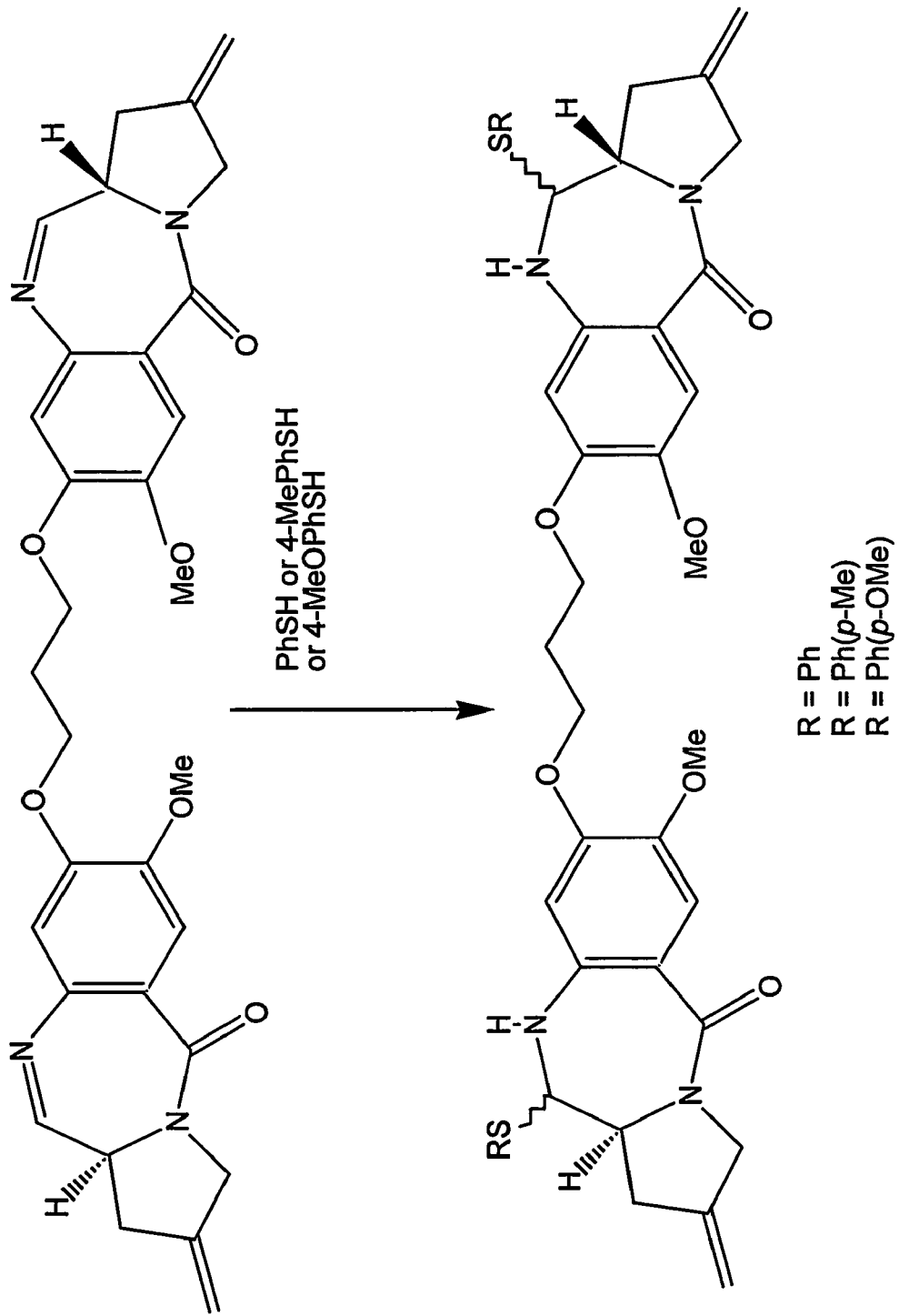
FIG. 4 is a reaction scheme illustrating a method for preparing compounds in accordance with an embodiment of the invention.

This example illustrates a method of preparing 5H-Pyrrolo[2,1-c][1,4]benzodiazepin-5-one, 8,8'-[1,3-propanediylbis(oxy)]bis[11-(4-methyl-phenylthio)-1,2,3,10,11,11a-hexadydro-7-methoxy-2methylidene-(11aS, 11'aS) (thiophenol adduct of NSC-694501) (FIG. 4) in accordance with an embodiment of the invention.

Figure 5:
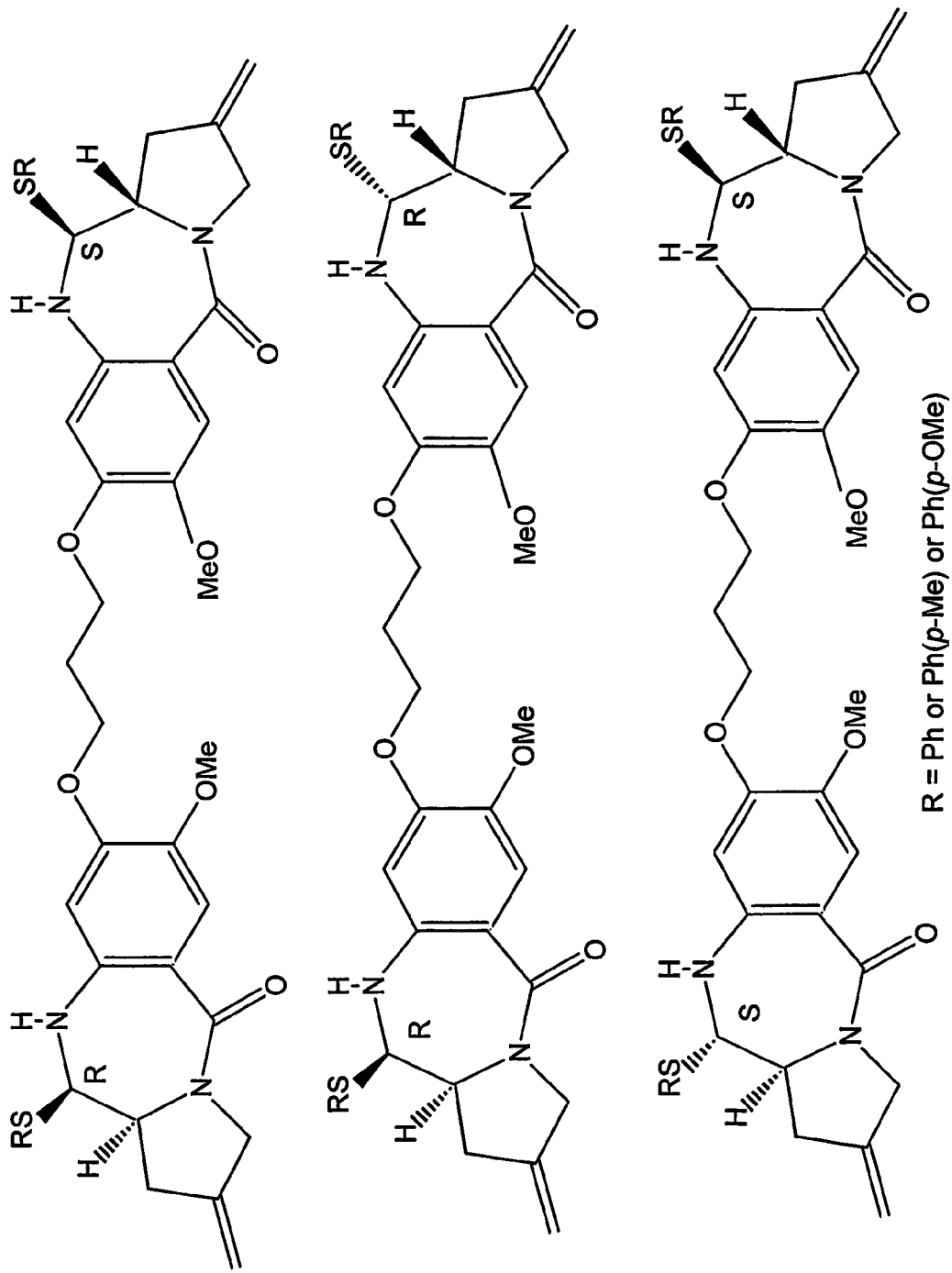
FIG. 5 illustrates certain diastereoisomers of compounds in accordance with an embodiment of the invention.

5H-Pyrrolo[2,1-c][1,4]benzodiazepin-5-one, 8,8'-[1,3-propanediylbis(oxy)]bis[1,2,3,11a-tetrahydro-7-methoxy-2-methylene-(11aS,11'aS) (NSC-694501) (~5-6.5 mg, ~10-12

µmol) in anhydrous THF (1 mL) was treated with p-methylthiophenol (2 mol equivalents) and the reaction mixture was allowed to stir under nitrogen for 24 h to form the methylthiophenol adduct. Excess solvent was removed by evaporation in vacuo and the resulting solid compound was weighed and analysed by $^1$H NMR/COSY techniques in $d_6$-DMSO: $^1$H NMR (500 MHz, $d_6$-DMSO) δ 7.48 (d, J=8.0 Hz, thioether Ar-3'H—S), 7.45-7.38 (m, NH—R and thioether Ar 3'H—R), 7.21 (d, J=8.0 Hz, thioether Ar-2'H—S), 7.16 (d, J=7.8 Hz, thioether Ar-2'H—R), 6.99 (s, H6-S), 6.89 (s, H6-R), 6.50 (s, H9-S), 6.45 (s, H9-R), 5.79 (s, NH—S), 5.16 (d, J=6.4 Hz, H11-R), 5.07 and 5.04 (s×2, =CH$_2$), 4.76 (d, J=10.9 Hz, H11-S), 4.28 (d, J=16.3 Hz, H3), 4.25-4.21 (m, H11a-R), 4.19 (d, J=16.5 Hz, H3), 4.14-4.00 (m, —OCH$_2$CH$_2$CH$_2$O—), 3.85-3.76 (m, H11a-S), 3.69 (s, 7-OCH$_3$), 3.15 (dd, J=16.3, 8.5 Hz, H1-R), 3.08-3.05 (m, H1-S), 2.93 (d, J=16.4 Hz, H1-R), 2.80-2.70 (m, H1-S), 2.35-2.15 (m, —OCH$_2$CH$_2$CH$_2$O— and -PhCh$_3$). FIG. 5 shows the formulas of certain diastereomers obtained herein and in Examples 7-8 below.

EXAMPLE 7

This example illustrates a method of preparing 5H-Pyrrolo[2,1-c][1,4]benzodiazepin-5-one, 8,8'-[1,3-propanediylbis(oxy)]bis[11-phenylthio-1,2,3,10,11,11a-hexahydro-7-methoxy-2-methylidene-(11aS,11'aS) (thiophenol adduct of NSC-694501) (FIG. 4) in accordance with an embodiment of the invention.

The same procedure described in Example 6 was followed, except that thiophenol was used instead of p-methylthiophenol. After the thiophenol adduct had formed, excess solvent was removed by evaporation in vacuo and the resulting solid compound was weighed and analysed by $^1$H NMR/COSY techniques in $d_6$-DMSO: $^1$H NMR (400 MHz, $d_6$-DMSO) δ 7.62-7.20 (m, thioether Ar, NH—R), 6.99 (s, H6-S), 6.89 (s, H6-R), 6.50 (s, H9-S), 6.45 (s, H9-R), 5.86 (s, NH—S), 5.29 (d, J=6.5 Hz, H11-R), 5.15-5.00 (m, =CH$_2$), 4.83 (d, J=11.0 Hz, H11-S), 4.28 (d, J=16.4 Hz, H3), 4.25-34.00 (m, H11a-R, H3 and —OCH$_2$CH$_2$CH$_2$O—), 3.90-3.75 (m, H11a-S), 3.70 and 3.68 (s×2,7-OCH$_3$), 3.25-3.05 (m, H1), 2.95-2.85 (m, H1-R), 2.80-2.70 (m, H1-S), 2.35-2.15 (m, —OCH$_2$CH$_2$CH$_2$O—).

EXAMPLE 8

This example illustrates a method of preparing 5H-Pyrrolo[2,1-c][1,4]benzodiazepin-5-one, 8,8'-[1,3-propanediylbis(oxy)]bis[11-(4-methoxy-phenylthio)-1,2,3,10,11,11a-hexahydro-7-methoxy-2-methylidene-(11aS, 11'aS) (methoxythiophenol) adduct of NSC-694501) (FIG. 4) in accordance with an embodiment of the invention.

The same procedure described in Example 6 was followed, except that p-methoxythiophenol was used instead of p-methylthiophenol. After the thiophenol adduct had formed, excess solvent was removed by evaporation in vacuo and the resulting solid compound was weighed and analysed by $^1$H NMR/COSY techniques in $d_6$-DMSO: $^1$H NMR (400 MHz, $d_6$-DMSO) δ 7.60-7.50 (m, thioether Ar), 7.45-7.40 (m, thioether Ar), 7.39-7.32 (m, thioether Ar and NH—R), 7.00-6.90 (m, thioether Ar, H6-S and H6-R), 6.50 (s, H9-S), 6.45 (s, H9-R), 5.79 (s, NH—S), 5.13-5.00 (m, H11-R and =CH$_2$), 4.66 (d, J=10.8 Hz, H11-S), 4.35-3.95 (m, H3, H11a-R and —OCH$_2$CH$_2$CH$_2$O—), 3.85-3.65 (m, H11a-S, 7-OCH$_3$ and -PhOCH$_3$), 3.20-3.05 (m, H1), 3.00-2.90 (m, H1-R), 2.79 (d, J=16.0 Hz, H1-S), 2.35-2.15 (m, —OCH$_2$CH$_2$CH$_2$O—).

EXAMPLE 9

Figure 6:
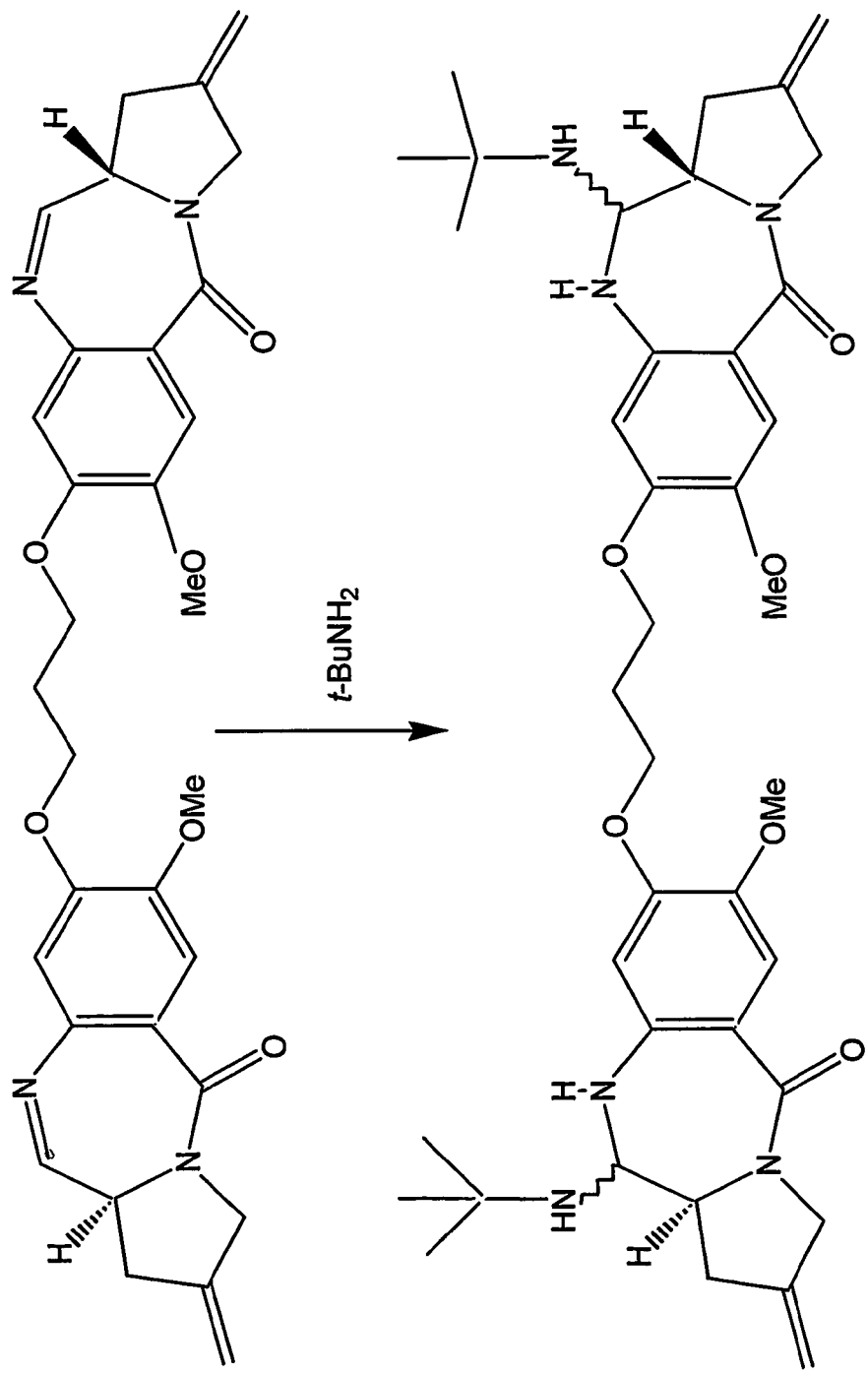
FIG. 6 is a reaction scheme illustrating a method for preparing a compound in accordance with an embodiment of the invention.
Figure 7:
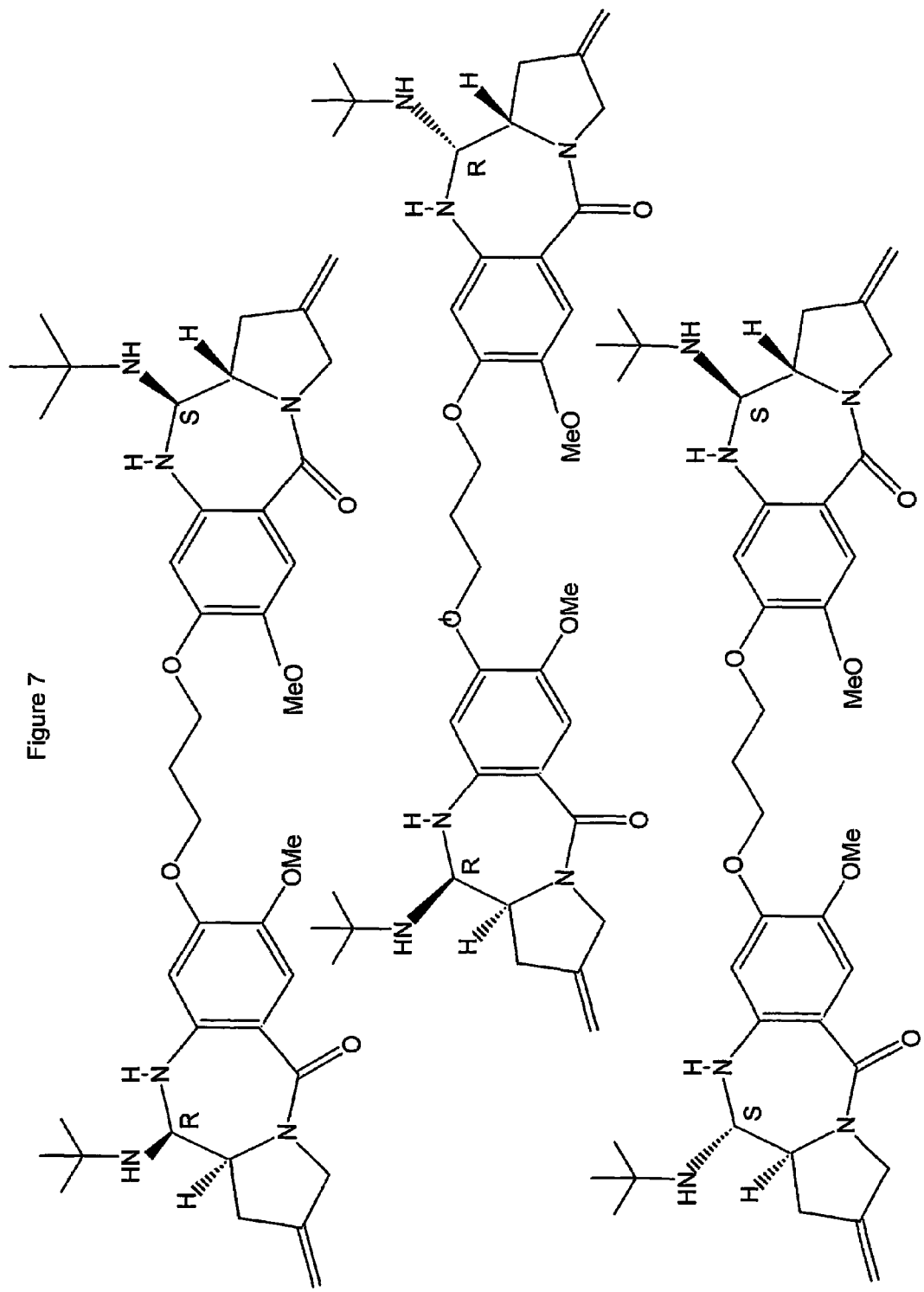
FIG. 7 illustrates certain diastereoisomers of a compound in accordance with an embodiment of the invention.

This example illustrates a method of preparing 5H-Pyrrolo[2,1-c][1,4]benzodiazepin-5-one, 8,8'-[1,3-propanediylbis(oxy)]bis[11-t-butylamino-1,2,3,10,11,11a-hexahydro-7-methoxy-2-methylidene-(11aS,11'aS) (t-butylamine adduct of NSC-694501) in accordance with an embodiment of the invention (FIG. 6).

Anhydrous t-butylamine (3 mL) was added to a sample of 5H-Pyrrolo[2,1-c][1,4]benzodiazepin-5-one, 8,8'-[1,3-propanediylbis(oxy)]bis[1,2,3,11a-tetrahydro-7-methoxy-2-methylene-(11aS,11'aS) (5.56 mg, 10 µmol) and the reaction mixture was allowed to stir in a flask fitted with a CaCl$_2$ drying tube for 24 h. Excess solvent was removed by evaporation in vacuo, and the resulting t-butylamine adduct was weighed (6.94 mg, 99%) and analysed by $^1$H NMR/COSY techniques in $d_6$-DMSO: $^1$H NMR (500 MHz, $d_6$-DMSO) δ 7.28 (s, H6-S), 7.21 (s, H6-R), 6.85 (d, J=6.27 Hz, NH—R), 6.62 (s, H9-R), 6.39 (s, H9-S), 6.05 (br s, NH-aminal), 5.53 (br s, NH—S), 5.12 and 5.08 (s×2, =CH$_2$), 5.05-4.85 (m, =CH$_2$ and H11-R), 4.54 (d, J=8.7 Hz, H11-S), 4.40-3.95 (m, —OCH$_2$CH$_2$CH$_2$O—and H3), 3.94-3.83 (m, H11a-R), 3.80 and 3.79 (s×2,7-OCH$_3$), 3.69-3.58 (m, H11a-S), 3.00-2.85 (m, H1), 2.67 (d, J=16.8 Hz, H1-R), 2.56 (d, J=16.1 Hz, H1-S), 2.35-2.15 (m, —OCH$_2$CH$_2$CH$_2$O—). The persistence of N10-C11 imine signals was observed in this spectrum.

EXAMPLE 10

This example demonstrates the biological activity of a compound of the invention in vitro.

5H-Pyrrolo[2,1-c][1,4]benzodiazepin-5-one, 8,8'-[1,3-propanediylbis(oxy)]bis[11-hydroxy-1,2,3,10,11,11a-hexahydro-7-methoxy-2-methylidene-(11aS,11'aS), (hydrate adduct of NSC-694501) (16) dissolved in DMSO and water was tested in vitro in a 60-cell-line screen. The concentration effects of the compound for various cancer cell lines are summarized in Tables 2-10, wherein GI50 is the drug concentration required to inhibit the growth of 50% of the cells, TGI is the drug concentration required for total growth inhibition, and LC50 is the drug concentration required to kill 50% of the cells. These data demonstrate that the hydrate adduct of NSC694501 is very potent and has a multi-log differential pattern of activity. A COMPARE analysis shows that, although the agent compares in general terms with DNA-binding agents, it does not fit within any of the clusters of known agents, including anthramycin or bizelesin, suggesting distinctive aspects of NSC 694501 action in comparison to other DNA-binding agents.

TABLE 2

| Leukemia | Log$_{10}$[C] (M) | | | Concentration (nM) | | |
|---|---|---|---|---|---|---|
| Cell Line ID | GI50 | TGI | LC50 | GI50 | TGI | LC50 |
| CCRF-CEM | −9.72 | −7.85 | −6 | 0.2 | 14.1 | 1000.0 |
| HL-60(TB) | −9.62 | −8.62 | −7.55 | 0.2 | 2.4 | 28.2 |
| MOLT-4 | −9.85 | −9 | −7.15 | 0.1 | 1.0 | 70.8 |
| RPMI-8226 | −9.85 | −8.05 | −7.08 | 0.1 | 8.9 | 83.2 |

TABLE 3

| Non-Small Cell Lung Cell Line ID | Log$_{10}$[C] (M) | | | Concentration (nM) | | |
|---|---|---|---|---|---|---|
| | GI50 | TGI | LC50 | GI50 | TGI | LC50 |
| A549/ATCC | −7.85 | −6 | −6 | 14.1 | 1000.0 | 1000.0 |
| EKVX | −7.17 | −6.34 | −6 | 67.6 | 457.1 | 1000.0 |
| HOP-62 | −7.96 | — | −6 | 11.0 | — | 1000.0 |
| HOP-92 | −8.17 | −6.82 | −6 | 6.8 | 151.4 | 1000.0 |
| NCI-H226 | −7.92 | −7.32 | −6 | 12.0 | 47.9 | 1000.0 |
| NCI-H23 | −8.77 | −7.8 | −7.17 | 1.7 | 15.8 | 67.6 |
| NCI-H322M | −7.52 | −7.09 | −6 | 30.2 | 81.3 | 1000.0 |
| NCI-H460 | −9.55 | −6 | −6 | 0.3 | 1000.0 | 1000.0 |
| NCI-H522 | −8.85 | −7.51 | −6 | 1.4 | 30.9 | 1000.0 |

TABLE 4

| Colon Cell Line ID | Log$_{10}$[C] (M) | | | Concentration (nM) | | |
|---|---|---|---|---|---|---|
| | GI50 | TGI | LC50 | GI50 | TGI | LC50 |
| COLO 205 | −8.26 | −7.47 | −6.6 | 5.5 | 33.9 | 251.2 |
| HCC-2998 | −7.74 | −7.38 | — | 18.2 | 41.7 | — |
| HCT-116 | −7.96 | −7.59 | — | 11.0 | 25.7 | — |
| HCT-15 | −6.92 | −6.01 | −6 | 120.2 | 977.2 | 1000.0 |
| HT29 | −7.89 | −7.52 | — | 12.9 | 30.2 | — |
| KM12 | −7.7 | −7.14 | −6 | 20.0 | 72.4 | 1000.0 |
| SW-620 | −7.85 | −6 | −6 | 14.1 | 1000.0 | 1000.0 |

TABLE 5

| Central Nervous System Cell Line ID | Log$_{10}$[C] (M) | | | Concentration (nM) | | |
|---|---|---|---|---|---|---|
| | GI50 | TGI | LC50 | GI50 | TGI | LC50 |
| SF-268 | −9.08 | −7.24 | −6 | 0.8 | 57.5 | 1000.0 |
| SF-295 | −8.15 | −6 | −6 | 7.1 | 1000.0 | 1000.0 |
| SF-539 | −8.34 | −7.92 | −6 | 4.6 | 12.0 | 1000.0 |
| SNB-19 | −8.27 | −6 | −6 | 5.4 | 1000.0 | 1000.0 |
| SNB-75 | −8.74 | −7.82 | −6.33 | 1.8 | 15.1 | 467.7 |
| U251 | −8.7 | — | −6 | 2.0 | — | 1000.0 |

TABLE 6

| Melanoma Cell Line ID | Log$_{10}$[C] (M) | | | Concentration (nM) | | |
|---|---|---|---|---|---|---|
| | GI50 | TGI | LC50 | GI50 | TGI | LC50 |
| MALME-3M | −7.92 | −7.54 | −7.15 | 12.0 | 28.8 | 70.8 |
| M14 | −8.07 | −6 | −6 | 8.5 | 1000.0 | 1000.0 |
| SK-MEL-2 | −7.77 | −7.46 | −7.14 | 17.0 | 34.7 | 72.4 |
| SK-MEL-28 | −7.82 | −7.36 | −6 | 15.1 | 43.7 | 1000.0 |
| SK-MEL-5 | −7.89 | −7.57 | — | 12.9 | 26.9 | — |
| UACC-257 | −7.82 | −7.38 | −6 | 15.1 | 41.7 | 1000.0 |
| UACC-62 | −9.59 | −9.08 | −8.15 | 0.3 | 0.8 | 7.1 |

TABLE 7

| Ovarian Cell Line ID | Log$_{10}$[C] (M) | | | Concentration (nM) | | |
|---|---|---|---|---|---|---|
| | GI50 | TGI | LC50 | GI50 | TGI | LC50 |
| IGROV1 | −7.77 | — | −6 | 17.0 | — | 1000.0 |
| OVCAR-3 | −7.72 | — | −6 | 19.1 | — | 1000.0 |
| OVCAR-4 | −7.51 | −6 | −6 | 30.9 | 1000.0 | 1000.0 |
| OVCAR-5 | −7.7 | −7.35 | −6 | 20.0 | 44.7 | 1000.0 |
| OVCAR-8 | −7.92 | −6 | −6 | 12.0 | 1000.0 | 1000.0 |
| SK-OV-3 | −7.7 | −6 | −6 | 20.0 | 1000.0 | 1000.0 |

TABLE 8

| Renal Cell Line ID | Log$_{10}$[C] (M) | | | Concentration (nM) | | |
|---|---|---|---|---|---|---|
| | GI50 | TGI | LC50 | GI50 | TGI | LC50 |
| 786-0 | −8.89 | −7.8 | −6 | 1.3 | 15.8 | 1000.0 |
| A498 | — | −7.6 | — | — | 25.1 | — |
| ACHN | −8.14 | −7.04 | −6 | 7.2 | 91.2 | 1000.0 |
| CAKI-1 | −7.96 | −6.15 | −6 | 11.0 | 707.9 | 1000.0 |
| SN12C | −8.82 | −7.74 | −6 | 1.5 | 18.2 | 1000.0 |
| TK-10 | −7.55 | — | −6 | 28.2 | — | 1000.0 |
| UO-31 | −7.32 | −6.54 | −6 | 47.9 | 288.4 | 1000.0 |

TABLE 9

| Prostate Cell Line ID | Log$_{10}$[C] (M) | | | Concentration (nM) | | |
|---|---|---|---|---|---|---|
| | GI50 | TGI | LC50 | GI50 | TGI | LC50 |
| PC-3 | −7.68 | −6 | −6 | 20.9 | 1000.0 | 1000.0 |
| DU-145 | −8.3 | −6 | −6 | 5.0 | 1000.0 | 1000.0 |

TABLE 10

| Breast Cell Line ID | Log$_{10}$[C] (M) | | | Concentration (nM) | | |
|---|---|---|---|---|---|---|
| | GI50 | TGI | LC50 | GI50 | TGI | LC50 |
| NCI/ADR-RES | −6.49 | −6 | −6 | 323.6 | 1000.0 | 1000.0 |
| MDA-MB-231/ATCC | −7.74 | −7.35 | −6 | 18.2 | 44.7 | 1000.0 |
| HS 578T | −7.37 | −6 | −6 | 42.7 | 1000.0 | 1000.0 |
| MDA-MB-435 | −7.89 | −7.47 | −7.07 | 12.9 | 33.9 | 85.1 |
| MDA-N | −7.96 | −7.59 | −7.24 | 11.0 | 25.7 | 57.5 |
| BT-549 | −7.89 | −7.31 | −6 | 12.9 | 49.0 | 1000.0 |
| T-47D | −7.62 | −6 | −6 | 24.0 | 1000.0 | 1000.0 |

EXAMPLE 11

This example demonstrates the biological activity of a compound of the invention in vivo.

A standard panel of 12 tumor cell lines was used for the routine hollow fiber screening. These included NCI-H23, NCI-H522, MDA-MB-231, MDA-MB-435, SW-620, COLO 205, LOX, UACC-62, OVCAR-3, OVCAR-5, U251 and SF-295. In addition, alternate lines were used for specialized testing of compounds on a nonroutine basis. The cell lines were cultivated in RPMI-1640 containing 10% FBS and 2 mM glutamine. On the day preceeding hollow fiber preparation, the cells were given a supplementation of fresh medium to maintain log phase growth. For fiber preparation, the cells were harvested by standard trypsinization technique and resuspended at the desired cell density ((2-10×10$^6$ cells/ml). The cell suspension was flushed into 1 mm (internal diameter) polyvinylidene fluoride hollow fibers with a molecular weight exclusion of 500,000 Da. The hollow fibers were heat-sealed at 2 cm intervals and the samples generated from these seals were placed into tissue culture medium and incubated at 37° C. in 5% CO$_2$ for 24 to 48 hours prior to implantation. A total of 3 different tumor lines were prepared for each experiment so that each mouse receives 3 intraperitoneal implants (1 of each tumor line) and 3 subcutaneous implants (1 of each tumor line). On the day of implantation, samples of each tumor cell line preparation were quantitated for viable cell mass by a stable endpoint MTT assay so that the time zero cell mass is known. Mice were treated with experimental agents starting on day 3 or 4 following fiber implantation and continuing daily for 4 days. Each agent was administered by intraperitoneal injection at 2 dose levels. The fibers were collected from the mice on the day following the fourth compound treatment and subjected to the stable endpoint MTT assay. The optical density of each sample was determined spectrophotometrically at 540 nm and the mean of each treatment group was calculated. The percent net growth for each cell line in each treatment group was calculated and compared to the percent net growth in the vehicle treated controls. A 50% or greater reduction in percent net growth in the treated samples compared to the vehicle control samples was considered a positive result. Each positive result was given a score of 2 and all of the scores were totaled for a given compound. The maximum possible score for an agent is 96 (12 cell lines×2 sites×2 dose levels×2 [score]). A compound was referred for xenograft testing if it had a combined ip+sc score of 20 or greater, a sc score of 8 or greater, or produced cell kill of any cell line at either dose level evaluated.

In vivo evaluation of NSC 694501 in the hollow fiber assay resulted in a total score of 54 (40 intraperitoneal [i.p.]+14 subcutaneous [s.c.].) with three cell lines killed: UACC-62 melanoma, OVCAR-3 ovarian cancer, and MDA-MB-435 breast cancer.

A qD×5 schedule conferred better efficacy than a q4D×3 schedule in each of the 4 models tested on two schedules. NSC 694501 was active over a wide dosage range in athymic mice using compound prepared fresh just prior to injection in 1% EtOH vehicle: On a qD×5 schedule, the maximum tolerated dose was approximately 120 μg/kg/dose and the minimum effective dose in one of the most sensitive models (SF-295) was 16 μg/kg/dose. Likewise, NSC 694501 prepared fresh just prior to injection in 1% EtOH vehicle was observed to be well tolerated and efficacious in nude rats bearing C-6 (rat glioma) and LS-174 (human colon cancer) at doses of 27 and 40 μg/kg/dose, i.v., qD×5 (Table 12).

TABLE 12

| Model | Stage/ Implant Site | Treatment Schedule | Dose (mg/kg) | BW Loss % | Activity Optimal % T/C | Growth Delay % [(T − C)/C]C |
|---|---|---|---|---|---|---|
| C-6 | Early-SC | QD ×5 | 0.040 | 0.8 | 24 | 49 |
|  |  |  | 0.027 | 6.3 | 47 | 20 |
|  |  |  | 0.018 | 0.0 | 56 | 13 |
| LS-174 | Early-SC | QD ×5 | 0.040 | 1.4 | 17 | 83 |
|  |  |  | 0.027 | 2.2 | 21 | 93 |
|  |  |  | 0.018 | 0.0 | 41 | 43 |

TABLE 11

| Model | Stage/ Implant Site | Treatment Schedule* | MTD (mg/kg/dose) | BW Loss % | Activity Optimal % T/C | Growth Delay % [(T − C)/C]C |
|---|---|---|---|---|---|---|
| LOX | IP | QD ×5 | 0.40 | 20.7 |  | [−10% ILS] |
|  | Early-SC | QD ×5 | 0.054 | 17.6 | 7 | 498 (4.3 L) |
| UACC-62 | Early-SC | Q4D ×3 | .45 | 20.9 | 28 | 43 |
|  |  | QD ×5 | 0.054 | 20.2 | 26 | 150 (0.9 L) |
| OVCAR-3 | Early-SC | Q4D ×3 | 0.45 | 6.6 | 20 | 73 |
|  |  | Q4D ×3 | 0.45 | 13.9 | 10 | 55 |
|  |  | QD ×5 | .27 | 7.9 | 9 | 114 (1.9 L) |
| OVCAR-5 | Early-SC | Q4D ×3 | 0.45 | 21.2 | 38 | 32 |
|  |  | QD ×5 | 0.081 | 2.6 | 13 | 102 |
| MDA-MB-435 | Early-SC | Q4D ×3 | 0.45 | 19.8 | 3(1 tf) | 41 |
| SF-295 | Early-SC | Q4D ×3 | <0.30 | 24.0 | ue(2 tf) |  |
|  |  | QD ×5 | 0.12 | 7.5 | 4(4 tf) | 241 (3.1 L) |
| SF-295 | Early-SC | Q4D ×3 | 0.24 | 10.2 | 1(1 tf) | 227 (3.2 L) |
|  |  |  | 0.16 | 4.3 | 3 | 103 (0.9 L) |
|  |  |  | 0.11 | 0.1 | 10 | 60 (0.0 L) |
|  |  | QD ×5 | 0.12 | 5.3 | 2(2 tf) | 196 (3.2 L) |
|  |  |  | 0.08 | 0.0 | 3 | 131 (2.0 L) |
|  |  |  | 0.054 | 4.7 | 2(1 tf) | 165 (2.6 L) |
|  |  | QD ×5 | 0.054 | 2.8 | 0 | 206 (3.0 L) |
|  |  |  | 0.036 | 3.5 | 14 | 69 |
|  |  |  | 0.024 | 3.6 | 12 | 61 |
|  |  |  | 0.016 | 0.0 | 33 | 31 |

*Treatments given by intravenous administration
tf = tumore free;
ue = unevaluable NSC 694501 was evaluated for in vivo efficacy in athymic mice bearing 8 subcutaneous tumor models: LOX and UACC-62 (melanoma), OVCAR-3 and OVCAR-5 (ovarian ca), MDA-MB-435 (breastca), SF-295 and C-6 (glioma), and LS-174T (colonca). The models were selected on the basis of hollow fiber assays and in vitro time course assays.

NSC 694501 was active in each of the 8 tumor models following i.v bolus drug delivery with optimal T/C values ranging from 0% to 38%, with significant growth delays in 7 models as well as multi-log cell kill in 4 models and 2-4/6 tumor-free responses in 1 model. The results are summarized in Table 11.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound of Formula I:

(Formula I)

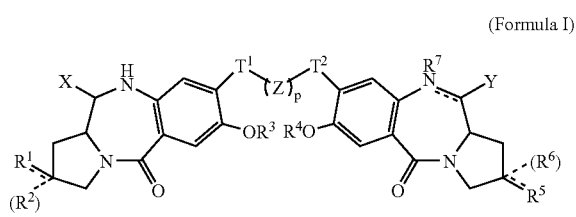

wherein X is a substituent selected from the group consisting of an OH, —OR, —OSiH$_3$, —OSiRR'R", —OCOR, —OCOOR, —OCONHR, —OCSNHR, —SH, —SR, —SOR, —SOOR, —OSO$_2$R, —OSO$_2$H, —NHSOOR, —NH$_2$, —NHCOR, —NR'COR, —NHR, —NRR', —N$_3$, —CN, halogen, —P$^+$Ph$_3$X$^-$, —SiH$^3$, —SiRR'R", —OCSOR, —OCO(CHR)$_u$COOR, —OCO(CHR)$_u$SR', —OCO(CHR)$_u$NR'R", —OCO(CHR)$_u$P(=O)R'R", —OCO(CHR)$_u$P(=O)(OH)(R'), cysteine, glutathione,

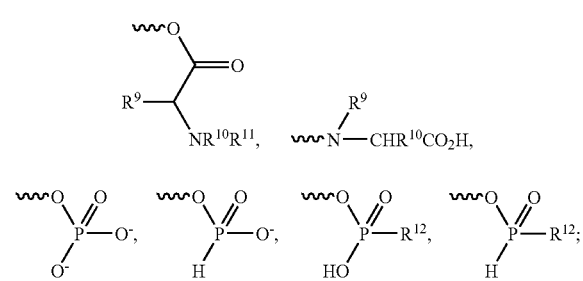

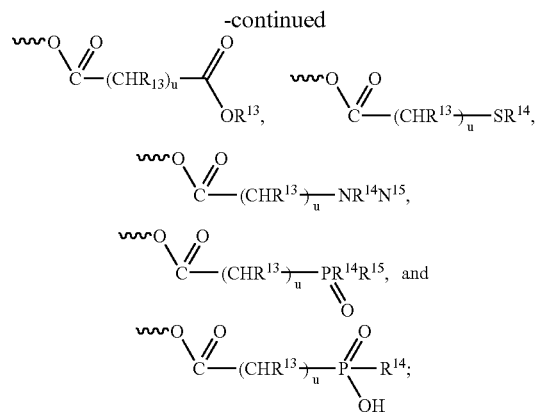

wherein each of R$^9$, R$^{10}$, and R$^{11}$ is independently selected from the group consisting of H, C$_1$-C$_8$ alkyl optionally substituted with an amine or a carboxylate; an aryl; an aryl alkyl; and a heterocycle;

wherein R$^{12}$ is C$_1$-C$_8$ alkyl optionally substituted with an aryl, a heterocycle, an alkoxy, a halo, an amine, or carboxylate; an aryl; or a heterocycle, wherein each of R$^{13}$, R$^{14}$, and R$^{15}$ is independently selected from the group consisting of H; C$_1$-C$_8$ alkyl optionally substituted with an aryl, a heterocycle, an alkoxy, a halo, an amine, or carboxylate; an aryl; and a heterocycle, and wherein u is an integer from 1 to about 16, wherein the bond between the carbon to which Y is attached and the N of NR$^7$ to which the carbon is attached is a single bond or a double bond, wherein, when the bond is a double bond, R$^7$ is absent and Y is H, and, when the bond is a single bond, R$^7$ is H and Y is a substituent selected from the group defined for X, wherein Y is optionally the same as X;

wherein each of T$^1$ and T$^2$ is independently O, S, or NR$^8$;

wherein R, R', and R" are independently selected from the group consisting of C$_1$-C$_{24}$ alkyl optionally substituted with an amino, hydroxyl, or thiol group, C$_3$-C$_{24}$ cycloalkyl, C$_2$-C$_{24}$ alkenyl, C$_3$-C$_{26}$ alkoxyacetyl, and a group of the structure:

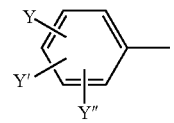

wherein Y and Y' are independently hydrogen, C$_1$-C$_{24}$ alkyl, arylalkyl, C$_2$-C$_{24}$ alkenyl, C$_2$-C$_{24}$ alkynyl, C$_1$-C$_{24}$ alkoxy, halogen, or Y and Y' taken together form 3,4-methylenedioxy, and Y" is hydrogen, C$_1$-C$_{24}$ alkyl, C$_1$-C$_{24}$ alkoxy, or halogen; naphthalenalkyl optionally substituted by methyl or halogen; phenyl(C$_2$-C$_{24}$ alkenyl); wherein the phenyl is optionally substituted with methyl or halogen; cinnamyl; pyridinealkyl optionally substituted with methyl or halogen; dihydropyridinealkyl optionally substituted with C$_1$-C$_{24}$ alkyl; thiophenealkyl optionally substituted with methyl or halogen; C$_6$-C$_{14}$ aryl; allyl; and furanalkyl optionally substituted with methyl or halogen;

wherein Z is a divalent radical of an alkane, an alkene, or an alkyne;

wherein p is an integer that is greater than or equal to 2;

wherein each of $R^3$, $R^4$, and $R^8$ is independently a hydrogen; a $C_1$-$C_{24}$ alkyl, $C_2$-$C_{24}$ alkenyl, or $C_2$-$C_{24}$ alkynyl, optionally substituted with a group selected from the group consisting of an aryl, a heterocycle, and an amine; or an aryl optionally substituted with an alkyl, an aryl, an alkoxy, a halo, an amine, a hydroxy, or a trifluoromethyl;

wherein the bond between $R^1$ and the carbon to which $R^1$ is attached is a single bond or a double bond, wherein, when the bond is a double bond, $R^2$ is absent and $R^1$ is a divalent radical derived from an alkane, an aromatic hydrocarbon, or a heterocycle, and when the bond is a single bond, $R^1$ and $R^2$ are independently selected from the group consisting of H, $C_1$-$C_8$ alkyl, aryl, and a heterocycle; and wherein the bond between $R^5$ and the carbon to which $R^5$ is attached is a single bond or a double bond, wherein, when the bond is a double bond, $R^6$ is absent and $R^5$ is a divalent radical derived from an alkane, an aromatic hydrocarbon, or a heterocycle, and when the bond is a single bond, $R^5$ and $R^6$ are independently selected from the group consisting of H, $C_1$-$C_8$ alkyl, aryl, and a heterocycle;

or a salt thereof, wherein the compound is a solid.

2. A compound of Formula I:

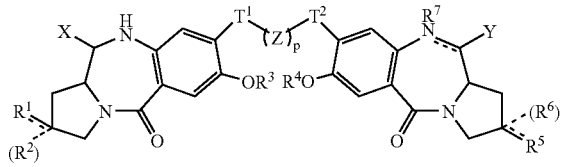

(Formula I)

wherein X is a substituent selected from the group consisting of an OH, —OR, —OSiH$_3$, —OSiRR'R", —OCOR, —OCOOR, —OCONHR, —OCSNHR, —SH, —SR, —SOR, —SOOR, —OSO$_2$R, —OSO$_2$H, —NHSOOR, —NH$_2$, —NHCOR, —NHCOR', —NHR, —NRR', —N$_3$, —CN, halogen, —P$^+$Ph$_3$X$^-$, —SiH$_3$, —SiRR'R", —OCSOR, —OCO(CHR)$_u$COOR, —OCO(CHR)$_u$SR', OCO(CHR)$_u$NR'R", —OCO(CHR)$_u$P(=O)R'R", —OCO(CHR)$_u$P(=O)(OH)(R'), cysteine, glutathione,

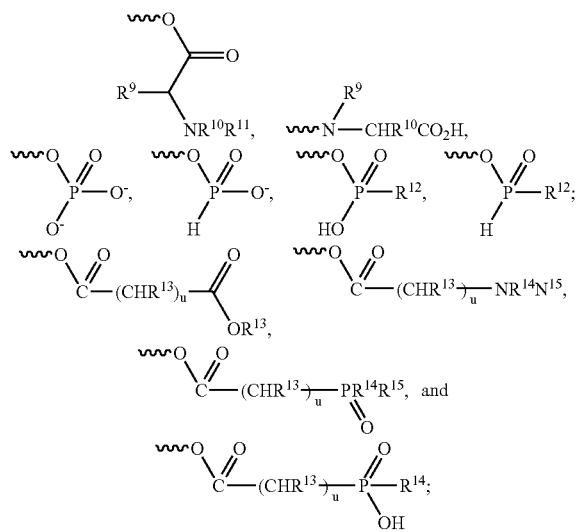

wherein each of $R^9$, $R^{10}$, and $R^{11}$ is independently selected from the group consisting of H, a $C_1$-$C_8$ alkyl optionally substituted with an amine or a carboxylate; an aryl; an aryl alkyl; and a heterocycle;

wherein $R^{12}$ is $C_1$-$C_8$ alkyl optionally substituted with an aryl, a heterocycle, an alkoxy, a halo, an amine, or carboxylate; an aryl; or a heterocycle, wherein each of $R^{13}$, $R^{14}$, and $R^{15}$ is independently selected from the group consisting of H; $C_1$-$C_8$ alkyl optionally substituted with an aryl, a heterocycle, an alkoxy, a halo, an amine, or carboxylate; an aryl; and a heterocycle, and wherein u is an integer from 1 to about 16, wherein the bond between the carbon to which Y is attached and the N of NR$^7$ to which the carbon is attached is a single bond or a double bond, wherein, when the bond is a double bond, $R^7$ is absent and Y is H, and, when the bond is a single bond, $R^7$ is H and Y is a substituent selected from the group defined for X, wherein Y is optionally the same as X;

wherein each of $T^1$ and $T^2$ is independently O, S, or NR$^8$;

wherein R, R', and R" are independently selected from the group consisting of $C_1$-$C_{24}$ alkyl optionally substituted with an amino, hydroxyl, or thiol group, $C_3$-$C_{24}$ cycloalkyl, $C_2$-$C_{24}$ alkenyl, $C_3$-$C_{26}$ alkoxyacetyl, and a group of the structure:

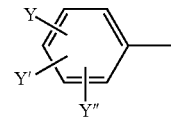

wherein Y and Y' are independently hydrogen, $C_1$-$C_{24}$ alkyl, arylalkyl, $C_2$-$C_{24}$ alkenyl, $C_2$-$C_{24}$ alkynyl, $C_1$-$C_{24}$ alkoxy, halogen, or Y and Y' taken together form 3,4-methylenedioxy, and Y" is hydrogen, $C_1$-$C_{24}$ alkyl, $C_1$-$C_{24}$ alkoxy, or halogen; naphthalenalkyl optionally substituted by methyl or halogen; phenyl($C_2$-$C_{24}$ alkenyl); wherein the phenyl is optionally substituted with methyl or halogen; cinnamyl; pyridinealkyl optionally substituted with methyl or halogen; dihydropyridinealkyl optionally substituted with $C_1$-$C_{24}$ alkyl; thiophenealkyl optionally substituted with methyl or halogen; $C_6$-$C_{14}$ aryl; allyl; and furanalkyl optionally substituted with methyl or halogen;

wherein Z is a divalent radical of an alkane, an alkene, or an alkyne;

wherein p is an integer that is greater than or equal to 2;

wherein each of $R^3$, $R^4$, and $R^8$ is independently a hydrogen; a $C_1$-$C_{24}$ alkyl, $C_2$-$C_{24}$ alkenyl, or $C_2$-$C_{24}$ alkynyl, optionally substituted with a group selected from the group consisting of an aryl, a heterocycle, and an amine; or an aryl optionally substituted with an alkyl, an aryl, an alkoxy, a halo, an amine, a hydroxy, or a trifluoromethyl;

wherein the bond between $R^1$ and the carbon to which $R^1$ is attached is a single bond or a double bond, wherein, when the bond is a double bond, $R^2$ is absent and $R^1$ is a divalent radical derived from an alkane, an aromatic hydrocarbon, or a heterocycle, and when the bond is a single bond, $R^1$ and $R^2$ are independently selected from the group consisting of H, $C_1$-$C_8$ alkyl, aryl, and a heterocycle; and wherein the bond between $R^5$ and the carbon to which $R^5$ is attached is a single bond or a double bond, wherein, when the bond is a double bond, $R^6$ is absent and $R^5$ is a divalent radical derived from an alkane, an aromatic hydrocarbon, or a heterocycle, and when the bond is a single bond, $R^5$ and $R^6$ are independently selected from the group consisting of H, $C_1$-$C_8$ alkyl, aryl, and a heterocycle;

or a salt thereof;

provided that, when each of $R^1$ and $R^5$ is $CH_2$ attached by a double-bond, $R^2$ and $R^6$ are absent, $R^3$ and $R^4$ are $CH_3$, $R^7$ is H, $T^1$ and $T^2$ are both O, Z is $CH_2$, and p is 3, then X and Y are not both methoxy, both ethoxy, or both hydroxyl; and when each of $R^1$, $R^2$, $R^5$, and $R^6$ are H, then X and Y are not both sulfide or both ether.

3. A compound of Formula I:

(Formula I)

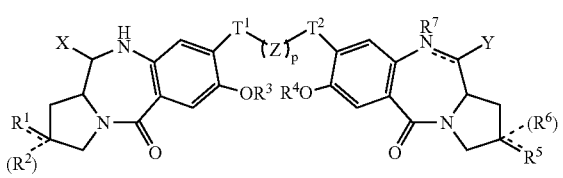

wherein X is a substituent selected from the group consisting of —$OSiH_3$, —OSiRR'R", —OCOR, —OCOOR, —OCONHR, —OCSNHR, —SH, —SR, —SOR, —SOOR, —$OSO_2R$, —$OSO_2H$, —NHSOOR, —$NH_2$, —NHCOR, —NHCOR', —NHR, —NRR', —$N_3$, —CN, halogen, —$P^+Ph_3X^-$, —$SiH_3$, —SiRR'R", cysteine, glutathione,

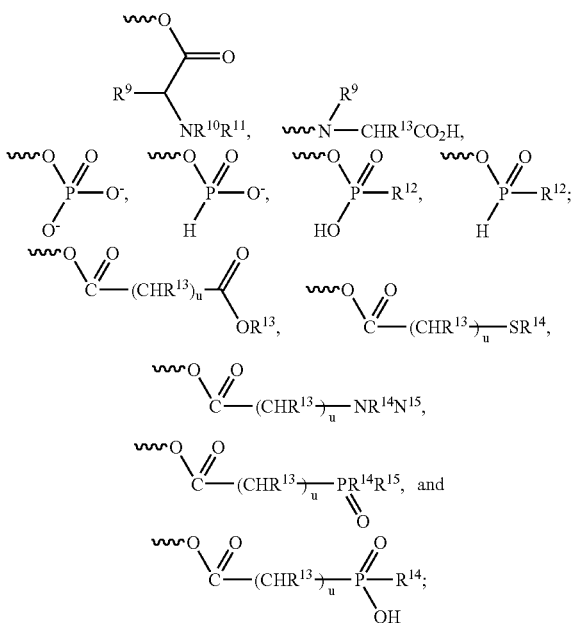

wherein each of $R^9$, $R^{10}$, and $R^{11}$ is independently selected from the group consisting of H, a $C_1$-$C_8$ alkyl optionally substituted with an amine or a carboxylate; an aryl; an aryl alkyl; and a heterocycle;

wherein $R^{12}$ is $C_1$-$C_8$ alkyl optionally substituted with an aryl, a heterocycle, an alkoxy, a halo, an amine, or carboxylate; an aryl; or a heterocycle, wherein each of $R^{13}$, $R^{14}$, and $R^{15}$ is independently selected from the group consisting of H; $C_1$-$C_8$ alkyl optionally substituted with an aryl, a heterocycle, an alkoxy, a halo, an amine, or carboxylate; an aryl; and a heterocycle, and wherein u is an integer from 1 to about 16, wherein the bond between the carbon to which Y is attached and the N of $NR^7$ to which the carbon is attached is a single bond or a double bond, wherein, when the bond is a double bond, $R^7$ is absent and Y is H, and, when the bond is a single bond, $R^7$ is H and Y is a substituent selected from the group defined for X, wherein Y is optionally the same as X;

wherein each of $T^1$ and $T^2$ is independently O, S, or $NR^8$;

wherein R, R', and R" are independently selected from the group consisting of $C_1$-$C_{24}$ alkyl optionally substituted with an amino, hydroxyl, or thiol group, $C_3$-$C_{24}$ cycloalkyl, $C_2$-$C_{24}$ alkenyl, $C_3$-$C_{26}$ alkoxyacetyl, and a group of the structure:

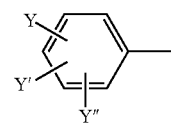

wherein Y and Y' are independently hydrogen, $C_1$-$C_{24}$ alkyl, arylalkyl, $C_2$-$C_{24}$ alkenyl, $C_2$-$C_{24}$ alkynyl, $C_1$-$C_{24}$ alkoxy, halogen, or Y and Y' taken together form 3,4-methylenedioxy, and Y" is hydrogen, $C_1$-$C_{24}$ alkyl, $C_1$-$C_{24}$ alkoxy, or halogen; naphthalenalkyl optionally substituted by methyl or halogen; phenyl($C_2$-$C_{24}$ alkenyl) wherein the phenyl is optionally substituted with methyl or halogen; cinnamyl; pyridinealkyl optionally substituted with methyl or halogen; dihydropyridinealkyl optionally substituted with $C_1$-$C_{24}$ alkyl; thiophenealkyl optionally substituted with methyl or halogen; $C_6$-$C_{14}$ aryl; allyl; and furanalkyl optionally substituted with methyl or halogen;

wherein Z is a divalent radical of an alkane, an alkene, or an alkyne;

wherein p is an integer that is greater than or equal to 2;

wherein each of $R^3$, $R^4$, and $R^8$ is independently a hydrogen; a $C_1$-$C_{24}$ alkyl, $C_2$-$C_{24}$ alkenyl, or $C_2$-$C_{24}$ alkynyl, optionally substituted with a group selected from the group consisting of an aryl, a heterocycle, and an amine; or an aryl optionally substituted with an alkyl, an aryl, an alkoxy, a halo, an amine, a hydroxy, or a trifluoromethyl;

wherein the bond between $R^1$ and the carbon to which $R^1$ is attached is a single bond or a double bond, wherein, when the bond is a double bond, $R^2$ is absent and $R^1$ is a divalent radical derived from an alkane, an aromatic hydrocarbon, or a heterocycle, and when the bond is a single bond, $R^1$ and $R^2$ are independently selected from the group consisting of H, $C_1$-$C_8$ alkyl, aryl, and a heterocycle; and wherein the bond between $R^5$ and the carbon to which $R^5$ is attached is a single bond or a double bond, wherein, when the bond is a double bond, $R^6$ is absent and $R^5$ is a divalent radical derived from an alkane, or an aromatic hydrocarbon, and when the bond is a single bond, $R^5$ and $R^6$ are independently selected from the group consisting of H, $C_1$-$C_8$ alkyl, aryl, and a heterocycle;

or a salt thereof.

4. The compound or a salt thereof of claim 1, wherein X is selected from the group consisting of:

(a)

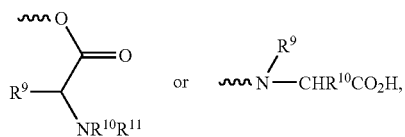

wherein each of $R^9$, $R^{10}$, and $R^{11}$ is independently selected from the group consisting of H, a $C_1$-$C_8$ alkyl optionally substituted with an amine or a carboxylate; an aryl; an aryl alkyl; and a heterocycle, (b) a group of the formula:

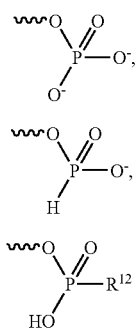

(i)
(ii)
(iii)

wherein $R^{12}$ is $C_1$-$C_8$ alkyl optionally substituted with an aryl, a heterocycle, an alkoxy, a halo, an amine, or carboxylate; an aryl; or a heterocycle, or

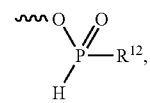

wherein $R^{12}$ is $C_1$-$C_8$ alkyl optionally substituted with an aryl, a heterocycle, an alkoxy, a halo, an amine, or carboxylate; an aryl; or a heterocycle,

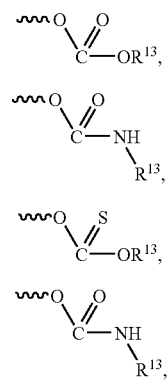

(c)
(d)
(e)
(f)

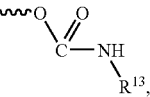

-continued

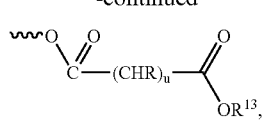

(g)

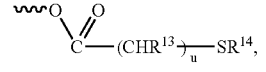

(h)

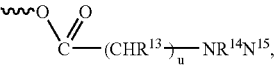

(i)

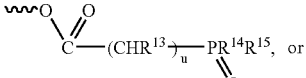

(j)

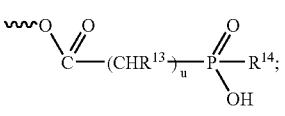

(k)

wherein, each of $R^{13}$, $R^{14}$, and $R^{15}$ is independently selected from the group consisting of H; $C_1$-$C_8$ alkyl optionally substituted with an aryl, a heterocycle, an alkoxy, a halo, an amine, or carboxylate; an aryl; and a heterocycle, and wherein u is 1 to about 16;

(l)
and (l) a monohydroxylic or a polyhydroxylic group.

5. The compound or a salt thereof of claim 1, wherein each of $T^1$ and $T^2$ is O, p is 3 and Z is —$CH_2$—.

6. The compound or a salt thereof of claim 1, wherein $R^1$ and $R^2$ are not both H.

7. The compound or a salt thereof of claim 1, wherein each of $R^3$ and $R^4$ is a $C_1$-$C_8$ alkyl optionally substituted with an aryl or amine; or an aryl optionally substituted with an alkyl, an aryl, an alkoxy, a halo, an amine, a hydroxy, or a trifluoromethyl.

8. The compound or a salt thereof of claim 1, wherein $R^8$ is H.

9. The compound or a salt thereof of claim 1, wherein (a) each of X and Y is OH, (b) X is OH and Y is H, or (c) X is OR and R is an alkyl.

10. The compound or a salt thereof of claim 9, wherein X is OR and R is a $C_1$-$C_8$ alkyl.

11. The compound or a salt thereof of claim 1, wherein Y is the same as X.

12. The compound or a salt thereof of claim 1, wherein the compound is selected from the group consisting of:

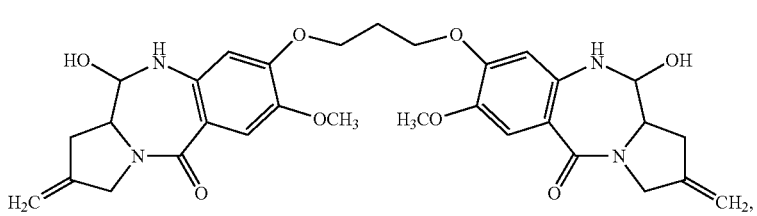

(a)

-continued (b)
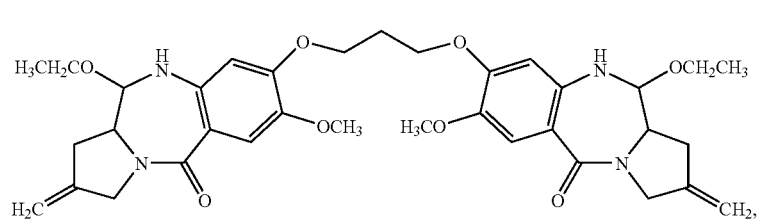

(c)
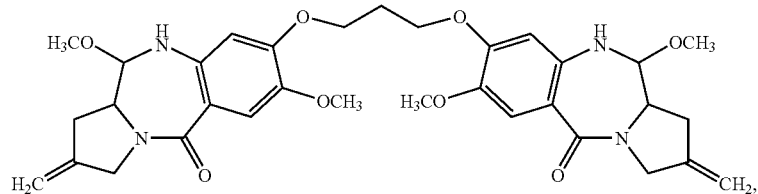

(d)
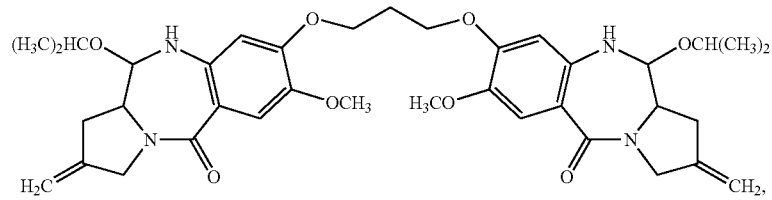

(e)
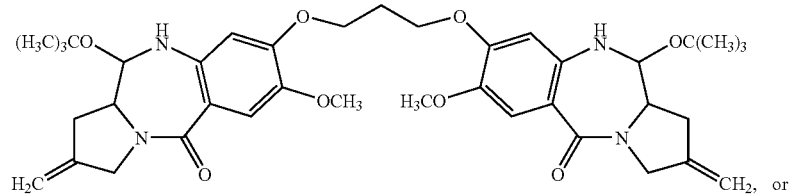

or (f)
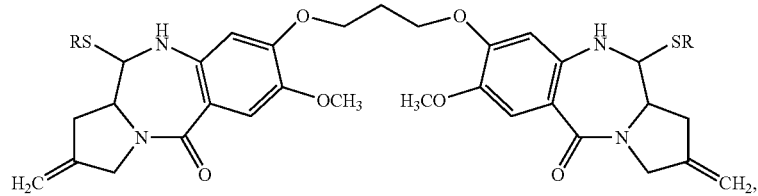

wherein, for structure (f), the following applies: R is $C_1$-$C_{24}$ alkyl optionally substituted with an amino, hydroxyl, or thiol group; $C_3$-$C_{24}$ cycloalkyl, a $C_2$-$C_{24}$ alkenyl; a cyclohexylalkyl; a $C_3$-$C_{26}$ alkoxyacetyl; a naphthalenalkyl optionally substituted with methyl or halogen; a phenyl ($C_3$-$C_{26}$ alkenyl), wherein the phenyl is optionally substituted with methyl or halogen; a cinnamyl; a pyridinealkyl optionally substituted with methyl or halogen; a dihydropyridine alkyl optionally substituted with $C_1$-$C_{24}$ alkyl; a thiophenealkyl optionally substituted with methyl or halogen; an aryl; an allyl; a furanalkyl optionally substituted with methyl or halogen; cysteine; glutathione; or a group of structure

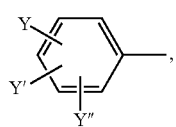

wherein each of Y and Y' is independently hydrogen, $C_1$-$C_{24}$ alkyl, arylalkyl, $C_2$-$C_{24}$ alkenyl, $C_2$-$C_{24}$ alkynyl, $C_1$-$C_{24}$ alkoxy, or halogen, or Y and Y' together form 3,4-methylenedioxy, and Y" is hydrogen, $C_1$-$C_{24}$ alkyl, $C_1$-$C_{24}$ alkoxy or halogen.

13. The compound or a salt thereof of claim 12, wherein the compound is of structure (f) and R is

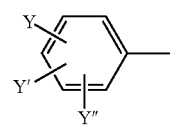

wherein each of Y and Y' is independently hydrogen, $C_1$-$C_8$ alkyl, $C_1$-$C_8$ alkoxy, or halogen, or Y and Y' together form 3,4-methylenedioxy, and Y" is hydrogen, $C_1$-$C_8$ alkyl, $C_1$-$C_8$ alkoxy or halogen.

14. The compound or a salt thereof of claim 1, wherein the compound is

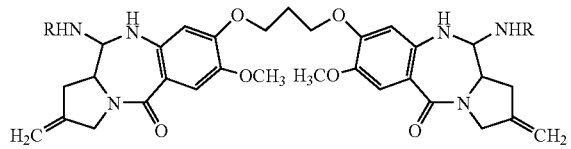

wherein R is $C_1$-$C_{24}$ alkyl optionally substituted with an amino, hydroxyl, or thiol group; a $C_3$-$C_{24}$ cycloalkyl; a $C_2$-$C_{24}$ alkenyl; a $C_3$-$C_{26}$ alkoxyacetyl; a naphthalenalkyl optionally substituted with methyl or halogen; phenyl ($C_2$-$C_{24}$ alkenyl), wherein the phenyl is optionally substituted with methyl or halogen; cinnamyl; pyridinealkyl optionally substituted with methyl or halogen; dihydropyridine alkyl optionally substituted with $C_1$-$C_{24}$ alkyl; thiophenealkyl optionally substituted with methyl or halogen; an aryl; an allyl; furanalkyl optionally substituted with methyl or halogen; or a group of structure

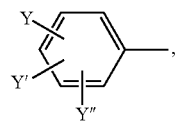

wherein each of Y and Y' is independently hydrogen, $C_1$-$C_{24}$ alkyl, $C_1$-$C_{24}$ alkoxy, or halogen, or Y and Y' together form 3,4-methylenedioxy, and Y" is hydrogen, $C_1$-$C_{24}$ alkyl, $C_1$-$C_{24}$ alkoxy or halogen.

15. A pharmaceutical composition comprising a compound or a salt thereof of claim 1 and a pharmaceutically acceptable carrier.

16. A method of preparing the compound or a salt thereof of claim 1, wherein the compound is of Formula I

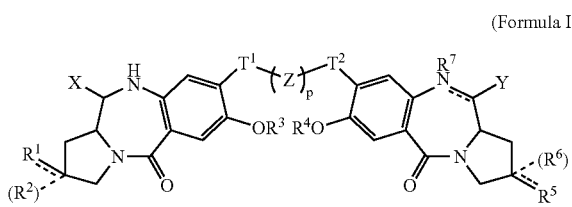

(Formula I)

wherein X is OH,
wherein the bond between the carbon to which Y is attached and the N of $NR^7$ which the carbon is attached is a single bond or a double bond, wherein, when the bond is a double bond, $R^7$ is absent and Y is H, and, when the bond is a single bond, $R^7$ is H and Y is OH;
wherein each of $T^1$ and $T^2$ is independently O, S, or $NR^8$;
wherein Z is a divalent radical of an alkane, an alkene, or an alkyne;
wherein p is an integer that is greater than or equal to 2;
wherein each of $R^3$, $R^4$, and $R^8$ is independently a hydrogen; a $C_1$-$C_{24}$ alkyl, $C_2$-$C_{24}$ alkenyl, or $C_2$-$C_{24}$ alkynyl, optionally substituted with a group selected from the group consisting of an aryl, a heterocycle, and an amine; or an aryl optionally substituted with an alkyl, an aryl, an alkoxy, a halo, an amine, a hydroxy, or a trifluoromethyl;
wherein the bond between $R^1$ and the carbon to which $R^1$ is attached is a single bond or a double bond, wherein, when the bond is a double bond, $R^2$ is absent and $R^1$ is a divalent radical derived from an alkane, or an aromatic hydrocarbon, or a heterocycle, and when the bond is a single bond, $R^1$ and $R^2$ are independently selected from the group consisting of H, $C_1$-$C_8$ alkyl, aryl, and a heterocycle; and
wherein the bond between $R^5$ and the carbon to which $R^5$ is attached is a single bond or a double bond, wherein, when the bond is a double bond, $R^6$ is absent and $R^5$ is a divalent radical derived from an alkane, an aromatic hydrocarbon, or a heterocycle, and when the bond is a single bond, $R^5$ and $R^6$ are independently selected from the group consisting of H, $C_1$-$C_8$ alkyl, aryl, and a heterocycle;
or a salt thereof; and
wherein the compound is a solid;
which method comprises:
(a) providing a compound of Formula II:

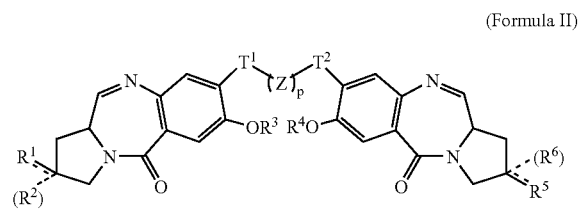

(Formula II)

wherein the definitions of $R^1$, $R^2$, $R^3$, $R^4$, $R^5$, $R^6$, $T^1$, $T^2$, Z, and p are the same as those for Formula I; and
(b) contacting the compound of Formula II with water, whereby the solid compound of Formula I is formed.

17. A method of preparing the compound or a salt thereof of claim 1, wherein the compound is of Formula I

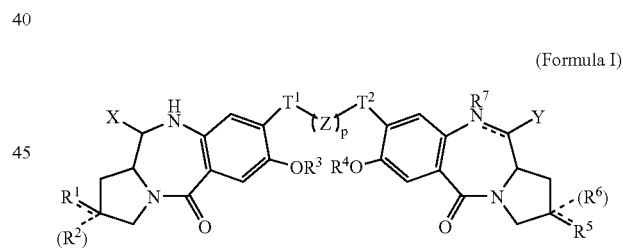

(Formula I)

wherein X is a substituent selected from the group consisting of an OH, —OR, —$OSiH_3$, —OSiRR'R", —OCOR, —OCOOR, —OCONHR, —OCSNHR, —SH, —SR, —SOR, —SOOR, —$OSO_2R$, —$OSO_2H$, —NHSOOR, —$NH_2$, —NHCOR, —NR'COR, —NHR, —NRR', —$N_3$, —CN, halogen, —$P^+Ph_3X^-$, —$SiH_3$, —SiRR'R", —OCSOR, —OCO(CHR)$_u$COOR, —OCO(CHR)$_u$SR', OCO(CHR)$_u$NR'R", —OCO(CHR)$_u$P(=)R'R", —OCO(CHR)$_u$P(=O)(OH)(R'), cysteine, glutathione,

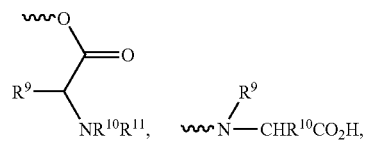

$NR^{10}R^{11}$,    $N$—$CHR^{10}CO_2H$,

-continued

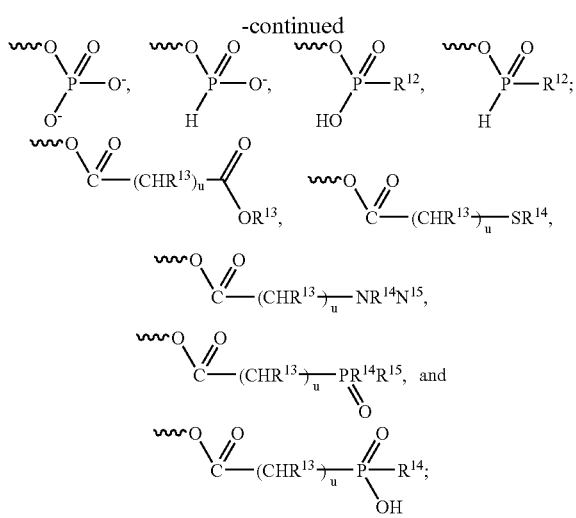

wherein each of $R^9$, $R^{10}$, and $R^{11}$ is independently selected from the group consisting of H, a $C_1$-$C_8$ alkyl optionally substituted with an amine or a carboxylate; an aryl; an aryl alkyl; and a heterocycle;

wherein $R^{12}$ is $C_1$-$C_8$ alkyl optionally substituted with an aryl, a heterocycle, an alkoxy, a halo, an amine, or carboxylate; an aryl; or a heterocycle, wherein each of $R^{13}$, $R^{14}$, and $R^{15}$ is independently selected from the group consisting of H; $C_1$-$C_8$ alkyl optionally substituted with an aryl, a heterocycle, an alkoxy, a halo, an amine, or carboxylate; an aryl; and a heterocycle, and wherein u is an integer from 1 to about 16, wherein the bond between the carbon to which Y is attached and the N of $NR^7$ to which the carbon is attached is a single bond or a double bond, wherein, when the bond is a double bond, $R^7$ is absent and Y is H, and, when the bond is a single bond, $R^7$ is H and Y is a substituent selected from the group defined for X, wherein Y is optionally the same as X;

wherein each of $T^1$ and $T^2$ is independently O, S, or $NR^8$;

wherein R, R', and R" are independently selected from the group consisting of $C_3$-$C_{24}$ alkyl optionally substituted with an amino, hydroxyl, or thiol group, $C_3$-$C_{24}$ cycloalkyl, $C_2$-$C_{24}$ alkenyl, $C_3$-$C_{26}$ alkoxyacetyl, and a group of the structure:

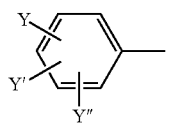

wherein Y and Y' are independently hydrogen, $C_1$-$C_{24}$ alkyl, arylalkyl, $C_2$-$C_{24}$ alkenyl, $C_2$-$C_{24}$ alkynyl, $C_1$-$C_{24}$ alkoxy, halogen, or Y and Y' taken together form 3,4-methylenedioxy, and Y" is hydrogen, $C_1$-$C_{24}$ alkyl, $C_1$-$C_{24}$ alkoxy, or halogen; naphthalenalkyl optionally substituted by methyl or halogen; phenyl($C_2$-$C_{24}$ alkenyl) wherein phenyl is optionally substituted with methyl or halogen; cinnamyl; pyridinealkyl optionally substituted with methyl or halogen; dihydropyridinealkyl optionally substituted with $C_1$-$C_{24}$ alkyl; thiophenealkyl optionally substituted with methyl or halogen; $C_6$-$C_{14}$ aryl; allyl; and furanalkyl optionally substituted with methyl or halogen;

wherein Z is a divalent radical of an alkane, an alkene, or an alkyne;

wherein p is an integer that is greater than or equal to 2;

wherein each of $R^3$, $R^4$, and $R^8$ is independently a hydrogen; a $C_1$-$C_{24}$ alkyl, $C_2$-$C_{24}$ alkenyl, or $C_2$-$C_{24}$ alkynyl, optionally substituted with a group selected from the group consisting of an aryl, a heterocycle, and an amine; or an aryl optionally substituted with an alkyl, an aryl, an alkoxy, a halo, an amine, a hydroxy, or a trifluoromethyl;

wherein the bond between $R^1$ and the carbon to which $R^1$ is attached is a single bond or a double bond, wherein, when the bond is a double bond, $R^2$ is absent and $R^1$ is a divalent radical derived from an alkane, or an aromatic hydrocarbon, and when the bond is a single bond, $R^1$ and $R^2$ are independently selected from the group consisting of H, $C_1$-$C_8$ alkyl, aryl, and wherein the bond between $R^5$ and the carbon to which $R^5$ is attached is a single bond or a double bond, wherein, when the bond is a double bond, $R^6$ is absent and $R^5$ is a divalent radical derived from an alkane, or an aromatic hydrocarbon, and when the bond is a single bond, $R^5$ and $R^6$ are independently selected from the group consisting of H, $C_1$-$C_8$ alkyl, and aryl;

or a salt thereof; and wherein the compound is a solid;

which method comprises:

(a) providing a compound of Formula II:

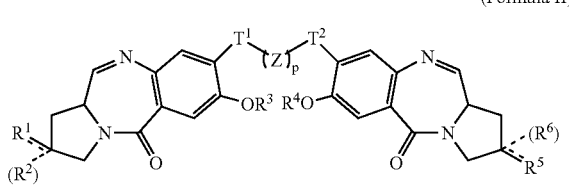

(Formula II)

wherein the definitions of $R^1$, $R^2$, $R^3$, $R^4$, $R^5$, $R^6$, $T^1$, T2, Z, and p are the same as those for Formula I; and (b) combining the compound of Formula II with a nucleophilic organic reactant, wherein the nucleophilic part of the nucleophilic organic reactant provides X, whereby the solid compound of Formula I is formed.

18. A method of preparing the compound or a salt thereof of claim 2, wherein the compound is of Formula I

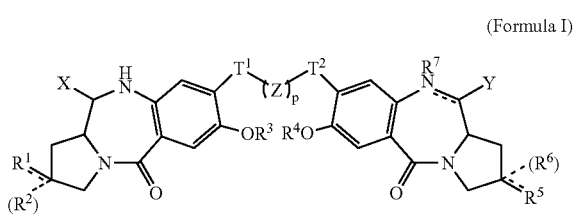

(Formula I)

wherein X is a substituent selected from the group consisting of an OH, —OR, —OSiH$_3$, —OSiRR'R", —OCOR, —OCOOR, —OCONHR, —OCSNHR, —SH, —SR, —SOR, —SOOR, —OSO$_2$R, —OSO$_2$H, —NHSOOR, —NH$_2$, —NHCOR, —NR'COR, —NHR, —NRR'—N$_3$, —CN, halogen, —P$^+$Ph$_3$X$^-$, —SiH$_3$, —SiRR'R", —OCSOR, —OCO(CHR)$_u$COOR, —OCO(CHR)$_u$SR', —OCO(CHR)$_u$NR'R", —OCO(CHR)$_u$P(=O)R'R", —OCO(CHR)$_u$P(=O)(OH)(R'), cysteine, glutathione,

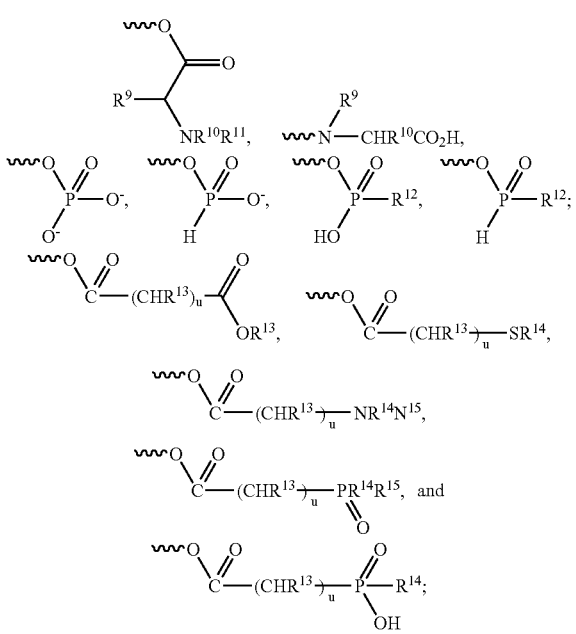

wherein each of $R^9$, $R^{10}$, and $R^{11}$ is independently selected from the group consisting of H, a $C_1$-$C_8$ alkyl optionally substituted with an amine or a carboxylate; an aryl; an aryl alkyl; and a heterocycle;

wherein $R^{12}$ is $C_1$-$C_8$ alkyl optionally substituted with an aryl, a heterocycle, an alkoxy, a halo, an amine, or carboxylate; an aryl; or a heterocycle, wherein each of $R^{13}$, $R^{14}$, and $R^{15}$ is independently selected from the group consisting of H; $C_1$-$C_8$ alkyl optionally substituted with an aryl, a heterocycle, an alkoxy, a halo, an amine, or carboxylate; an aryl; and a heterocycle, and wherein u is an integer from 1 to about 16, wherein the bond between the carbon to which Y is attached and the N of $NR^7$ to which the carbon is attached is a single bond or a double bond, wherein, when the bond is a double bond, $R^7$ is absent and Y is H, and, when the bond is a single bond, $R^7$ is H and Y is a substituent selected from the group defined for X, wherein Y is optionally the same as X;

wherein each of $T^1$ and $T^2$ is independently O, S, or $NR^8$;

wherein R, R', and R" are independently selected from the group consisting of $C_1$-$C_{24}$ alkyl optionally substituted with an amino, hydroxyl, or thiol group, $C_3$-$C_{24}$ cycloalkyl, $C_2$-$C_{24}$ alkenyl, $C_3$-$C_{26}$ alkoxyacetyl, and a group of the structure:

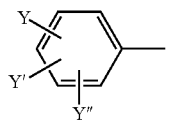

wherein Y and Y' are independently hydrogen, $C_1$-$C_{24}$ alkyl, arylalkyl, $C_2$-$C_{24}$ alkenyl, $C_2$-$C_{24}$ alkynyl, $C_1$-$C_{24}$ alkoxy, halogen, or Y and Y' taken together form 3,4-methylenedioxy, and Y" is hydrogen, $C_1$-$C_{24}$ alkyl, $C_1$-$C_{24}$ alkoxy, or halogen; naphthalenalkyl optionally substituted by methyl or halogen; phenyl($C_2$-$C_{24}$ alkenyl) wherein the phenyl is optionally substituted with methyl or halogen; cinnamyl; pyridinealkyl optionally substituted with methyl or halogen; dihydropyridinealkyl optionally substituted with $C_1$-$C_{24}$ alkyl; thiophenealkyl optionally substituted with methyl or halogen; $C_6$-$C_{14}$ aryl; allyl; and furanalkyl optionally substituted with methyl or halogen;

wherein Z is a divalent radical of an alkane, an alkene, or an alkyne;

wherein p is an integer that is greater than or equal to 2;

wherein each of $R^3$, $R^4$, and $R^8$ is independently a hydrogen; a $C_1$-$C_{24}$ alkyl, $C_2$-$C_{24}$ alkenyl, or $C_2$-$C_{24}$ alkynyl, optionally substituted with a group selected from the group consisting of an aryl, a heterocycle, and an amine; or an aryl optionally substituted with an alkyl, an aryl, an alkoxy, a halo, an amine, a hydroxy, or a trifluoromethyl;

wherein the bond between $R^1$ and the carbon to which $R^1$ is attached is a single bond or a double bond, wherein, when the bond is a double bond, $R^2$ is absent and $R^1$ is a divalent radical derived from an alkane, or an aromatic hydrocarbon, or a heterocycle, and when the bond is a single bond, $R^1$ and $R^2$ are independently selected from the group consisting of H, $C_1$-$C_8$ alkyl, aryl, and a heterocycle; and wherein the bond between $R^5$ and the carbon to which $R^5$ is attached is a single bond or a double bond, wherein, when the bond is a double bond, $R^6$ is absent and $R^5$ is a divalent radical derived from an alkane, or an aromatic hydrocarbon, or a heterocycle, and when the bond is a single bond, $R^5$ and $R^6$ are independently selected from the group consisting of H, $C_1$-$C_8$ alkyl, aryl, and a heterocycle;

or a salt thereof; and provided that, when each of $R^1$ and $R^5$ is $CH_2$ attached by a double-bond, $R^2$ and $R^6$ are absent, $R^3$ and $R^4$ are $C_3$, $R^7$ is H, $T^1$ and $T^2$ are both O, Z is $CH_2$, and p is 3, then X and Y are not both methoxy, both ethoxy, or both hydroxyl; and when each of $R^1$, $R^2$, $R^5$, and $R^6$ are H, then X and Y are not both sulfide or both ether;

which method comprises:

(a) providing a compound of Formula II:

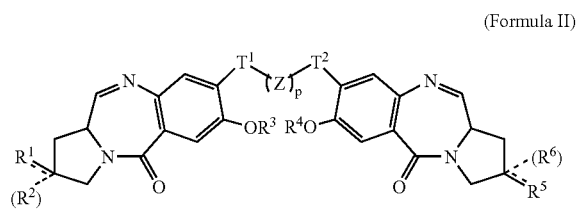

(Formula II)

wherein the definitions of $R^1$, $R^2$, $R^3$, $R^4$, $R^5$, $R^6$, $T^1$, $T^2$, Z, and p are the same as those for Formula I; and (b) combining the compound of Formula II with a nucleophilic organic reactant other than methanol or ethanol, wherein the nucleophilic part of the nucleophilic organic reactant provides X, whereby the solid compound of Formula I is formed.

19. A method of preparing the compound or a salt thereof of claim 3, wherein the compound is of Formula I

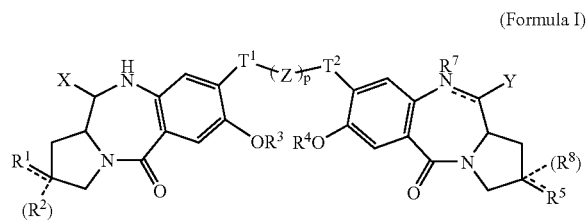

(Formula I)

wherein X is a substituent selected from the group consisting of —OSiH₃, —OSiRR'R", —OCOR, —OCOOR, —OCONHR, —OCSNHR, —SH, —SR, —SOR, —SOOR, —OSO₂R, —OSO₂H, —NHSOOR, —NH₂, —NHCOR, —NR'COR, —NHR, —NRR', —N₃, —CN, halogen, —P⁺Ph₃X⁻, —SiH₃, —SiRR'R", cysteine, glutathione,

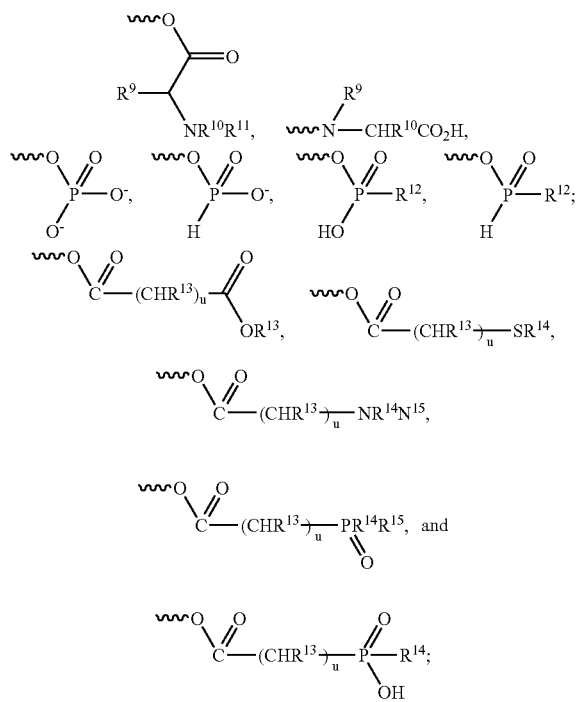

wherein each of R⁹, R¹⁰, and R¹¹ is independently selected from the group consisting of H, a C₁-C₈ alkyl optionally substituted with an amine or a carboxylate; an aryl; an aryl alkyl; and a heterocycle;

wherein R¹² is C₁-C₈ alkyl optionally substituted with an aryl, a heterocycle, an alkoxy, a halo, an amine, or carboxylate; an aryl; or a heterocycle, wherein each of R¹³, R¹⁴, and R¹⁵ is independently selected from the group consisting of H; C₁-C₈ alkyl optionally substituted with an aryl, a heterocycle, an alkoxy, a halo, an amine, or carboxylate; an aryl; and a heterocycle, and wherein u is an integer from 1 to about 16, wherein the bond between the carbon to which Y is attached and the N of NR⁷ to which the carbon is attached is a single bond or a double bond, wherein, when the bond is a double bond, R⁷ is absent and Y is H, and, when the bond is a single bond, R⁷ is H and Y is a substituent selected from the group defined for X, wherein Y is optionally the same as X;

wherein each of T¹ and T² is independently O, S, or NR⁸;

wherein R, R', and R" are independently selected from the group consisting of C₁-C₂₄ alkyl optionally substituted with an amino, hydroxyl, or thiol group, C₃-C₂₄ cycloalkyl, C₂-C₂₄ alkenyl, C₃-C₂₆ alkoxyacetyl, and a group of the structure:

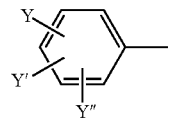

wherein Y and Y' are independently hydrogen, C₁-C₂₄ alkyl, arylalkyl, C₂-C₂₄ alkenyl, C₂-C₂₄ alkynyl, C₁-C₂₄ alkoxy, halogen, or Y and Y' taken together form 3,4-methylenedioxy, and Y" is hydrogen, C₁-C₂₄ alkyl, C₁-C₂₄ alkoxy, or halogen; naphthalenalkyl optionally substituted by methyl or halogen; phenyl(C₂-C₂₄ alkenyl) wherein the phenyl is optionally substituted with methyl or halogen; cinnamyl; pyridinealkyl optionally substituted with methyl or halogen; dihydropyridinealkyl optionally substituted with C₁-C₂₄ alkyl; thiophenealkyl optionally substituted with methyl or halogen; C₆-C₁₄ aryl; allyl; and furanalkyl optionally substituted with methyl or halogen;

wherein Z is a divalent radical of an alkane, an alkene, or an alkyne;

wherein p is an integer that is greater than or equal to 2;

wherein each of R³, R⁴, and R⁸ is independently a hydrogen; a C₁-C₂₄ alkyl, C₂-C₂₄ alkenyl, or C₂-C₂₄ alkynyl, optionally substituted with a group selected from the group consisting of an aryl, a heterocycle, and an amine; or an aryl optionally substituted with an alkyl, an aryl, an alkoxy, a halo, an amine, a hydroxy, or a trifluoromethyl;

wherein the bond between R¹ and the carbon to which R¹ is attached is a single bond or a double bond, wherein, when the bond is a double bond, R² is absent and R¹ is a divalent radical derived from an alkane or an aromatic hydrocarbon, or a heterocycle and when the bond is a single bond, R¹ and R² are independently selected from the group consisting of H, C₁-C₈ alkyl, and aryl, and a heterocycle; and wherein the bond between R⁵ and the carbon to which R⁵ is attached is a single bond or a double bond, wherein, when the bond is a double bond, R⁶ is absent and R⁵ is a divalent radical derived from an alkane, an aromatic hydrocarbon, or a heterocycle, and when the bond is a single bond, R⁵ and R⁶ are independently selected from the group consisting of H, C₁-C₈ alkyl, aryl, and a heterocycle;

or a salt thereof; and which method comprises:
(a) providing a compound of Formula II:

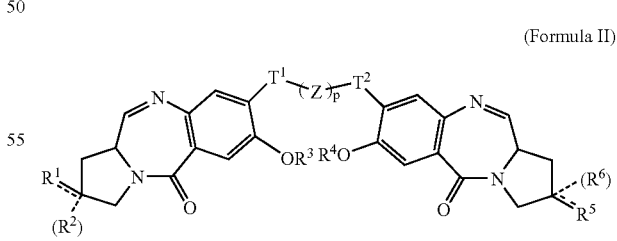

(Formula II)

wherein the definitions of R¹, R², R³, R⁴, R⁵, R⁶, T¹, T², Z, and p are the same as those for Formula I; and (b) combining the compound of Formula II with a nucleophilic organic reactant, wherein the nucleophilic part of the nucleophilic organic reactant provides X, and whereby the solid compound of Formula I is formed.

20. The compound or a salt thereof of claim 1, wherein X is selected from the group consisting of OR, SR, and an amine; wherein R is independently a hydrogen, a $C_1$-$C_{24}$ alkyl, or a group of structure

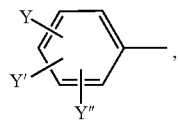

wherein each of Y and Y' is independently hydrogen, $C_1$-$C_{24}$ alkyl, $C_1$-$C_{24}$ alkoxy, or halogen, or Y and Y' together form 3,4-methylenedioxy, and Y" is hydrogen, $C_1$-$C_{24}$ alkyl, $C_1$-$C_{24}$ alkoxy or halogen; wherein the bond between the carbon to which Y is attached and the N of $NR^7$ which the carbon is attached is a single bond; wherein Y is the same as X; wherein each of $T^1$ and $T^2$ is O; wherein Z is a divalent radical of an alkane; wherein p is 3; wherein each of $R^3$ and $R^4$ is independently a hydrogen or a $C_1$-$C_{24}$ alkyl; wherein the bond between $R^1$ and the carbon to which $R^1$ is attached is a single bond; and wherein the bond between $R^5$ and the carbon to which $R^5$ attached is a single bond.

21. The compound or a salt thereof of claim 2, wherein each of $T^1$ and $T^2$ is O, p is 3 and Z is —$CH_2$—.

22. The compound or a salt thereof of claim 2, wherein each of $R^3$ and $R^4$ is a $C_1$-$C_4$ alkyl optionally substituted with a group selected from the group consisting of an aryl, a heterocycle, and an amine; or an aryl optionally substituted with an alkyl, an aryl, an alkoxy, a halo, an amine, a hydroxy, and a trifluoromethyl.

23. The compound or a salt thereof of claim 2, wherein (a) each of X and Y is OH, (b) X is OH and Y is H, or (c) X is OR and R is a $C_1$-$C_{24}$ alkyl.

24. The compound or a salt thereof of claim 22, wherein X is OR and R is methyl, ethyl, isopropyl, or t-butyl.

25. The compound or a salt thereof of claim 2, wherein the compound is selected from the group consisting of:

wherein, for structure (c), the following applies: R is a $C_1$-$C_{24}$ alkyl optionally substituted with an amino, hydroxyl, or thiol group; $C_3$-$C_{24}$ cycloalkyl, a $C_2$$C_{24}$ alkenyl; a $C_3$-$C_{26}$ alkoxyacetyl; a naphthalenalkyl optionally substituted with methyl or halogen; a phenyl ($C_3$-$C_{26}$ alkenyl), wherein the phenyl is optionally substituted with methyl or halogen; a cinnamyl; a pyridinealkyl optionally substituted with methyl or halogen; a dihydropyridine alkyl optionally substituted with $C_1$-$C_{24}$ alkyl; a thiophenealkyl optionally substituted with methyl or halogen; an aryl; an allyl; a furanalkyl optionally substituted with methyl or halogen; or a group of structure

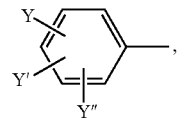

wherein each of Y and Y' is independently hydrogen, $C_1$-$C_{24}$ alkyl, arylalkyl, $C_2$-$C_{24}$ alkenyl, $C_2$-$C_{24}$ alkynyl, $C_1$-$C_{24}$ alkoxy, or halogen, or Y and Y' together form 3,4-methylenedioxy, and Y" is hydrogen, $C_1$-$C_{24}$ alkyl, $C_1$-$C_{24}$ alkoxy or halogen.

26. The compound or a salt thereof of claim 2, wherein the compound is

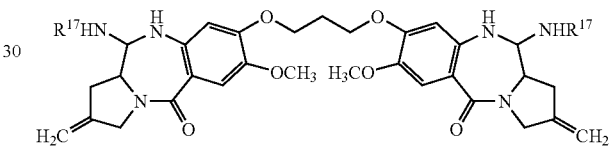

wherein R is a $C_1$-$C_{24}$ alkyl optionally substituted with an amino, hydroxyl, or thiol group; a $C_3$-$C_{24}$ cycloalkyl, a $C_2$-$C_{24}$ alkenyl; a $C_3$-$C_{26}$ alkoxyacetyl; a naphthalenalkyl optionally substituted with methyl or halogen; phenyl ($C_2$-

(a)

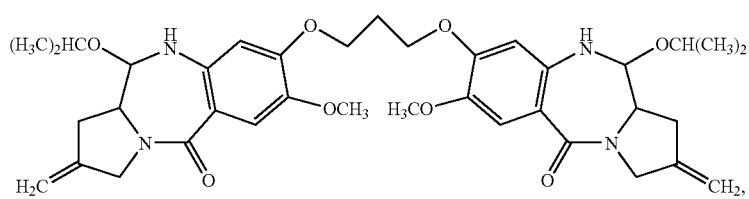

(b)

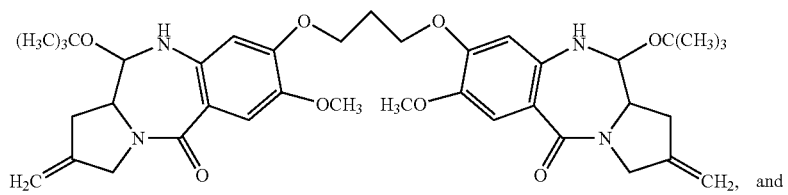

and (c)

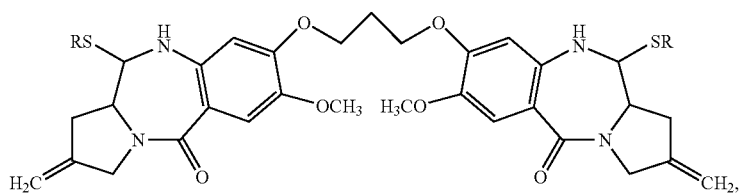

$C_1$-$C_{24}$ alkenyl), wherein the phenyl is optionally substituted with methyl or halogen; cinnamyl; pyridinealkyl optionally substituted with methyl or halogen; dihydropyridine alkyl optionally substituted with $C_1$-$C_{24}$ alkyl; thiophenealkyl optionally substituted with methyl or halogen; an aryl; an allyl; furanalkyl optionally substituted with methyl or halogen; or a group of structure

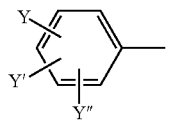

wherein each of Y and Y' is independently hydrogen, $C_1$-$C_{24}$ alkyl, arylalkyl, $C_2$-$C_{24}$ alkenyl, $C_2$-$C_{24}$ alkynyl, $C_1$-$C_{24}$ alkoxy, or halogen, or Y and Y' together form 3,4-methylenedioxy, and Y" is hydrogen, $C_1$-$C_{24}$ alkyl, $C_1$-$C_{24}$ alkoxy or halogen.

27. A pharmaceutical composition comprising a compound or a salt thereof of claim 2 and a pharmaceutically acceptable carrier.

28. The compound or a salt thereof of claim 3, wherein each of $T^1$ and $T^2$ is O, p is 3 and Z is —$CH_2$—.

29. The compound or a salt thereof of claim 3, wherein each of $R^3$ and $R^4$ is a $C_1$-$C_4$ alkyl optionally substituted with a group selected from the group consisting of an aryl and an amine; or an aryl optionally substituted with an alkyl, an aryl, an alkoxy, a halo, an amine, a hydroxy, or a trifluoromethyl.

30. A pharmaceutical composition comprising a compound or a salt thereof of claim 3 and a pharmaceutically acceptable carrier.

31. A method of treating cancer in a host comprising administering to a host a compound or a salt thereof of claim 1 in an amount effective to treat cancer in the host, wherein the cancer is leukemia, non-small cell lung cancer, colon cancer, cancer of the central nervous system, melanoma, ovarian cancer, renal cancer, prostate cancer, or breast cancer.

32. The method of claim 31, wherein the host is a human.

33. The method of claim 31, wherein the compound or salt thereof is administered as an injectable formulation.

34. A method of treating cancer in a host comprising administering to a host a compound or a salt thereof of claim 2 in an amount effective to treat cancer in the host, wherein the cancer is leukemia, non-small cell lung cancer, colon cancer, cancer of the central nervous system, melanoma, ovarian cancer, renal cancer, prostate cancer, or breast cancer.

35. The method of claim 34, wherein the host is a human.

36. The method of claim 34, wherein the compound or salt thereof is administered as an injectable formulation.

37. A method of treating cancer in a host comprising administering to a host a compound or a salt thereof of claim 3 in an amount effective to treat cancer in the host, wherein the cancer is leukemia, non-small cell lung cancer, colon cancer, cancer of the central nervous system, melanoma, ovarian cancer, renal cancer, prostate cancer, or breast cancer.

38. The method of claim 37, wherein the host is a human.

39. The method of claim 37, wherein the compound or salt thereof is administered as an injectable formulation.

* * * * *

UNITED STATES PATENT AND TRADEMARK OFFICE
CERTIFICATE OF CORRECTION

PATENT NO. : 7,511,032 B2
APPLICATION NO. : 10/576689
DATED : March 31, 2009
INVENTOR(S) : Liu et al.

Page 1 of 1

It is certified that error appears in the above-identified patent and that said Letters Patent is hereby corrected as shown below:

IN COLUMN 43:

"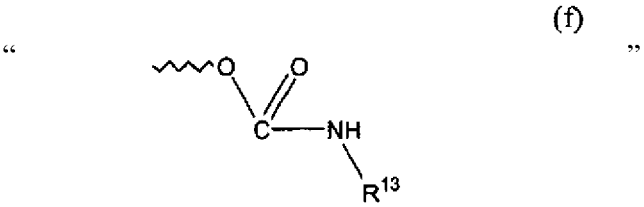 (f)"

should read:

-- 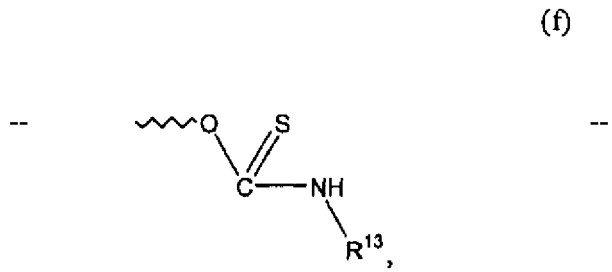 (f) --

Signed and Sealed this

Eighteenth Day of August, 2009

David J. Kappos
*Director of the United States Patent and Trademark Office*